Figure 1:
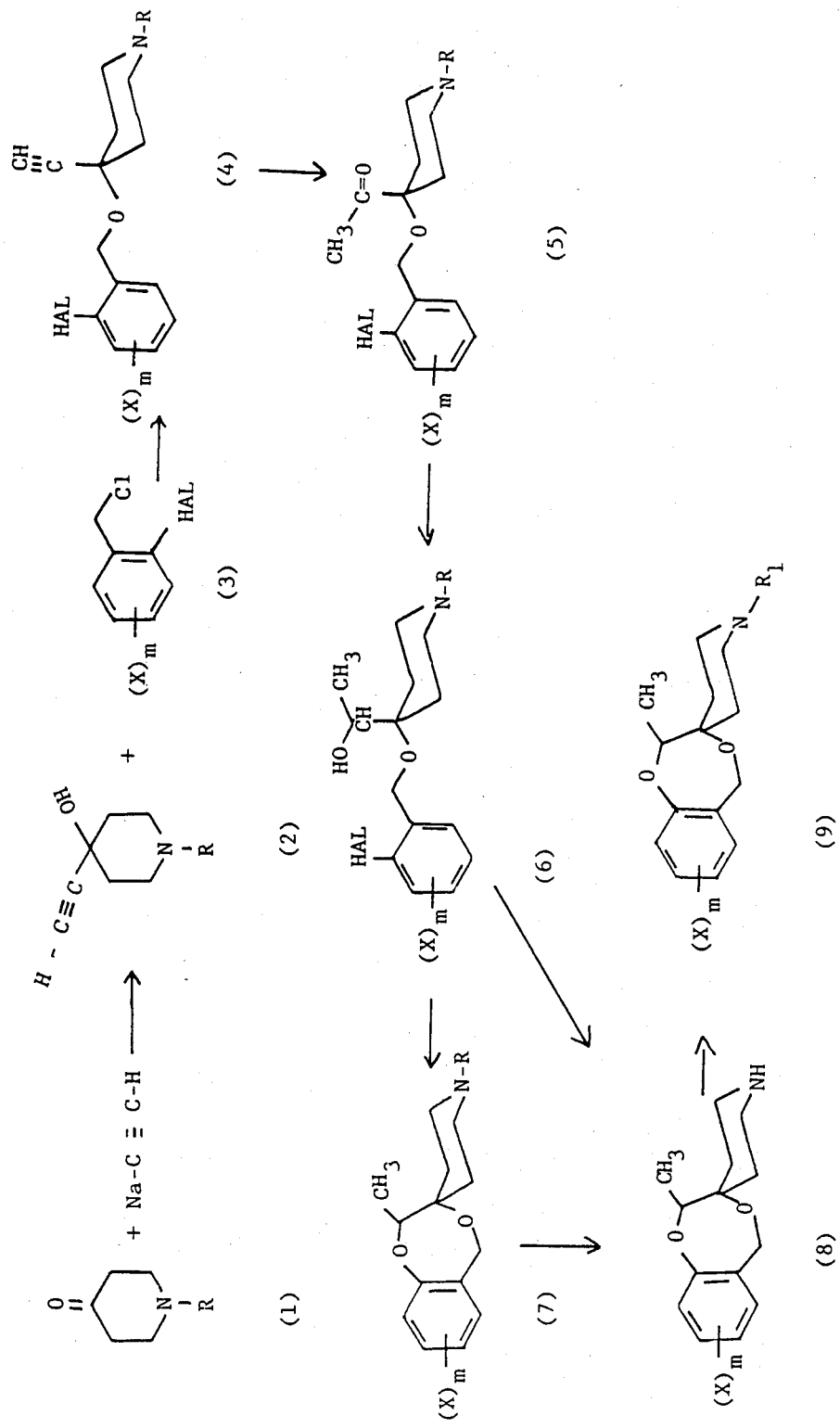

United States Patent [19]

Kosley, Jr. et al.

[11] Patent Number: 4,521,537
[45] Date of Patent: * Jun. 4, 1985

[54] SPIRO[2H-1,4-BENZODIOXEPIN-3(5H)4'-PIPERIDINE AND -3'-PYRROLIDINE] COMPOUNDS AND THEIR USE AS ANTIHYPERTENSIVE AGENTS

[75] Inventors: Raymond W. Kosley, Jr., Bridgewater; Robert J. Cherill, Somerset, both of N.J.

[73] Assignee: Hoechst-Roussel Pharmaceuticals Incorporated, Somerville, N.J.

[ * ] Notice: The portion of the term of this patent subsequent to Sep. 20, 2000 has been disclaimed.

[21] Appl. No.: 595,781

[22] Filed: Apr. 2, 1984

Related U.S. Application Data

[63] Continuation-in-part of Ser. No. 410,155, Aug. 20, 1982, Pat. No. 4,405,631.

[51] Int. Cl.³ .............. C07D 491/113; A61K 31/455
[52] U.S. Cl. .................................. 514/302; 514/412; 546/17; 546/216; 546/221; 546/208; 548/409
[58] Field of Search .................. 546/17; 548/409; 424/267, 274

[56] References Cited

U.S. PATENT DOCUMENTS

| 3,679,666 | 7/1972 | Maiatestinic et al. | 424/267 |
| 4,405,631 | 9/1983 | Kosley et al. | 424/267 |

FOREIGN PATENT DOCUMENTS

| 1312894 | 11/1962 | France | 424/278 |
| 469736 | 4/1969 | Switzerland | 424/267 |

*Primary Examiner*—Robert T. Bond

[57] ABSTRACT

Spiro[2H-1,4-benzodioxepin-3(5H)4'-piperidine and -3'-pyrrolidine] compounds of the formula

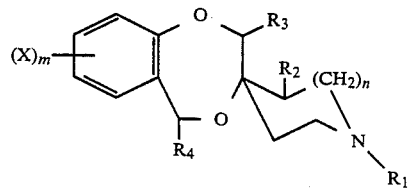

where the substituents are as defined herein, are useful in the treatment of hypertension in mammals. Such compounds, their use as antihypertensive agents, pharmaceutical compositions containing the compounds, intermediates and processes for preparing the compounds are provided.

89 Claims, 2 Drawing Figures

FIG. I

SPIRO[2H-1,4-BENZODIOXEPIN-3(5H)4'-PIPERIDINE AND -3'-PYRROLIDINE] COMPOUNDS AND THEIR USE AS ANTIHYPERTENSIVE AGENTS

CROSS REFERENCE TO RELATED APPLICATION

This application is a continuation-in-part of copending application Ser. No. 410,155, filed Aug. 20, 1982, the entire disclosure of which is relied upon and incorporated herein by reference. Ser. No. 410,155 has issued as U.S. Pat. No. 4,405,631, issued Sept. 20, 1983.

This invention relates to spiro[2H-1,4-benzodioxepin-3(5H)4'-piperidine and -3'-pyrrolidine]compounds. The compounds are useful in the treatment of hypertension and as analgesics in mammals.

Hypertension in mammals may accompany many disorders, such as renal disease, disease of the adrenal gland and toxemia of pregnancy. In most patients with high blood pressure, however, no primary disorder is evident and the condition is referred to as essential hypertension.

In controlled trials with patients afflicted with hypertension, it has been found that hypertensive patients have more frequent cerebral and other cardiovascular accidents than those whose blood pressure has been lowered by drugs. In addition, although hypertension may exist without inducing symptoms in the patient, it is more usual that clinical manifestations develop after elevated blood pressure has persisted for some time. For example, hypertension has been associated with secondary effects, such as headache, dizziness, nose-bleeding, breathlessness on exertion, heart failure and stroke. Since these secondary effects may present a danger to life, it is desirable to lower the blood pressure and maintain it at a more nearly normal level.

A variety of antihypertensive drugs have been introduced for the treatment of elevated blood pressure. Their development has represented an important advance in modern medicine. Intensive efforts are being made to develop new types of antihypertensive drugs and the need for such drugs continues.

In addition, one of the most important as well as one of the original purposes for which drugs have been used is the relief of pain. Efforts to develop new types of analgesic drugs and the need for such drugs also continues.

This invention aids in fulfilling the need in the art for antihypertensive agents by providing compounds of the formula

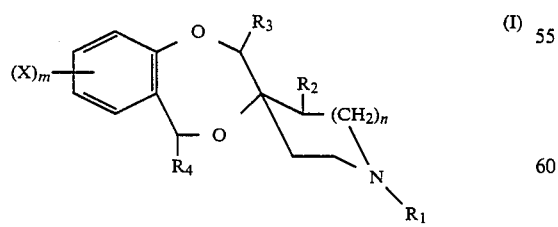

(I)

wherein
m is zero, 1 or 2;
n is zero or 1;
$R_1$ is
(a) a $C_1$ to $C_5$ branched or straight chain alkyl group
(b) a terminally substituted $C_1$ to $C_5$ branched or straight chain alkyl group, or a terminally substituted $C_2$ to $C_5$ branched or straight chain alkenyl group, or a terminally substituted $C_4$ alkynyl group, wherein the terminal substituents are one or two substituents independently selected from the group consisting of

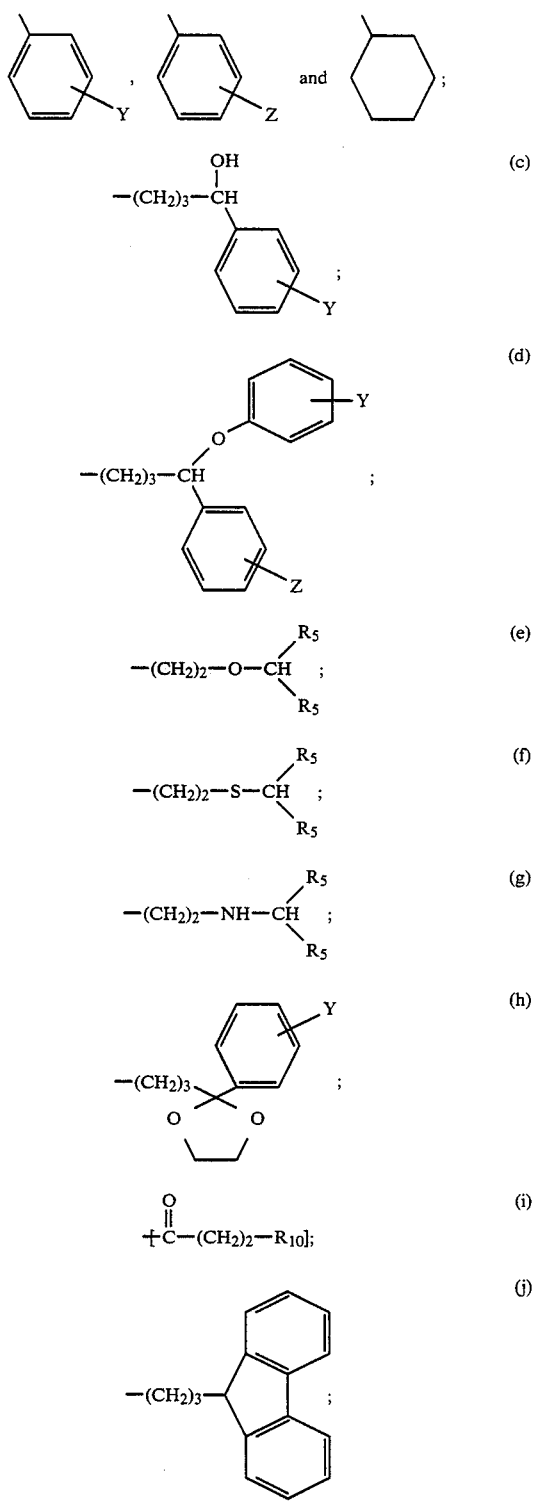

-continued

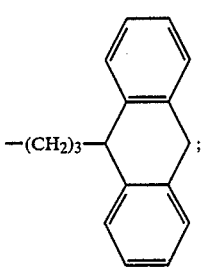  (k)

(l) a $C_1$ or $C_2$ alkylene group terminally substituted by

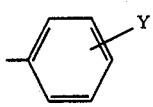

or $C_3$ or $C_5$ cycloalkyl;

(m) a $C_2$ to $C_3$ branched or straight chain alkylene group terminally substituted by one substituent selected from the group consisting of

—OH, —CN, —NR$_{12}$R$_{13}$,

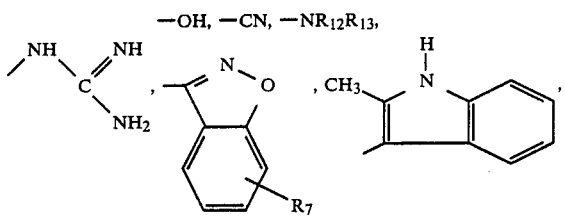

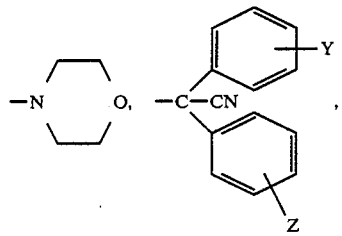

—CN;  (n)

$\underset{\|}{\overset{NH}{-C}}$—OR$_8$;  (o)

$\underset{\|}{\overset{O}{-C}}$NR$_{12}$R$_{13}$;  (p)

$\underset{\|}{\overset{O}{-C}}$—R$_8$;  (q)

-continued

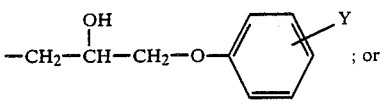  (r)

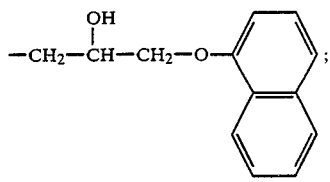  (s)

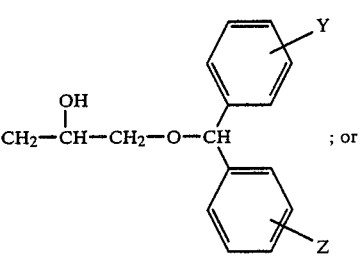  (t)

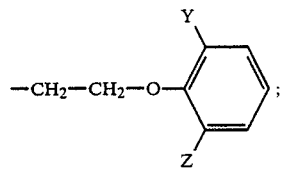  (u)

R$_2$ is hydrogen when n=0 or R$_2$ is hydrogen or a $C_1$ to $C_3$ straight chain alkyl group when n=1;
R$_3$ is hydrogen or a $C_1$ to $C_3$ straight chain alkyl group;
R$_4$ is hydrogen or a $C_1$ to $C_3$ straight chain alkyl group;
each R$_5$ substituent is independently selected from the group consisting of

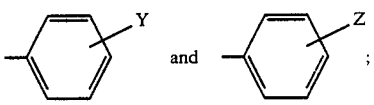

X is Cl, F, Br, I, —NO$_2$, —CF$_3$, —NR$_6$R$_7$,

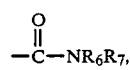

$C_1$ to $C_6$ branched or straight chain alkyl, —CN, —O—R$_6$, —SR$_7$, —SO$_3$R$_7$,

—NHCOR$_8$, —SO$_2$R$_9$ or —SOR$_9$ where
R$_6$ is hydrogen or a $C_1$ to $C_6$ straight chain alkyl group;
R$_7$ is hydrogen or a $C_1$ to $C_6$ straight chain alkyl group;
R$_8$ is a $C_1$ to $C_6$ branched or straight chain alkyl group;
R$_9$ is a $C_1$ to $C_6$ straight chain alkyl group; provided that when m=2, the X-substituents can be the same only when X is selected from the group consisting of Cl, F, Br, I, $C_1$ to $C_6$ branched or straight chain alkyl or —O—R$_6$;
Y and Z are the same or different and are independently selected from the group consisting of H, Cl, F, Br, I, —$NO_2$, —$CF_3$, $C_1$ to $C_4$ straight chain alkyl, alkoxy containing $C_1$ to $C_4$ straight chain alkyl, acyl or —$NH_2$;

$R_{10}$ is

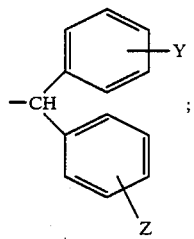

$R_{12}$ and $R_{13}$ are the same or different and are independently selected from the group consisting of hydrogen, methyl and ethyl;

and the pharmaceutically acceptable salts and optical and geometric isomers thereof.

It is to be understood that when $R_1$ is a $C_4$-alkynyl group, the acetylenic bond is between carbon atom numbers 2 and 3 of the group, i.e.,

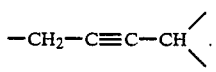

In a preferred embodiment of this invention, the compounds of formula (I) are

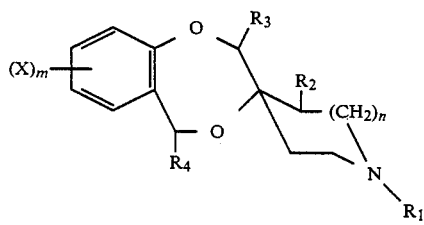 (I)

wherein $R_1$ is a $C_4$ or $C_5$ branched or straight chain alkyl or alkenyl group terminally substituted by cyclohexyl, p-fluorophenyl, bis-phenyl or bis-p-fluorophenyl groups; or $R_1$ is

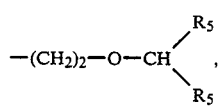

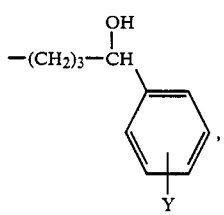

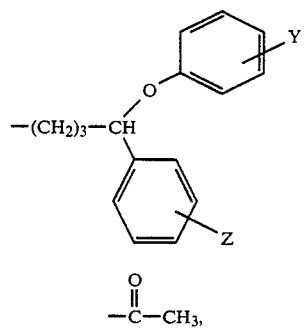

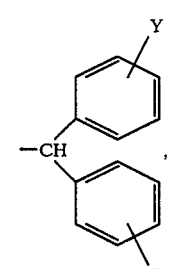

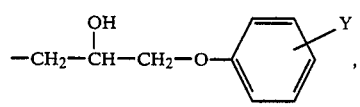

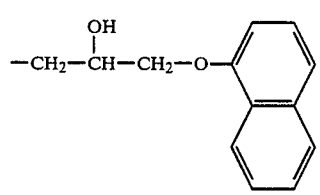

where
$R_2$, $R_3$ and $R_4$ are independently selected from hydrogen and —$CH_3$;
X is H, Cl, F, Br, I, —$NO_2$, —$CH_3$ or

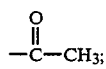

$R_5$, Y and Z are as defined above;
m is zero, 1 or 2;
n is zero or 1;
provided that, when m=2, the X-substituents can be the same only when X is selected from the group consisting of H, Cl, F, Br, I, —$CH_3$ and —$OCH_3$;
and the pharmaceutically acceptable salts and optical and geometric isomers thereof.

Particularly preferred compounds of formula (I) are

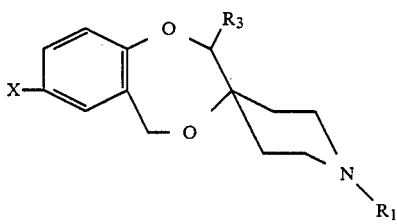 (I-A)

wherein $R_1$ is

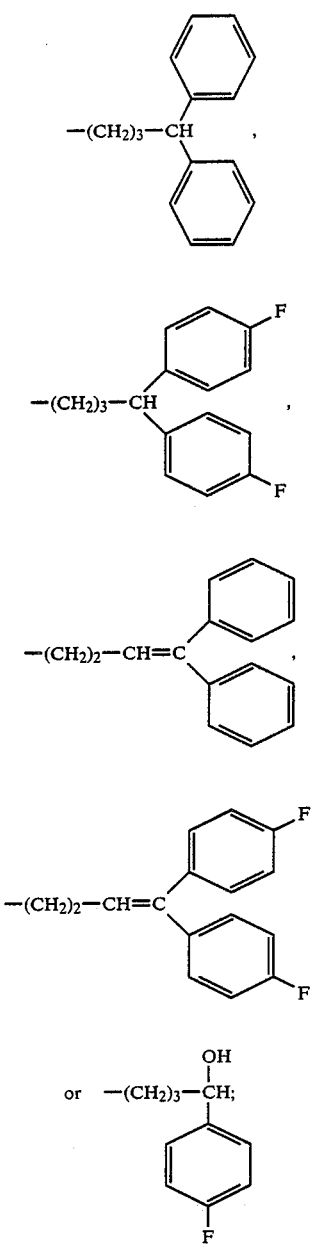

$R_3$ is H or —$CH_3$;
X is H, Cl, F or Br;
and the pharmaceutically acceptable salts and optical and geometric isomers thereof.

These compounds are particularly preferred because of their relative ease of manufacture and because they exhibit relatively high antihypertensive activity in laboratory tests on animals.

This invention aids in fulfilling the need in the art for antihypertensive and/or analgesic agents by providing compounds of the formula:

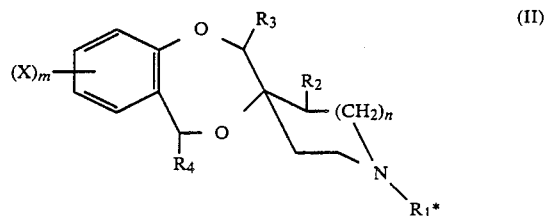

wherein $R_1^*$ is a $C_1$ to $C_5$ branched or straight chain alkyl group; a $C_1$ or $C_2$ alkylene group terminally substituted by

or $C_3$ to $C_5$ cycloalkyl a $C_2$ to $C_3$ straight chain alkylene group terminally substituted by one substituent selected from the group

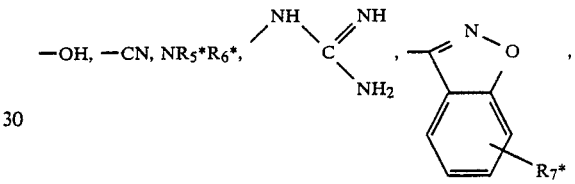

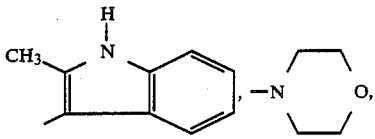

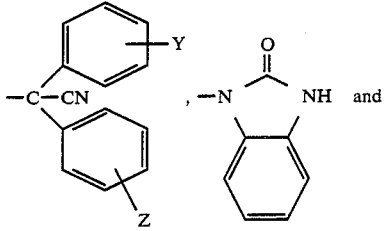

; or $R_1^*$ is —CN

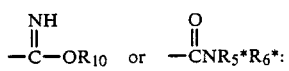

$R_5^*$ and $R_6^*$ are the same or different and are independently selected from the group consisting of hydrogen, methyl and ethyl;
$R_7^*$ is hydrogen, Cl, F, Br or I;
Y and Z are the same or different and are independently selected from the group consisting of H, Cl, F, Br, I, —$NO_2$, —$CF_3$, $C_1$ to $C_4$ straight chain alkyl, alkoxy containing $C_1$ to $C_4$ straight chain alkyl, acyl or —$NH_2$;

$R_2$ is hydrogen when n=0 or $R_2$ is hydrogen or a $C_1$ to $C_3$ straight chain alkyl group when n=1;

$R_3$ is hydrogen or a $C_1$ to $C_3$ straight chain alkyl group;

$R_4$ is hydrogen or a $C_1$ to $C_3$ straight chain alkyl group;

m is zero, 1 or 2;

X is Cl, F, Br, I, —$NO_2$, —$CF_3$, —$NR_6R_7$,

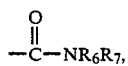

$C_1$ to $C_6$ branched or straight chain alkyl, —CN, —O—$R_6$, —$SR_7$, —$SO_7R$,

—$NHCOR_8$, —$SO_2R_9$, or —$SOR_9$ where $R_6$ is hydrogen or a $C_1$ to $C_6$ straight chain alkyl group, $R_7$ is hydrogen or a $C_1$ to $C_6$ straight chain alkyl group, $R_8$ is a $C_1$ to $C_6$ branched or straight chain alkyl group, $R_9$ is a $C_1$ to $C_6$ straight chain alkyl group;

provided that when m=2, the X-substituents can be the same only when X is selected from the group consisting of Cl, F, Br, I, $C_1$ to $C_6$ branched or straight chain alkyl or —O—$R_6$;

n is zero or 1;

and the pharmaceutically acceptable salts and optical and geometric isomers thereof.

In a preferred embodiment of this invention the compounds of formula (II) are

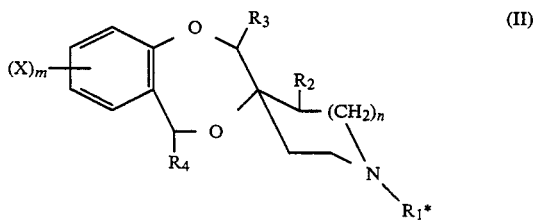

wherein $R_1^*$ is a $C_1$ to $C_5$ branched or straight chain alkyl group; a $C_2$ alkylene group terminally substituted by

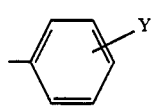

or $C_3$ to $C_5$ cycloalkyl a $C_2$ to $C_3$ straight chain alkylene group terminally substituted by one substituent selected from the group —OH, —CN, $NR_5^*R_6^*$, 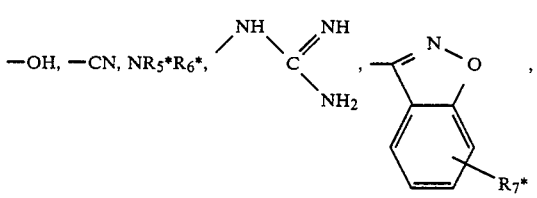

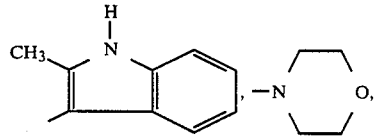

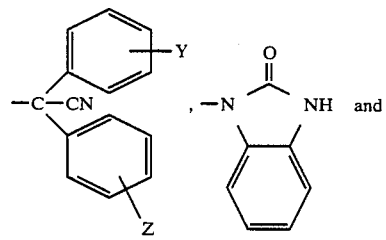

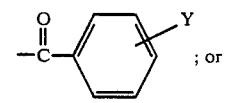

$R_1^*$ is —CN,

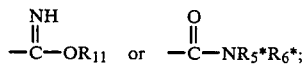

$R_5^*$ and $R_6^*$ are the same or different and are independently selected from the group consisting of hydrogen, methyl and ethyl;

$R_7^*$ is hydrogen, Cl, F, Br or I;

$R_{11}$ is a $C_1$ to $C_4$ straight chain alkyl group;

wherein Y and Z are the same or different and are independently selected from the group consisting of H, Cl, F, Br, I, —$NO_2$, —$CF_3$, $C_1$ to $C_4$ straight chain alkyl, alkoxy containing $C_1$ to $C_4$ straight chain alkyl, acyl or —$NH_2$;

$R_2$, $R_3$ and $R_4$ are independently selected from hydrogen and methyl;

X is Cl, F, Br, I, —$NO_2$, —$CH_3$ or —$OCH_3$;

m is zero, 1 or 2;

n is zero or 1;

provided that when m=2, the X-substituents can be the same only when X is selected from the group consisting of Cl, F, Br, I, —$CH_3$ and —$OCH_3$; and the pharmaceutically acceptable salts and optical and geometric isomers thereof.

Particularly preferred compounds of formula (II) are

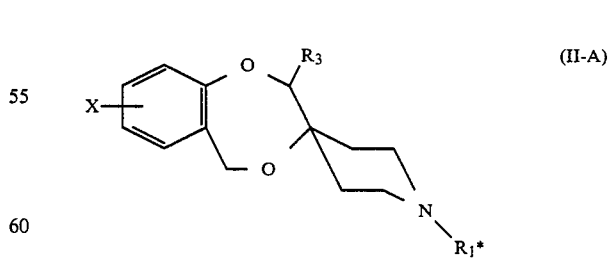

wherein $R_1^*$ is a pentyl, phenylethyl, cyanomethyl, cyanoethyl, hydroxyethyl, aminoethyl, aminopropyl, cyclopropylmethyl, 4-nitrophenylethyl, 4-aminophenylethyl, or 2-N,N-dimethylaminoethyl group, or an ethylene group terminally substituted by guanidino or

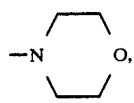

or a straight chain ethylene or propylene group terminally substituted by a

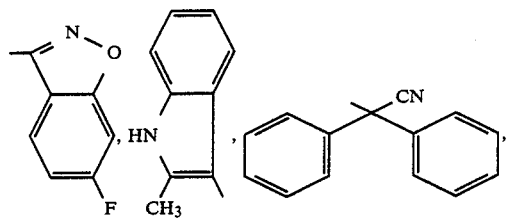

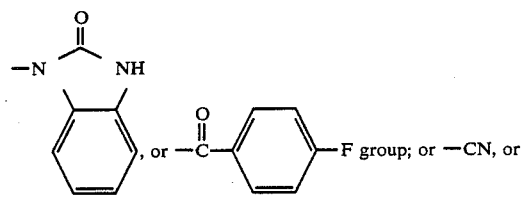

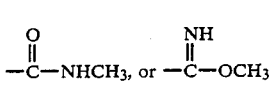 group; or —CN, or $$-\overset{O}{\underset{}{C}}-NHCH_3, \text{ or } -\overset{NH}{\underset{}{C}}-OCH_3$$

$R_3$ is H or —$CH_3$;
X is H, Cl, F or Br;
and the pharmaceutically acceptable salts and optical and geometric isomers thereof.

This invention also provides compounds of the following formulae, which are useful intermediates in the preparation of the pharmaceutically active compounds of the invention:

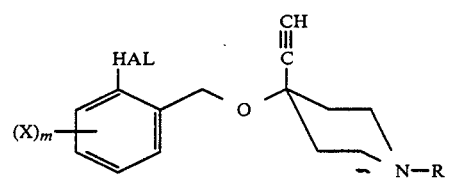 (4)

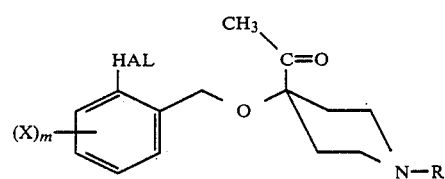 (5)

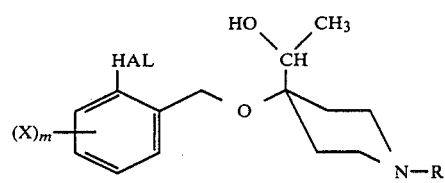 (6)

-continued

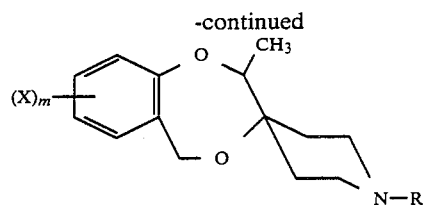 (7)

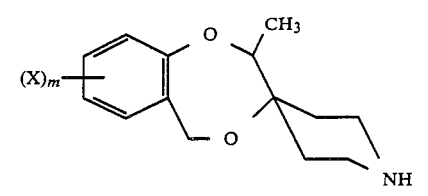 (8)

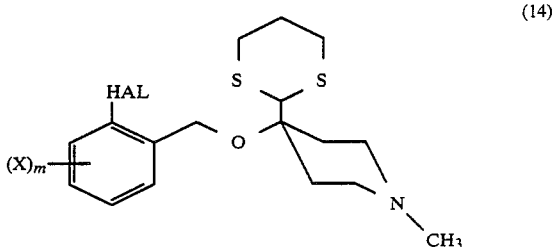 (14)

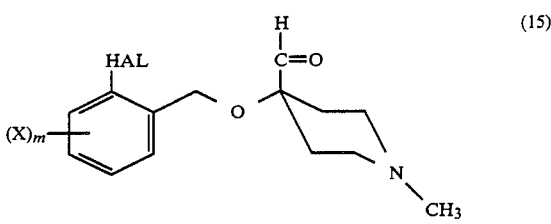 (15)

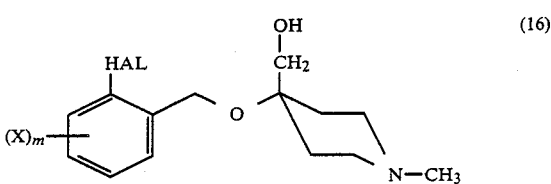 (16)

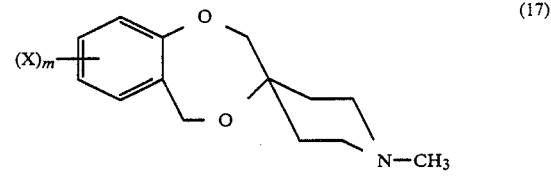 (17)

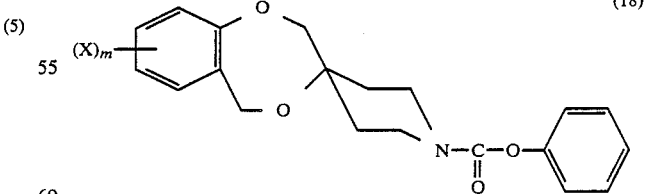 (18)

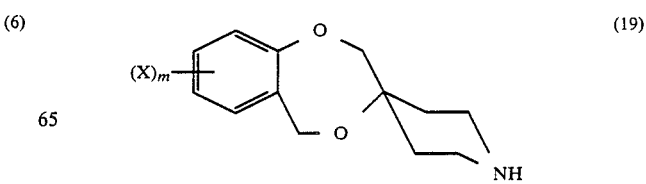 (19)

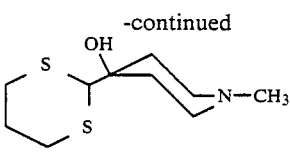

where
X and m are as previously defined;
R is hydrogen or a methyl, acyl or benzyl group; and
HAL is chlorine or fluorine.

This invention also provides processes for preparing the compounds of this invention.

Further, this invention provides a method of alleviating hypertension in a mammal by administering to a mammal a pharmaceutically active compound of the invention in an amount sufficient to reduce the blood pressure of the mammal.

Also, this invention provides compounds of the following formula, which are also useful in the preparation of the pharmaceutically active compounds of the invention:

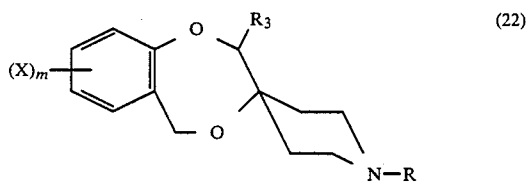

where
$R_3$, X and m are as previously defined; and
R is —CN,

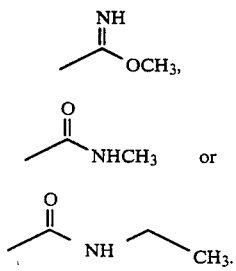

In addition, this invention provides a method of reducing pain in a mammal by administering to a mammal a pain alleviating amount of a pharmaceutically active compound of the invention.

Finally, this invention provides a pharmaceutical composition comprising a pharmaceutically active compound of the invention and a pharmaceutically acceptable carrier therefor.

The preparation of the compounds of this invention will now be explained with reference to the Figures, which are schematic diagrams depicting various routes of synthesis of piperidine derivatives of the invention. It will be understood that similar techniques can be employed to synthesize the pyrrolidine derivatives of the invention. Preparation of compounds of formula (I) will first be described.

Referring to FIG. 1, the starting reactant is an N-substituted-4-piperidone of formula (1), which is commercially available or can be prepared using well-known techniques for synthesizing organic compounds. The substituent R shown in the Figure can typically be a methyl, acyl or benzyl group. The piperidone of formula (1) can be reacted in tetrahydrofuran (THF) with an ammoniacal solution of sodium acetylide to obtain a 1-substituted-4-ethynyl-4-piperidinol of formula (2). The resulting 1-substituted-4-ethynyl-4-piperidinol can be reacted with a substituted or unsubstituted o-halobenzylchloride of formula (3) in solution in the presence of a base, such as potassium t-butoxide or sodium hydride, to yield a 1-substituted-4-ethynyl-4-(o-halobenzyloxy)piperidine of formula (4). Substituted and unsubstituted compounds of formula (3) are also readily available or can be prepared using conventional techniques. The halo group in the compounds of formula (3) is identified in FIG. 1 as HAL and is chlorine or fluorine, the latter being preferred.

Hydrolysis converts the ethynyl group in the compound of formula (4) to an oxoethyl group. This is achieved by reacting the compound of formula (4) with water catalyzed by mercuric sulphate in an acidic medium, such as methanol/sulphuric acid. The resulting 4-(1-oxoethyl)-4-(o-halobenzyloxy)-piperidine of formula (5) is isolated. If the substituent R in the compound of formula (4) is an acyl group, this group is hydrolyzed so that R is hydrogen in the compound of formula (5).

The keto group of the compound of formula (5) is reduced to a hydroxyl group in solution by sodium borohydride, for example, to form a 4-(1-hydroxyethyl)-4-(o-halobenzyloxy)piperidine of formula (6).

The alcohol of formula (6) can be cyclized to form the dioxepin ring system of the compounds of the invention. The cyclization can be carried out in the presence of a base, such as potassium t-butoxide or sodium hydride, in a solvent, such as dimethyl sulfoxide (DMSO) or THF, at temperatures from room temperature to reflux temperature. If the substituent R in the alcohol of formula (6) is hydrogen, then the compound of formula (8) in FIG. 1 will be obtained. If the substituent R is a methyl, acyl or benzyl group, then the cyclization reaction will produce a compound of formula (7).

The compound of formula (8) can be obtained from the compound of formula (7) by removing the methyl, acyl or benzyl group using conventional techniques. For example, if R is methyl, the compound of formula (7) can be converted to a carbamate, such as by reaction with ethyl chloroformate, followed by hydrolysis with a base, such as potassium hydroxide. The same technique can be employed if R is a benzyl group. Alternatively, the benzyl group can be removed by catalytic hydrogenation, such as by use of a palladium on carbon catalyst. If the substituent R is an acyl group, the acyl group will usually be removed during the formation of the compound of formula (5), but similar hydrolysis of the compound of formula (7) will yield the compound of formula (8).

The substituent $R_1$ can be introduced into the compounds by alkylation of the piperidine nitrogen of the compound of formula (8) with substituted alkyl, alkenyl or alkynyl halides or sulfonate esters to obtain a compound of formula (9). The reaction can be carried out in an aprotic solvent, such as N,N-dimethylformamide (DMF) or n-butyl acetate. The reaction is carried out in the presence of an acid scavenger, such as potassium carbonate or sodium carbonate. Sodium bicarbonate can be employed with some base sensitive materials or olefins. A catalyst, such as potassium iodide, can also be employed. The reaction is typically carried out at a temperature from about ambient to about 125° C., preferably about 20° C. to about 90° C. Typically, the reaction time will be about 45 minutes to about 18 hours. While the reactants can be employed in equimolar amounts, the alkyl, alkenyl or alkynyl halide is often used in excess amount. Generally, the alkyl, alkenyl and alkynyl halides will not exceed about 10% molar excess of the compound of formula (8). If the $R_1$ substituent contains an olefinic group, it may be necessary to add alkylating agent to the reaction medium to replace portions of the agent that may undergo side reactions. The alkylating reaction can be carried out in air or under inert gas, such as a nitrogen blanket. It is preferable to mildly agitate the reaction mixture during the course of the reaction. The alkylating agents employed in this invention are either commercially available or can be prepared by conventional techniques.

The piperidine nitrogen in the compounds of formula (I) can be acylated by reacting the corresponding unsubstituted piperidine with an acid chloride or acid anhydride. For example, acetylation is conveniently carried out with acetic anhydride in the presence of sodium acetate.

Compounds of formula (I) in which $R_1$ is the phenoxypropyl alcohol or the naphthoxypropyl alcohol can be prepared by reacting the piperidine of formula (8) with a suitable epoxide. The epoxides are commercially available or can be prepared according to conventional techniques. Similarly, the reaction of the piperidine with the epoxy compound can be carried out using the well known techniques for the necleophilic ring opening of an epoxide.

In some cases it is necessary to subject the piperidine of formula (9) to further processing to obtain the desired $R_1$-substituent. For example, compounds of the invention in which $R_1$ is

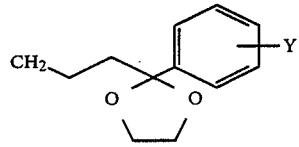

where Y is as previously defined, can be prepared by alkylation of the free base of formula (8) as previously described. The resulting compound can then be reacted with acidified aqueous alcohol solution at elevated temperature to form a piperidine of the invention in which $R_1$ is

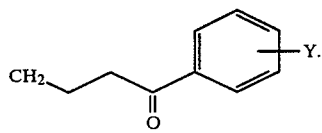

Treatment of the keto group in substituent $R_1$ with a reducing agent, such as sodium borohydride, in solution results in the formation of compounds of the invention in which $R_1$ is

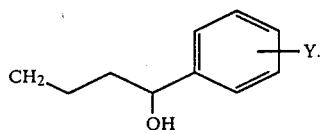

The resulting hydroxyl-containing substituent can be converted to an ether-containing substituent of the formula

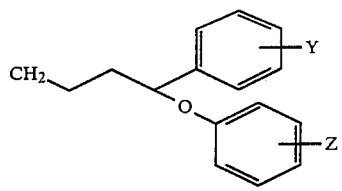

where Y and Z are previously defined, by formation of an anion with, for example, sodium hydride, and then reaction with an aryl halide, for example, 1,4-difluorobenzene.

Once the compounds of formula (7) or (8) are obtained, substituent -X can often be readily introduced into the compounds using conventional techniques. Addition of substituent -X to the benzodioxepin ring system is facilitated by the presence of the oxygen in the 1-position of the dioxepin ring, which functions as an ortho/para-directing substituent. As an example of a reaction for introducing substituent -X into the compounds of the invention, a compound of formula (7) or (8) can be reacted with N-chlorosuccinimide or N-bromosuccinimide in solution. A compound of formula (7) or (8) in which the substituent -X is chlorine or bromine, respectively, will be obtained. Other similarly well-known reactions, such as nitration by electrophilic substitution on the aromatic substrate using sodium nitrite and nitric acid, can be employed to introduce other species of the X-substituent into the compounds.

When the substituent $R_2$ is other than hydrogen the $R_2$ substituent is conveniently introduced into the compounds of the invention during an early stage of preparation. For example, $R_2$ can be substituted onto the piperidone of formula (1) by alkylation via an enamine. Thus, the piperidone can be converted to enamine, which can be alkylated. Other standard methods, such as formation of a hydrazone followed by alkylation and hydrolysis to form a ketone, can also be employed.

Compounds of the invention in which $R_4$ is other than hydrogen can also be prepared by introducing the $R_4$ substituent at an early stage of the synthesis. For instance, the substituent $R_4$ can be introduced as part of the compound of formula (3). Instead of the benzyl chloride (3), a compound of the formula

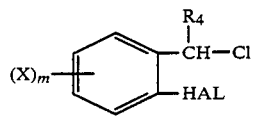

can be utilized where X, m, HAL and $R_4$ are as previously defined. Compounds of this type can be readily prepared using conventional techniques.

Figure 2:
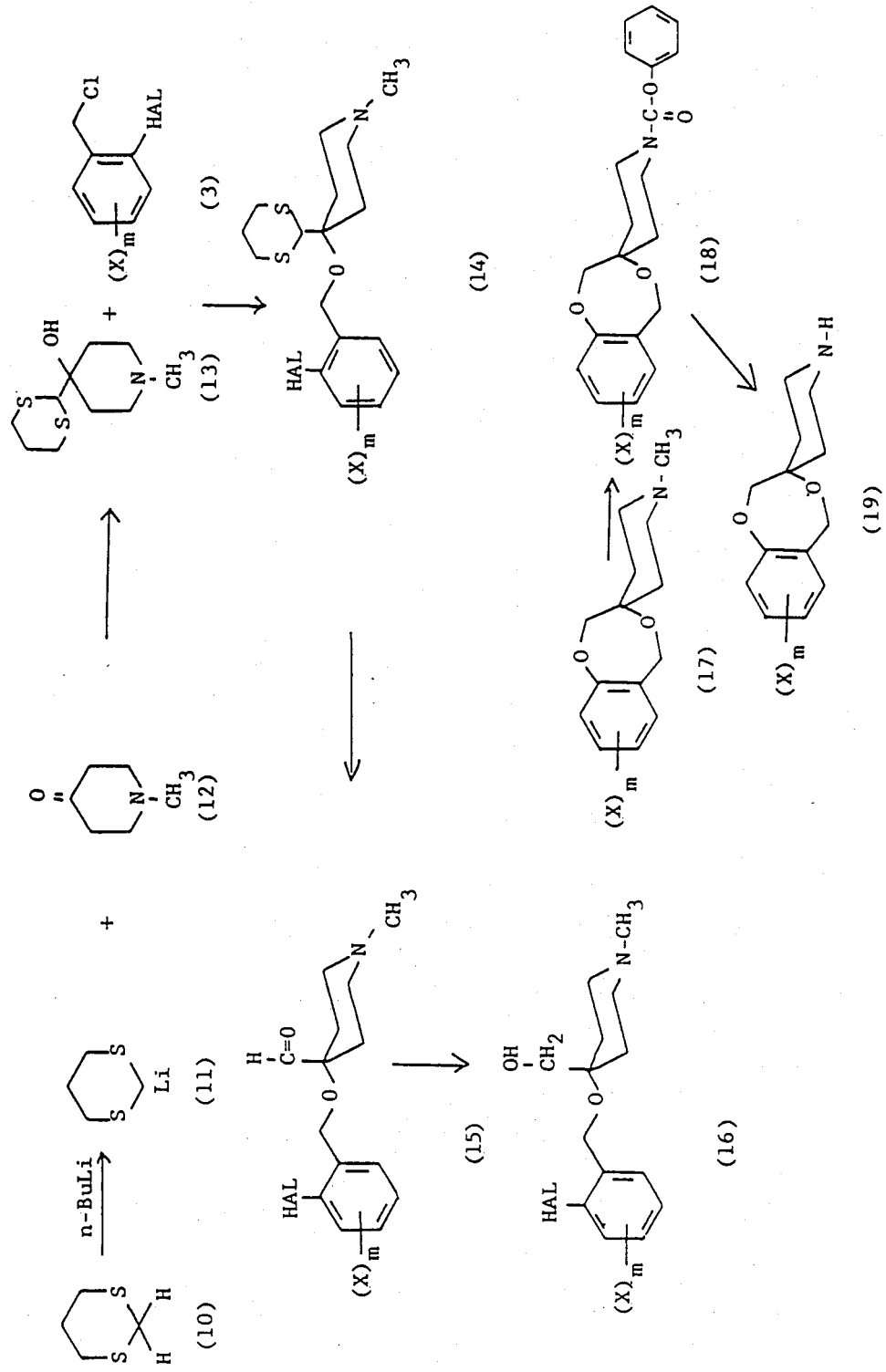

When the substituent $R_3$ is other than hydrogen or $-CH_3$, the $R_3$ substituent is conveniently introduced into the compounds of the invention at an intermediate stage of the synthesis. For example, addition of a Grignard reagent to the aldehyde of formula (15) in FIG. 2 and hydrolysis of the resulting intermediate will form an alcohol analogous to the compound of formula (6). The aldehyde of formula (15) can be synthesized as shown or by other methods known in the art. In addition, other well-known methods for adding alkyl groups to aldehydes and ketones can be employed.

It will be apparent from FIG. 1 that the reaction sequence depicted results in the preparation of compounds of the invention in which the substituent $R_3$ is a methyl group. Corresponding compounds in which $R_3$ is hydrogen can be prepared according to the general reaction scheme depicted in FIG. 2. In this case, 1,3-dithiane of formula (10) is reacted with n-butyllithium to form a lithium salt of formula (11). The lithium salt is then reacted with a commercially available methyl-substituted 4-piperidone of formula (12) in solution in a solvent, such as tetrahydrofuran, to form the alcohol of formula (13). The alcohol (13) is reacted with a substituted or unsubstituted o-halobenzylchloride of formula (3) as previously described. This reaction can be carried out in a solvent, such as tetrahydrofuran, in the presence of a base, such as potassium t-butoxide, to form the compound of formula (14). The aldehyde of formula (15) is formed by reacting the compound of formula (14) with mercuric oxide in the presence of boron trifluoride in solution. The alcohol of formula (16) is prepared from the aldehyde (15) using the technique described in connection with the preparation of the alcohol of formula (6) in FIG. 1.

The alcohol of formula (16) can then be cyclized as previously described to form the compound of formula (17). If the tertiary amino group is converted to a secondary amino group, compounds of the invention containing the substituent $R_1$ can be readily prepared by alkylation of the piperidine nitrogen with substituted alkyl, alkenyl or alkynyl halides or sulfonate esters, as previously described. Conversion to the secondary amino group can be accomplished by reacting the compound of formula (17) with phenylchloroformate to convert the methyl group to a phenoxycarbonyl group as shown in formula (18), which can then be converted to the secondary amine of formula (19) by reaction with aqueous sodium hydroxide in a solvent, such as methanol.

Compounds of formula (II) of the invention can be prepared according to the same procedures described for the compounds of formula (I). In some cases it is necessary to subject the piperidine containing an $R_1^*$ substituent to further processing to obtain the desired substituent. For example, compounds of formula (II) in which $R_1^*$ is a cyanomethyl group can be prepared by reacting the corresponding unsubstituted piperidine of formula (8) with chloroacetonitrile. The cyanomethyl group can then be converted to an aminoethyl group by reduction of the nitrile, such as with $BH_3$. Compounds of formula (II) in which $R_1^*$ is a guanidino ethyl group can then be formed by reacting the aminoethyl-substituted piperdine with S-methyl pseudothiourea in an acidified aqueous alcohol medium.

By a similar reduction of a cyanoethyl-substituted piperidine, such as with lithium aluminum hydride, one can obtain a compound of formula (II) in which $R_1^*$ is an aminopropyl group. The cyanoethyl-substituted piperidine can be formed by cyanoethylation of the unsubstituted piperidine (8) with acrylonitrile.

Compounds of formula (II) in which $R_1^*$ is terminally substituted by a hydroxyl group can be prepared by chemical reduction of the corresponding esters. For example, a hydroxyethyl-substituted piperidine of formula (II) can be prepared from the corresponding ethyl acetate ester by reduction with lithium aluminum hydride.

Alkylation of the unsubstituted piperidine of formula (8) with an alkyl sulfonate can also be employed in forming the compounds of formula (II). For example, compounds in which $R_1^*$ is

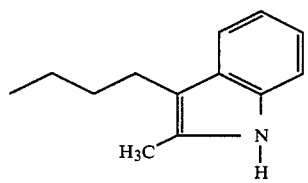

can be prepared by reacting the unsubstituted piperidine of formula (8) with 3-(2-methylindol-3-yl)propyl benzenesulfonate.

Compounds of formula (I) in which $R_1^*$ is —CN can be prepared by reacting the corresponding unsubstituted piperidine of formula (8) with cyanogen bromide. The resulting compound can then be employed to form the corresponding carboximidic acid ester by conversion of the cyano group with an alkali metal alkoxide, such as sodium methoxide or sodium ethoxide. Compounds of formula (I) in which $R_1^*$ is an amide group can be prepared by reacting the unsubstituted piperidine of formula (8) with an organic isocyanate, such as methyl or ethyl isocyanate, according to conventional techniques.

It will be understood that this invention includes the compounds of the invention in all of their stereoisomeric forms, including their enantiomers and diastereomers. This invention also contemplates using mixtures of such forms in the treatment of hypertension in mammals.

It will also be understood that the compounds of the invention and intermediates for their preparation can exist in either the form of a free base or as an acid addition salt. For example, it is often convenient to isolate compounds from reaction mixtures by precipitating them from solution by the addition of an acid having a pharmaceutically acceptable anion. The precipitate can be recovered and purified, and the resulting salt converted to its free base by addition to an alkaline medium.

Compounds of this invention are useful as antihypertensive agents due to their ability to depress blood pressure in mammals. Antihypertensive activity is measured in the spontaneous hypertensive rat by the indirect tail cuff method described by A. Schwartz, Ed., *Methods in Pharmacology*, Vol. page 135, Appleton Century Crafts, New York (1971). In this procedure, a group of five animals is treated orally with the drug for three days in relation to a control group of the same number. The drop in blood pressure is measured on the third day following administration. The antihypertensive activity is expressed as mm Hg decrease in mean arterial blood pressure. Some of the compounds of this invention were tested according to this spontaneous hypertensive rat (SHR) test and were found to produce the results shown in Table I. The dose is indicated as mg of the compound per kg body weight by peroral (PO) administration.

TABLE I

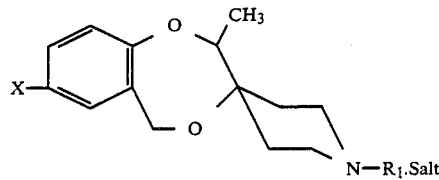

| Compound of Example | Salt | X | R₁ | SHR mm Hg | Dose mg/kg PO |
|---|---|---|---|---|---|
| 36 | $C_2H_2O_4$ | H | H | −42 | 50 |
| 8 | $C_2H_2O_4$ | H | CH₂—CH₂—CH(4-F-C₆H₄)₂ | −102 | 50 |
| 9 | $C_4H_4O_4$ | H | CH₂—CH₂—C(4-F-C₆H₄)(OCH₂CH₂CH₂O) | −34 | 50 |
| 10 | $C_4H_4O_4$ | H | CH₂—CH=C(4-F-C₆H₄)₂ | −18 | 50 |
| 11 | $C_2H_2O_4$ | H | CH₂—CH₂—CH(C₆H₅)₂ | −17 | 50 |
| 12 | $C_4H_4O_4$ | H | CH₂—CH=C(C₆H₅)₂ | −20 | 50 |
| 16 | $C_2H_2O_4$ | Cl | CH₂—CH=C(C₆H₅)₂ | −47 | 50 |
| 17 | $C_2H_2O_4$ | Cl | CH₂—CH₂—CH(C₆H₅)₂ | −84 / −23 | 50 / 3 |
| 14 | HCl | H | CH₂—CH₂—CH₂(4-F-C₆H₄) | −34 | 50 |

TABLE I-continued

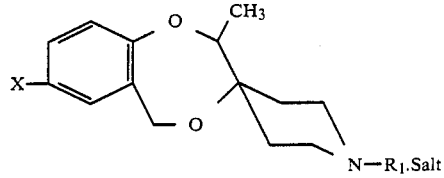

| Compound of Example | Salt | X | R₁ | SHR mm Hg | Dose mg/kg PO |
|---|---|---|---|---|---|
| 18 | $C_2H_2O_4$ | Cl | CH₂—CH₂—CH(4-F-C₆H₄)₂ | −41 | 0.3 |
| 19 | $C_2H_2O_4$ | Cl | CH₂—CH=C(4-F-C₆H₄)₂ | −43 | 10 |
| 23 | | H | CH₂—CH₂—CH(OH)(4-F-C₆H₄) | −31 | 10 |
| 20 | HCl | Cl | CH₂—CH(C₆H₅)₂ | −15 | 50 |
| 24 | $C_2H_2O_4$ | H | CH₂—CH₂—CH(4-F-C₆H₄)(O-4-F-C₆H₄) | −24 | 50 |
| 21 | $C_2H_2O_4$ | Br | CH₂—CH₂—CH(4-F-C₆H₄)₂ | −74 / −63 | 5 / 3 |
| 15 | $C_2H_2O_4$ | H | CH₂—CH₂—CH(4-Cl-C₆H₄)₂ | −27 | 50 |
| 41 | HCl | F | CH₂—CH₂—CH(C₆H₅)₂ | −34 | 50 |

TABLE I-continued

Structure: X-substituted benzene with O-CH(CH3)- and -CH2-O- forming a ring with a piperidine N-R1. Salt.

| Compound of Example | Salt | X | R1 | SHR mm Hg | Dose mg/kg PO |
|---|---|---|---|---|---|
| 42 | HCl | F | —CH2—CH(4-F-phenyl)(4-F-phenyl) | −126 | 50 |

The above data illustrates that compounds of the present invention are useful for the treatment of hypertension when administered to mammals. Compounds of the invention compare favorably with the well-known drug α-methyl dopa which, in a similar test, gives an SHR value of −40 mm Hg when administered at 50 mg/kg PO for five days.

Compounds of this invention produce analgesia when administered to mammals. A phenylquinone-induced writhing test in mice (PQW) was used as an assay to detect analgesia. The procedure employed was a modification of Siegmund, E., Cadmus, R. and Lu, G: *Proc. Soc. Exptl. Bio. Med.*, 95: 729 (1957). 12.5 mg of phenyl-p-benzoquinone were dissolved in 5 ml of 95% ethanol and q.s. to 100 ml with distilled water and administered to mice (10 ml/kg, i.p.). This produces a characteristic "writhe" which is defined as an inward rotation of one or more feet with twisting and turning of the trunk, drawing in of the abdominal wall, lordosis and arching of the back.

A total of 28 male, CD-1 mice (18 to 30 grams) were employed for a time response. Animals recived food and water ad libitum. Drugs to be tested were prepared with distilled water and, if insoluble, one drop of a suitable surfactant was added.

Twenty animals (5/group) were administered the drug 15, 30, 45 and 60 minutes prior to phenylquinone injections. Control animals (2/group) received an equal amount of vehicle. After the administration of phenylquinone the mice were placed separately into one-liter beakers and 5 minutes were allowed to lapse. The mice were then observed for a period of 10 minutes and the number of writhes were recorded for each animal. The formula for computing percent inhibition is:

$$\frac{\bar{x} \text{ Writhes in Control Group} - \bar{x} \text{ Writhes in Drug Group}}{\bar{x} \text{ Writhes in Control Group}} \times 100.$$

The time period with the greatest percent of inhibition is considered the peak time. Compounds less than 65% inhibition are considered to have minimal activity.

A dose range is run in the same fashion as a time response except 10 animals per group were tested at the peak time of drug activity. Fifty animals, 4 drug groups, and a vehicle control were employed. Animals were dosed and tested in a randomized manner. An estimated $ED_{50}$ was calculated by a computer linear regression analysis. The results are reported in Table II.

TABLE II

Structure: X-substituted benzene with O-CH(CH3)- and -CH2-O- forming a ring with piperidine N-R1. Salt.

| Compound of Example | SALT | X | R1 | PQW % | Dose mg/kg SC | SHR mm Hg | Dose mg/kg PO |
|---|---|---|---|---|---|---|---|
| 45 | | H | —CH2CN | −15 | 20 | −29 | 50 |
| 46 | HCl | H | —CH2—phenyl | −87 | 5 | −12 | 50 |
| 48 | | H | —CH2—CH2—OH | −39 | 20 | −23 | 50 |
| 49 | 2C2H2O4 | H | —CH2—CH2—NH2 | −85 | 20 (ED50 = 4.7) | −23 | 50 |
| 50 | ½H2SO4 ½H2O | H | —CH2—CH(NH)—C(=NH2)—NH2 (guanidine) | −8 | 20 | — | — |

TABLE II-continued

| Compound of Example | SALT | X | R₁ | PQW % | Dose mg/kg SC | SHR mm Hg | Dose mg/kg PO |
|---|---|---|---|---|---|---|---|
| 51 | C₂H₂O₄ | H | −CH₂−cyclopropyl | −61 | 10 | — | — |
| 52 | C₄H₄O₄ | H | −CH₂−CH₂−CH₂−C(=N−O−)(6-F-benzisoxazol-3-yl) | −82 | 5 | −67 | 50 |
| 67 | C₂H₂O₄ | H | −CH₂−CH₂−CN | −40 | 20 | −30 | 50 |
| 53 | C₄H₄O₄ | H | −CH₂−CH₂−(2-methyl-1H-indol-3-yl) | −30 | 20 | −32 | 50 |
| 54 | C₂H₂O₄ | H | −C₅H₁₁ | −36 | 20 | — | — |
| 55 | 2C₂H₂O₄ H₂O | H | −CH₂−CH₂−CH₂−NH₂ | −28 | 20 | −28 | 50 |
| 56 | C₂H₂O₄ | H | −CH₂−(4-NO₂-C₆H₄) | −30 | 20 | −17 | 50 |
| 57 | C₄H₄O₄ | H | −CH₂−(4-NH₂-C₆H₄) | −99 | 20 | −12 | 50 |
| 58 | 2HCl | H | −CH₂−N(CH₃)₂ | −6 | 20 | — | — |
| 59 | 2HCl | H | −CH₂−morpholinyl | −52 | 20 | −18 | 50 |
| 61 | HCl | H | −CH₂−C(CN)(C₆H₅)₂ | −25 | 20 | — | — |

TABLE II-continued

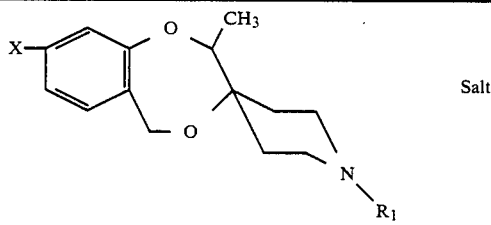

Salt

| Compound of Example | SALT | X | R₁ | PQW % | Dose mg/kg SC | SHR mm Hg | Dose mg/kg PO |
|---|---|---|---|---|---|---|---|
| 65 | C₂H₂O₄ | Cl | H | −98 | 10 | — | — |
| 66 | | Cl | —CH₂—CN | −9 | 20 | — | — |
| Indomethacin | | | | | ED₅₀ = 0.7 PO | | |
| Propoxyphene | | | | | ED₅₀ = 3.9 SC | | |

Still other compounds of this invention produce antihypertensive and/or analgesic effects when administered to mammals as shown in TABLE III.

TABLE III

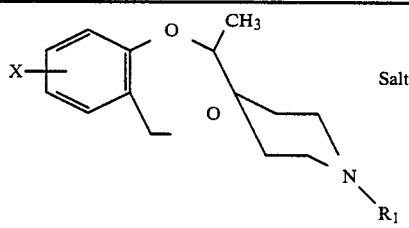

Salt

| Compound of Example | Salt | X | R₁ | PQW % | Dose mg/kg SC | SHR mm Hg | Dose mg/kg PO |
|---|---|---|---|---|---|---|---|
| 81 | HCl | 7-NO₂ | H | −80 | 20 | — | — |
| 80 | — | 7-NO₂ | —COCH₃ | −22 | 20 | −19 | 50 |
| 73 | — | H | —COCH₃ | −27 | 20 | — | — |
| 83 | HCl | 7-NO₂ | —CH₂—CH₂—CH(4-F-C₆H₄)(4-F-C₆H₄) | — | — | −65 | 3 |
| 74 | HCl | 9-Cl | —CH₂—CH₂—CH(C₆H₅)(C₆H₅) | −25 | 20 | — | — |
| 78 | HCl | 7-Cl | —CH₂—CH₂—CH₂—C₆H₄-4-F | −68 (ED₅₀ = 6.8) | 20 | −61 | 50 |
| 77 | HCl | 7-F | —CH₂—CH₂—CH₂—C₆H₄-4-F | −66 (ED₅₀ = 4.3) | 5 | −40 | 50 |

TABLE III-continued

[Structure: X-substituted benzene ring with -O-CH(CH₃)- linked to a piperidine ring (via O at 4-position) bearing N-R₁; Salt]

| Compound of Example | Salt | X | R₁ | PQW % | Dose mg/kg SC | SHR mm Hg | Dose mg/kg PO |
|---|---|---|---|---|---|---|---|
| 79 | HCl | 7-Cl | —CH₂—CH₂—CH(2-F-C₆H₄)(2-F-C₆H₄) | −91 | 20 | −27 | 0.3 |
| 76 | HCl | 7-F | —CH₂—CH₂—CH(2-F-C₆H₄)(2-F-C₆H₄) | −38 | 20 | −31 | 0.3 |
| 85 | HCL | 7-Cl | —CH₂—O—CH(4-F-C₆H₄)(4-F-C₆H₄) | −44 | 20 | −46 | 50 |
| 84 | HCl | H | —CH₂—(CH₂)₂—CH(4-F-C₆H₄)(4-F-C₆H₄) | −34 | 20 | — | — |
| 86 | HCl | 7-Cl | —CH₂—(CH₂)₂—CH(4-F-C₆H₄)(4-F-C₆H₄) | −25 | 20 | −42 | 50 |

TABLE III-continued

Structure: X—(phenyl)—O—CH(CH₃)—(piperidine-4-yl-O)—N—R₁ ; Salt

| Compound of Example | Salt | X | R₁ | PQW % | Dose mg/kg SC | SHR mm Hg | Dose mg/kg PO |
|---|---|---|---|---|---|---|---|
| 82 | HCl | 7-Cl | —CH(4-F-C₆H₄)₂ | −30 | 20 | — | — |
| 87 | HCl | 7-Cl | —CH₂CH₂CH(cyclohexyl)₂ | — | — | −69 | 50 |
| 69 | HCl | H | —C(=NH)OCH₃ | −74 | 20 | — | — |
| 70 | — | H | —C(=O)NHCH₃ | −35 | 20 | −39 | 50 |
| 71 | — | H | —C(=O)NHCH₂CH₃ | −46 | 20 | −67 | 50 |
| 72 | HCl | H | —C(=NH)OCH₂CH₃ | −51 | 20 | −20 | 50 |
| 88 | HCl | H | —CH₂—CH(OH)—CH₂—O—C₆H₅ | −99 | 20 | −34 | 50 |
| 89 | HCl | H | —CH₂—CH(OH)—CH₂—O—C₆H₄—OCH₃ | −57 | 20 | −40 | 50 |
| 90 | HCl | H | —CH₂—CH(OH)—CH₂—O—C₆H₄—F | −99 | 20 | — | — |
| 91 | HCl | 7-Cl | —CH₂—CH(OH)—CH₂—O—C₆H₅ | −67 | 20 | −29 | 50 |

TABLE III-continued

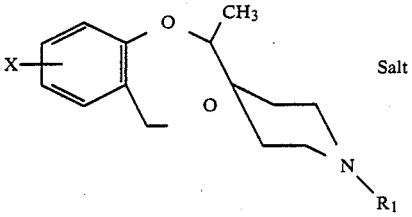

| Compound of Example | Salt | X | R₁ | PQW % | Dose mg/kg SC | SHR mm Hg | Dose mg/kg PO |
| --- | --- | --- | --- | --- | --- | --- | --- |
| 92 | HCl | 7-Cl | —CH₂—CH(OH)—CH₂—O—C₆H₄—OCH₃ | −47 | 20 | −66 | 50 |
| 93 | HCl | 7-Cl | —CH₂—CH(OH)—CH₂—O—C₆H₄—F | −88 | 20 | −24 | 50 |

Typically, the dose of the compounds of the invention will be from about 0.1 to about 50 mg/kg of body weight per day.

The compounds of the present invention may be administered in a pharmaceutically effective amount to a subject by a convenient route, such as orally, intramuscularly, intravenously, subcutaneously or intraperitoneally. The preferred route of administration is oral, for example, with an inert diluent or with an edible carrier or in gelatin capsules or tablets.

For the purpose of oral therapeutic administration, the active compounds of this invention may be incorporated with excipients and used in the form of tablets, troches, capsules, exilirs, suspensions, syrups, wafers, chewing gum and the like. These preparations should contain at least about 0.5% by weight of active compound, but the amount of active ingredient may be varied depending on the particular form and may typically be between about 7 to about 70% by weight of the unit. The amount of active compound in such compositions is such that a suitable dosage will be obtained. Preferred compositions in preparations according to the present invention are prepared so that an oral dosage unit form contains between about 1 and about 200 mg of active compound.

The tablets, pills, capsules, troches and the like may also contain the following adjuvants: a binder, such as gum tragacanth or gelatin; an excipient, such as starch or lactose; a disintegrating agent, such as algenic acid, potato starch and the like; a lubricant such as magnesium stearate; a sweetening agent, such as sucrose or saccharine, or a flavoring agent, such as peppermint, methylsalicylate or orange flavoring. When the dosage unit form is a capsule, it may contain in addition to materials of the above type, a liquid carrier, such as a fatty oil. Other dosage unit forms may contain various other materials that modify the physical form of the dosage unit, for example, coatings. Thus, tablets or pills may be coated with sugar, shellac, or both, A syrup may contain, in addition to the active compounds, sucrose as a sweetening agent, preservatives, colorings, and flavors. Materials employed in preparing these various compositions must be pharmaceutically pure and nontoxic in the amounts utilized.

For the purpose of parenteral therapeutic administration, the active compounds of the invention may be incorporated into a solution or suspension. These preparations should contain at least about 0.1% by weight of active compound, but may be varied to typically contain about 0.5 to about 30% of the weight thereof. The amount of active compound in such compositions is such that a suitable dosage will be obtained. Preferred compositions in preparations according to the present invention are prepared so that a parenteral dosage unit contains between about 0.5 to about 100 mg of active compound.

The solutions or suspensions may also include the following components: a sterile diluent, such as water, for injection, saline solution, fixed oils, polyethylene glycols, glycerine, propylene glycol or other synthetic solvents; antibacterial agents, such as benzyl alcohol or methyl paraben; antioxidants, such as ascorbic acid or sodium bisulfite; chelating agents, such as ethylenediamine tetraacetic acid; buffers, such as acetates, citrates, or phosphates; and agents for the adjustment of tonicity, such as sodium chloride or dextrose. Parenteral preparations can be enclosed in ampules, disposable syringes or multiple dose vials made of glass or plastic.

The compounds of the invention, while effective in themselves, may be formulated and administered in the form of their pharmaceutically acceptable addition salts for purposes of stability, convenience of crystallization, increased solubility and the like. Such salts include the salts of inorganic acids, such as hydrochloric acid, hydrobromic acid, sulfuric acid and nitric acid. Salts of organic acids, such as citric, fumaric, maleic and tartaric acids, can also be employed.

This invention will now be described in greater detail in the following Examples.

EXAMPLE 1

1-Acetyl-4-ethynyl-4-piperidinol

To 350 ml of liquid ammonia was added 0.06 g of ferric nitrate. When the ferric nitrate dissolved, 1.0 g of sodium was added. The mixture was stirred until a black precipitate formed. To the mixture was then added 3.25 g of sodium. The solution was stirred until the mixture turned gray after which acetylene was bubbled through the reaction for 2 hrs. To the mixture was then added 25 g (0.177 mol) of N-acetyl-4-piperidone in 100 ml of dry THF. The mixture was subsequently stirred for 3 hrs. during which time acetylene was bubbled through. The reaction was then quenched by addition of 10 g (0.187 mol) of ammonium chloride. The ammonia was allowed to evaporate overnight. To the mixture was then added 75 ml of saturated ammonium nitrate and 40 ml of 25% ammonium hydroxide. The mixture was then extracted twice with chloroform, dried over potassium carbonate, filtered and the solvent evaporated to provide a white solid. The solid was washed with anhydrous ether and dried. The crude yield of 1-acetyl-4-ethynyl-4-piperidinol was 17.9 g (0.107 mol, 60.6%). Recrystallization from ethyl acetate provided analytically pure material, m.p. 132°–134° C. The material appeared pure by TLC (silica; 2% methanol/chloroform), $R_f=0.2$; (silica; 10% methanol/dichloromethane), $R_f=0.4$, IR (chloroform), $^1$H-NMR (CDCl$_3$) and MS (MH$^+$ = 168) are consistent with the assigned structure.

ANALYSIS: Calculated for C$_9$H$_{13}$NO$_6$: 64.65%C, 7.83%H, 8.38%N. Found: 64.38%C, 7.81%H, 8.40%N.

EXAMPLE 2

1-Acetyl-4-ethynyl-4-(2-fluorophenylmethoxy)piperidine

Sodium hydride (39.98 g as a 50% mineral oil suspension, 883 mmole) was suspended in dry DMF (500 ml). 1-Acetyl-4-ethynyl-4-hydroxypiperidine (126.5 g; 758 mmole), dissolved in 500 ml of DMF, was added dropwise to the sodium hydride suspension at such a rate as to maintain the solvent temperature below 30° C. After evolution of hydrogen had ceased, 2-fluorobenzylchloride (120.8 g; 99 ml; 833 mmole), dissolved in 200 ml of DMF, was added dropwise, maintaining the temperature below 25° C. After allowing the mixture to react for 3 hours, 2 l. of water was added to quench the reaction. The mixture was extracted with ether and the combined ether extracts were back extracted with 5% hydrochloric acid. The organic phase was finally extracted with saturated aqueous sodium chloride and dried over anhydrous potassium carbonate. The mixture was filtered and the volatile components removed in vacuo. A residue of material, slightly impure by TLC, remained (193 g; 700 mmole; 84.3%). A 10 g sample was purified by preparative high performance liquid chromatography (HPLC) using hexane:ethylacetate (2:1) and finally ethylacetate as the effluents on silica gel. The residue was an oil which crystallized upon standing. Recovery was 7 g of material which appeared pure by TLC on silica gel in hexane:ethylacetate (2:1), $R_f=0.1$ and in chloroform:methanol (9:1), $R_f=0.6$. MS (ci MH$^+$ = 276), NMR-CDCl$_3$ and IR-CHCl$_3$ are consistent with the structure, m.p. = 59°–62° C.

ANALYSIS: Calculated for C$_{16}$H$_{18}$FNO$_2$: 69.79%C, 6.60%H, 5.09%N. Found: 69.72%C, 6.56%H, 4.88%N.

EXAMPLE 3

4-(1-Oxoethyl)-4-(2-fluorophenylmethoxy)piperidine oxalate

The compound 1-acetyl-4-ethynyl-4-(2-fluorophenylmethoxy)piperidine (262 g; 950 mmole) was dissolved in 1600 ml of methanol:water (1:1) in a 3-necked round bottomed flask equipped with mechanical stirrer, thermometer, reflux condenser and nitrogen line. A solution of 180 ml of concentrated sulfuric acid dissolved in 200 ml of water was added to the stirred solution. The mixture was heated to reflux and stirred at that temperature for 3 hrs. Hydrolysis of the acetyl function was monitored by infra-red spectra of aliquots of the reaction. The reaction mixture was cooled and 73 g of mercuric sulfate was added and the temperature was raised to reflux again. Hydrolysis to the ketone was monitored by infra-red spectra as well. After 3 hrs, at reflux, the reaction was determined to be complete. The mixture was cooled and filtered. The filtrate was made basic (pH = 8.5) with 50% sodium hydroxide and was extracted several times with chloroform. The organic layer was dried over anhydrous magnesium sulfate and filtered. The solvent was removed under vacuum and the residue was chromatographed on 500 g of alumina packed in ether. The compound was eluted with ether:ethanol (1:1) with the collection of 125 ml fractions. Those containing the material (6–24) were combined and the oxalate salt was precipitated, which was filtered, washed with anhydrous ether and dried (42 g, 123 mmole, 13% yield). A 7 g sample was recrystallized from ethanol resulting in 2 g of 4-(1-oxoethyl)-4-(2-fluorophenylmethoxy)piperidine oxalate in the first crop. This material appeared pure by thin layer chromatography on silica gel in chloroform:methanol (9:1), $R_f=0.30$ and hexane:THF (1:1), $R_f=0.10$. MS (ci MH$^+$ = 252), NMR-DMSO-d$_6$ and IR-KBr are consistent with the structure, m.p. = 154°–155° C.

ANALYSIS: Calculated for C$_{16}$H$_{20}$FNO$_6$: 56.79%C, 5.92%H, 4.10%N. Found: 56.60%C, 5.81%H, 4.01%N.

EXAMPLE 4

4-(1-Hydroxyethyl)-4-(2-fluorophenylmethoxy)piperidine oxalate

The compound 4-(1-oxoethyl)-4-(2-fluorophenylmethoxy)piperidine oxalate (10.00 g, 29.00 mmole) was converted to its free base with saturated aqueous sodium bicarbonate and extracted into chloroform. The organic layer was dried over anhydrous magnesium sulfate, filtered and the chloroform was removed in vacuo. The residue was dissolved in 20 ml of methanol and added dropwise to a suspension of 2.76 g of sodiumborohydride (73.00 mmole) in 30 ml of methanol. This was maintained at 20° C. (using an ice bath) and was allowed to react overnight at ambient temperature under nitrogen. The reaction was quenched with 5 ml of 10% hydrochloric acid. After being stirred for 1 hr., the solvent was removed under vacuum and the solid residue was dissolved in water. The solution was made basic (pH = 10) with saturated, aqueous sodium bicarbonate and the mixture was extracted with chloroform. After drying over anhydrous magnesium sulfate, the chloroform solution was filtered, diluted with an equal volume of anhydrous ether and the product precipitated as its oxalate salt. The precipitate was recrystallized from 2-propanol resulting in 2.90 g of 4-(1-hydroxyethyl)-4-(2-fluorophenylmethoxy)piperidine oxalate (8.50 mmole, 28.15%) in the first crop. This material appeared pure by thin layer chromatography on silica gel in chloroform:methanol (1:1), $R_f=0.1$ and 2-propanol:ammonium hydroxide (7:3) $R_f=0.7$. MS (ci MH$^+$ = 254), NMR-DMSOd$_6$ and IR-KBr are consistent with the structure, m.p. = 145°–150° C.

ANALYSIS: Calculated for C$_{16}$H$_{22}$FNO$_6$: 55.96%C, 6.47%H, 4.08%N. Found: 56.15%C, 6.38%H, 4.13%N.

EXAMPLE 5

2-Methyl spiro[2H-1,4-benzodioxepin-3(5H)4'-piperidine]hydrochloride

The compound 4-(1-hydroxyethyl)-4-(2-fluorophenylmethoxy)piperidine oxalate (55.4 g, 0.162 mole) was converted to its free base and was extracted into chloroform. The combined extracts were loaded onto a 500 g alumina column packed in diethyl ether. Final elution with diethyl ether:ethanol (1:1), removal of all solvents and trituration with hexane afforded 33 g (0.130 mole) solids after vacuum drying. Recovery=80.5%. The solids were dissolved in 290 ml dimethyl sulfoxide (DMSO). A second mixture was prepared by suspending a hexane-washed 50% mineral oil dispersion of NaH (6.6 g, 0.137 mole) in 340 ml dry DMSO. The second mixture was heated to 60°–70° C. for 1 hr. When evolution of hydrogen ceased, the mixture was cooled to 25° C. and the first solution added dropwise thereto while maintaining the temperature at about 25° C. When addition was complete, the mixture was heated to 70° C. for 1 hr. GLC showed the reaction to be substantially complete. The reaction mixture was quenched with $K_2CO_3/H_2O$ and extracted with diethyl ether. The extract was dried, and the hydrochloride salt was precipitated and dried at 50° C. in vacuo. Yield=32.2 g (0.12 mol), 91.9%.

EXAMPLE 6

7-Chloro-2-methylspiro[2H-1,4-benzodioxepin-3(5H)4'-piperidine]hydrochloride The compound 2-methylspiro[2H-1,4-benzodioxepin-3(5H)4'-piperidine]hydrochloride (0.57 g, 2.12 mmole) was dissolved in 20 ml methanol and stirred with 0.32 g of N-chlorosuccinimide (2.33 mmole). The mixture was heated at reflux for 45 min. after which the reaction was determined to be 98% complete by GLC (3% ASI, 200° C. flow=45 ml/min). The volume of methanol was reduced by distillation and upon cooling the product crystallized. The reaction yielded 0.47 g of 7-chloro-2-methylspiro[2H-1,4-benzodioxepin-3(5H)4'-piperidine]hydrochloride (1.55 mmole, 73.11%) which appeared pure by TLC on silica gel in 2-propanol:ammonium hydroxide (10:1), $R_f=0.4$ and in chloroform:methanol (1:1), $R_f=0.1$. MS (ci MH+ =268), NMR-DMSO-$d_6$, CMR-DMSO-$d_6$ and IR-KBr are consistent with the structure, m.p. 274°–276° C., d.

ANALYSIS: Calculated for $C_{14}H_{19}ClNO_6$: 55.27%C, 6.31%H, 4.60%N. Found: 54.94%C, 6.24%H, 4.54%N.

EXAMPLE 7

7-Bromo-2-methylspiro[2H-1,4-benzodioxepin-3(5H)4'-piperidine]hydrochloride

The compound 2-methylspiro[2H-1,4-benzodioxepin-3(5H)4'-piperidine]hydrochloride (3.4 g, 12.64 mmole) was dissolved in 200 ml of methanol along with 2.47 g of NBS (13.9 mmole). The mixture was allowed to react for 45 min. after which time reaction was determined to be complete by GLC (OV 225, 200° C., 30 ml/min, $t_R=4.52$). The methanol was removed in vacuo and the residue was suspended in saturated aqueous $Na_2CO_3$. The products were extracted with chloroform and upon removal of solvent, in vacuo, there resulted a solid material. The solid was dissolved in ether and the hydrochloride salt precipitated. The material was recrystallized from methanol resulting in 2.5 g of 7-bromo-2-methylspiro[2H-1,4-benzodioxepin-3(5H)4'-piperidine]hydrochloride which appeared pure by TLC on silica gel in 2-propanol:ammonium hydroxide (9:1), $R_f=0.4$ and in chloroform:methanol (1:1), $R_f=0.1$. Mass Spec (M+ =311, 313; 1/1), NMR-DMSO-$d_6$ and IR-KBr are consistent with the structure, m.p.=290°–293° C., d.

ANALYSIS: Calculated for $C_{14}H_{19}BrClNO_2$: 48.22%C, 5.50%H, 4.02%N. Found: 48.13%C, 5.52%H, 3.99%N.

EXAMPLE 8

1'-[4,4-Bis-(4-fluorophenyl)butyl]-2-methylspiro[2H-1,4-benzodioxepin-3(5H)4'-piperidine]oxalate The compound 2-methylspiro[2H-1,4-benzodioxepin-3(5H)4'-piperidine]oxalate (3.9 g, 12.2 mmole) was converted to its free base and was extracted into chloroform. The combined extracts were dried over magnesium sulfate and were filtered. The filtrate was reduced in volume in vacuo. The residue was dissolved in 25 ml of DMF and was stirred with 2.6 g of 4,4-bis-(4-fluorophenyl)butylchloride (13.4 mmole). To the resultant mixture was added 2.5 g of milled anhydrous potassium carbonate and 16 mg of potassium iodide. The mixture was heated at 100° C. for 6 hr., after which time the reaction was determined complete by TLC. The mixture was cooled to ambient temperature and quenched with 100 ml water. The products were extracted with ether and the solvent was removed in vacuo. The residue was loaded onto an 80 g alumina column packed in ether. The products were eluted in 30 ml fractions. The desired compound was found in fraction numbers 2 and 3. The fractions were combined and the oxalate salt was precipitated, yielding 3.0 g (5.28 mmole 43.32%) of 1'-[4,4-bis-(4-fluorophenyl)butyl]-2-methylspiro[2H-1,4-benzodioxepin-3(5H)4'-piperidine]oxalate. The products were recrystallized from 2-propanol/methanol resulting in a crystalline material which appeared pure by TLC on silica gel in chloroform:methanol (9:1), $R_f=0.7$ and in dichloromethane:2-propanol, $R_f=0.4$. Mass Spec (ci MH+ =478), NMR-DMSO-$d_6$ and IR-KBr are consistent with the structure, m.p.=213°–214° C. (d).

ANALYSIS: Calculated for $C_{32}H_{35}F_2NO_6$: 67.70%C, 6.23%H, 2.47%N. Found: 67.51%C, 6.18%H, 2.29%N.

EXAMPLE 9

2-Methyl-1'-[3-[2-(4-fluorophenyl)-1,3-dioxolan-2yl]propyl]spiro[2H-1,4-benzodioxepin-3(5H)4'-piperidine]maleate The compound 2-methylspiro[2H-1,4-benzodioxepin-3(5H)4'-piperidine]oxalate (5 g, 15.5 mmole) was converted to its free base and dried. The residue was dissolved in 50 ml of DMF and stirred with 4.2 g of γ-chloro-4-fluorobutyrophenone ethylene ketal (17.1 mmole), 5 g of potassium carbonate (anhydrous, milled) and 25 mg of potassium iodide. The mixture was heated to 100° C. under $N_2$ for 2 hrs. The reaction was determined complete by TLC. After cooling to ambient temperature, the mixture was quenched with water and was extracted with ether. The organic layers were combined and back extracted with saturated brine. The solvent was removed in vacuo and the residue loaded onto a 100 g alumina column packed in ether. Fractions of 50 ml of ether were eluted and the desired material was found in numbers 2–4. These fractions were combined and the maleate salt was precipitated. The solids were recrystallized from 2-propanol yielding 3.1 g of 2-methyl-1′-[3-[2-(4-fluorophenyl)-1,3-dioxalan-2-yl]propyl]spiro[2H-1,4-benzodioxepin-3(5H)4′-piperidine]maleate (5.6 mmole, 36%) which appeared pure by TLC on silica gel in chloroform:methanol (9:1), $R_f=0.4$ and in dichloromethane:2-propanol (1:1), $R_f=0.5$. MS (ci MH+=442), NMR-DMSO-$d_6$ and IR-KBr are consistent with the structure, m.p.=154°–156° C.

ANALYSIS: Calculated for $C_{30}H_{36}FNO_8$: 64.61%C, 6.52%H, 2.51%N. Found: 64.39%C, 6.45%H, 2.57%N.

EXAMPLE 10

1′-[4,4-Bis(4-fluorophenyl)-3-butenyl]-2-methyl-spiro[2H-1,4-benzodioxepin-3(5H)4′-piperidine]maleate The compound 2-methylspiro[2H-1,4-benzodioxepin-3(5H)4′-piperidine]oxalate (5 g, 15.5 mmole) was converted to its free base and dried. The residue was dissolved in 50 ml of DMF and stirred with 4.8 g of 4,4-bis(4-fluorophenyl)-1-chloro-3-butene, 5 g of $K_2CO_3$ (anhydrous, milled) and 25 mg of potassium iodide under nitrogen. The mixture was quenched with water and extracted with ether. The ether extracts were combined and washed with saturated brine. The ether was removed in vacuo and the residue was loaded onto a 100 g alumina column packed in ether. Fractions of 50 ml of ether were eluted and the desired material found in maleate salt was precipitated. The material was washed with ether, filtered and vacuum dried, resulting in 2 g of 1′-[4,4-bis-(4-fluorophenyl)-3-butenyl]-2-methylspiro[2H-1,4-benzodioxepin-3-(5H)4′-piperidine]maleate (3.38 mole, 21.81%). This material appeared pure by TLC on silica gel in chloroform:methanol (9:1), $R_f=0.5$ and in dichloromethane:2-propanol (1:1), $R_f=0.8$. MS (ci MH+=476), NMR-CDCl$_3$ and IR-CHCl$_3$ are consistent with the structure, m.p.=144°–149° C.(d).

ANALYSIS: Calculated for $C_{34}H_{35}F_2NO_6$: 69.01%C, 5.97%H, 2.37%N. Found: 68.67%C, 5.83%H, 2.44%N.

EXAMPLE 11

1′-(4,4-Diphenylbutyl)-2-methylspiro[2H-1,4-benzodioxepin-3(5H)4′-piperidine]oxalate The compound 2-methylspiro[2H-1,4-benzodioxepin-3(5H)4′-piperidine]hydrochloride (5 g, 18.55 mmole) was converted to its free base and dried. The oil was dissolved in 50 ml of DMF and stirred under nitrogen with 15 mg of potassium iodide, 5 g of potassium carbonate (milled, anhydrous) and 4.99 g of 4,4-diphenylbutylchloride (20.4 mmole) at ambient temperature, overnight. The reaction was determined to be complete by TLC. The mixture was quenched with water and extracted with ether. The solvent was removed in vacuo and the residue was loaded onto a 100 g alumina column packed in either. Fractions of 50 ml were eluted and the desired material was found in numbers 2–5, which were combined. The oxalate salt was precipitated and recrystallized from 2-propanol/methanol. The resultant product, 2.4 g of 1′-[4,4-diphenylbutyl]-2-methylspiro[2H-1,4-benzodioxepin-3(5H)4′-piperidine]oxalate (4.52 mmole, 24.3%), appeared pure by TLC on silica gel in chloroform:methanol (9:1), $R_f=0.5$ and in dichloromethane:2-propanol (1:1), $R_f=0.4$. MS (17 ev; M+=441), NMR-DMSO-$d_6$ and IR-KBr are consistent with the structure, m.p. 192°–194° C.

ANALYSIS: Calculated for $C_{32}H_{37}NO_6$: 72.28%C, 7.03%H, 2.63%N. Found: 72.06%C, 7.03%H, 2.42%N.

EXAMPLE 12

1′-[4,4-Diphenyl-3-butenyl]-2-methylspiro[2H-1,4-benzodioxepin-3(5H)4′-piperidine]maleate The compound 2-methylspiro[2H-1,4-benzodioxepin-3(5H)4′-piperidine]hydrochloride (5 g, 18.6 mmole) was converted to its free base and dried. The resultant oil was dissolved in 50 ml of DMF and stirred with 5 g of potassium carbonate (milled, anhydrous), 15 mg of potassium iodide and 4.95 g of 4,4-diphenyl-3-butenyl chloride (20.4 mmole) for 2 days at ambient temperature under nitrogen. The reaction was determined to be complete by TLC and quenched with an equal volume of water. The products were extracted with ether and the combined extracts reduced in volume in vacuo. The remaining oil was loaded onto a 100 g alumina column packed in ether. Elution of 50 ml fractions resulted in the desired products being found in numbers 2–4. These fractions were combined and the maleate salt was precipitated. The solids were recrystallized from 2-propanol/methanol yielding 2.0 g of 1′-[4,4-diphenyl-3-butenyl]-2-methylspiro[2H-1,4-benzodioxepin-3(5H)4′-piperidine]maleate (3.6 mmole, 19.4%). This material appeared pure by TLC on silica gel in chloroform:methanol (9:1), $R_f=0.6$ and in dichloromethane:2-propanol (1:1), $R_f=0.8$. MS (ci MH+=440), NMR-DMSO-$d_6$ and IR-KBr are consistent with the structure, m.p. 170°–171° C.

ANALYSIS: Calculated for $C_{34}H_{37}NO_6$: 73.48%C, 6.72%H, 2.52%N. Found: 73.38%C, 6.70%H, 2.56%N.

EXAMPLE 13

2-Methyl-1′-[3,3-diphenylpropyl]spiro[2H-1,4-dibenzodioxepin-3(5H)4′-piperidine]oxalate The compound 2-methylspiro[2H-1,4-benzodioxepin-3(5H)4′-piperidine]hydrochloride (5 g, 18.6 mmole) was dissolved in 100 ml of DMF and stirred along with 5 g of potassium carbonate (milled, anhydrous), 15 mg of potassium iodide and 4.7 g of 3,3-diphenylpropylchloride (20.41 mmole). The mixture was heated to 90° C. for 3 hrs. under nitrogen after which the reaction was determined to be complete by TLC. The reaction was quenched with water and extracted with ether. The extracts were combined, reduced in volume under vacuum and loaded onto a 100 g alumina column packed in ether. Fractions of 50 ml were collected and the desired product was found in numbers 2–5. These fractions were combined, after which the oxalate salt was precipitated. The solids were recrystallized from 2-propanol resulting in 2.6 g of 2-methyl-1′-[3,3-diphenylpropyl]-spiro[2H-1,4-benzodioxepin-3(5H)4′-piperidine]oxalate (6.6 mmole, 35.42%) which appeared pure on TLC in chloroform:methanol (9:1), $R_f=0.6$ and in dichloromethane:2-propanol (1:1), $R_f=0.5$, m.p.=178°–182° C. MS (ci MH+=428), NMR-DMSO-$d_6$ and IR-KBr are consistent with the structure.

ANALYSIS: Calculated for $C_{31}H_{35}NO_6$: 71.92%C, 6.83%H, 2.70%N. Found: 72.09%C, 6.78%H, 3.16%N.

EXAMPLE 14

1'-[4-(4-Fluorophenyl)butyl]-2-methylspiro[2H-1,4-benzodioxepin-3(5H)4'-piperidine]hydrochloride The compound 2-methylspiro[2H-1,4-benzodioxepin-3(5H)4'-piperidine]hydrochloride (5 g, 18.6 mmole) was dissolved in 100 ml of DMF and stirred under nitrogen at 90° C. with 5 g of potassium carbonate (milled, anhydrous), 15 mg of potassium iodide, and 3.80 g of 4-(4-fluorophenyl)butyl chloride (20.4 mmole) overnight. The reaction was determined to be complete by TLC. The mixture was cooled to ambient temperature, quenched with water and extracted into ether. The ether extracts were backwashed with saturated brine and the solvent was removed under vacuum. The residue was loaded onto a 100 g alumina column packed in ether and 50 ml fractions were eluted. The desired material was found in fractions 2-4, which were subsequently combined. The hydrochloride was precipitated and recrystallized from methanol-water resulting in 2.4 g of 1'-[4-(4-fluorophenyl)butyl]-2-methylspiro[2H-1,4-benzodioxepin-3(5H)4'-piperidine]hydrochloride (5.7 mmole, 30.78%) which appeared pure by TLC on silica gel in chloroform:methanol (9:1), $R_f=0.8$, and in dichloromethane:2-propanol (1:1), $R_f=0.7$. MS (MH+ =384), NMR-DMSO-$d_6$ and IR-KBr are consistent with the structure, m.p.=212°-213° C.

ANALYSIS: Calculated for $C_{24}H_{31}ClFNO_2$: 68.63%C, 7.45%H, 3.33%N. Found: 68.67%C, 7.49%H, 3.65%N.

EXAMPLE 15

1'-[4,4-Bis(4-chlorophenyl)butyl]-2-methylspiro[2H-1,4-benzodioxepin-3(5H)4'-piperidine]oxalate The compound 2-methylspiro[2H-1,4-benzodioxepin-3(5H)4'-piperidine]hydrochloride (4.0 g, 15.0 mmole) was dissolved in 150 ml of DMF. To the solution was added 4 g of potassium carbonate (milled, anhydrous), 15 mg of potassium iodide, and 5.12 g of 4,4-bis(4-chlorophenyl)butylchloride (15.0 mmole). The reaction mixture was stirred at 80° C., under nitrogen, overnight. The reaction was determined to be complete by TLC. The mixture was quenched with an equal volume of water and extracted with ether. The ether extracts were combined, backwashed with saturated brine and the solvent was removed under vacuum. The residue was loaded onto a 100 g alumina column packed into ether. Fractions of 50 ml were eluted and the desired product was found in numbers 3-5. These fractions were combined and the oxalate salt was precipitated. The solids were recrystallized from toluene-ethanol yielding 2.1 g of 1'-[4,4-bis(4-chlorophenyl)butyl]-2-methylspiro[2H-1,4-benzodioxepin-3(5H)4'-piperidine]oxalate (3.50 mmole, 23.3%). This material appeared pure by TLC on silica gel on chloroform:methanol (9:1), $R_f=0.5$ and in dichloromethane:2-propanol (1:1), $R_f=0.4$. MS (ci MH+ =510) and in dichloro- and IR-KBr are consistent with the structure, m.p. 192°-195° C.

ANALYSIS: Calculated for $C_{32}H_{35}Cl_2NO_6$: 63.99%C, 5.89%H, 2.33%N. Found: 63.68%C, 5.94%H, 2.25%N.

EXAMPLE 16

1'-[4,4-Diphenyl-3-butenyl]-7-chloro-2-methylspiro[2H-1,4-benzodioxepin-3(5H)4'-piperidine]oxalate The compound 7-chloro-2-methylspiro[2H-1,4-benzodioxepin-3(5H)4'-piperidine]hydrochloride (5 g, 16.5 mmole), 5 g of potassium carbonate (milled, anhydrous), 15 mg of potassium iodide and 4.39 g of 4,4-diphenyl-3-butenylchloride (18.1 mmole) were combined in 50 ml of DMF and stirred at 90° C. for 2 hr under nitrogen. The reaction was determined to be completely by TLC, after which time it was quenched with water and extracted with ether. The ether extracts were combined and the solvent was removed under vacuum. The residue was loaded onto a 100 g alumina column packed in ether. Fractions of 50 ml of ether were collected and the desired material was found in numbers 2-4. Combination of these fractions was followed by precipitation of the oxalate salt. The solids were recrystallized from 2-propanol/methanol resulting in 2 g of 1'-[4,4-diphenyl-3-butenyl]-7-chloro-2-methylspiro[2H-1,4-benzodioxepin-3(5H)4'-piperidine]oxalate (3.6 mmole, 21.6%) which appeared pure by TLC on silica gel in chloroform:methanol (9:1), $R_f=0.5$ and in dichloromethane:2-propanol (1:1), $R_f=0.4$. MS (ci MH+ =474), NMR-DMSO-$d_6$ and IR-KBr are consistent with the structure, m.p.=214°-215° C.

ANALYSIS: Calculated for $C_{32}H_{34}ClNO_6$: 68.13%C, 6.09%H, 2.48%N. Found: 67.95%C, 6.05%H, 2.45%N.

EXAMPLE 17

1'-[4,4-Diphenylbutyl]-7-chloro-2-methylspiro[2H-1,4-benzodioxepin-3(5H)4'-piperidine]oxalate The compound 7-chloro-2-methylspiro[2H-1,4-benzodioxepin-3(5H)4'-piperidine]hydrochloride (5 g, 16.5 mmole), 5 g of potassium carbonate (milled, anhydrous), 15 mg of potassium iodide and 4.43 g of 4,4-diphenylbutyl chloride (18.1 mmole) were combined in 50 ml of DMF. This mixture was stirred at 90° C. for 2 hr. under nitrogen. The reaction was determined to be complete by TLC, after which time it was quenched with water and extracted with ether. The ether extracts were combined and the solvent was removed under vacuum. The residue was loaded onto a 100 g alumina column packed in ether. Fractions of 50 ml were collected and the desired material was found in numbers 2-10. Combination of these fractions was followed by precipitation of the oxalate salt. The solids were recrystallized from 2-propanol-methanol resulting in 5.0 g of 1'-[4,4-diphenylbutyl]-7-chloro-2-methylspiro[2H-1,4-benzodioxepin-3(5H)4'-piperidine]oxalate (8.8 mmole, 53.52%) which appeared pure by TLC on silica gel in chloroform:methanol (9:1), $R_f=0.5$ and in dichloromethane:2-propanol (1:1), $R_f=0.4$. Mass Spec (MH+ =476), NMR-DMSO-$d_6$ and IR-KBr are consistent with the structure, m.p.=161°-165° C.

ANALYSIS: Calculated for $C_{32}H_{36}ClNO_6$: 67.89%C, 6.42%H, 2.47%N. Found: 67.64%C, 6.51%H, 2.36%N.

EXAMPLE 18

1'-[4,4-Bis(4-fluorophenyl)butyl]-7-chloro-2-methylspiro[2H-1,4-benzodioxepin-3(5H)4'-piperidine]oxalate The compound 7-chloro-2-methylspiro[2H-1,4-benzodioxepin-3(5H)4'-piperidine]hydrochloride (5 g, 16.5 mmole) was dissolved in 100 ml of DMF and was stirred with 5 g of potassium carbonate (milled, anhydrous) for 1 hr. To the resultant mixture 15 mg of potassium iodide and 5.5 g of 4,4-bis(4-fluorophenyl)butyl chloride (19.6 mmole) was added. The mixture was stirred under a nitrogen atmosphere at 90° C. for 6 hr.

The reaction was determined to be complete by GLC (OV 101:temperature program:225° C. (2 min) rate=30°/min to 280° C. (20 min) flow=30 ml/min). The reaction mixture was cooled to ambient temperature, quenched with water and extracted with ether. The ether extracts were backwashed with saturated brine followed by removal of the solvent under vacuum. The residue was loaded onto a 100 g alumina column packed in ether. Fractions of 50 ml of ether were collected and the desired material was found to be in numbers 2–5. These fractions were combined and the oxalate salt of the product was precipitated. The white solids were recrystallized from 2-propanolmethanol resulting in 5.3 g of 1′-[4,4-bis(4-fluorophenyl)butyl]-7-chloro-2-methylspiro[2H-1,4-benzodioxepin-3(5H)4′-piperidine]oxalate (8.8 mmole 53.50%) which appeared pure by TLC on silica gel in chloroform:methanol (9:1), $R_f$=0.5 and in dichloromethane:2-propanol (1:1), $R_f$=0.4. MS (MH+ =5.12). NMR-CDCl$_3$/DMSO-d$_6$ and IR-KBr are consistent with the structure, m.p.=170°–174° C.

ANALYSIS: Calculated for C$_{32}$H$_{34}$ClF$_2$NO$_6$: 63.83%C, 5.70%H, 2.33%N. Found: 63.66%C, 5.58%H, 2.21%N.

EXAMPLE 19

1′-[4,4-Bis(4-fluorophenyl)-3-butenyl]-7-chloro-2-methylspiro[2H-1,4-benzodioxepin-3(5H)4′-piperidine]oxalate The compound 7-chloro-2-methylspiro[2H-1,4-benzodioxepin-3(5H)4′-piperidine]hydrochloride (5 g, 16.5 mmole) was dissolved in 100 ml of DMF and stirred with 5 g of potassium carbonate (milled,anhydrous) and 15 mg of potassium iodide. To the mixture was added 5 g of 4,4-bis(4-fluorophenyl)-3-butenyl chloride (18.1 mmole), and the mixture was stirred at ambient temperature overnight. TLC indicated that no reaction had occurred. The mixture was heated to 90° C. and after 3 hrs products could be detected. Upon examination by GC/MS, it was determined that under these conditions the alkylating agent was not only reacting with the amine to form the desired product, but was also decomposing. The temperature of the reaction mixture was lowered to 55° C. The reaction was driven to completion through the addition of excess 4,4-bis(4-fluorophenyl)-3-butenyl chloride. Gas chromatographic conditions for the product were as follows: OV-101, 20 ml/min, temperature program, 225°–280° C., rate=30° C./min, $t_R$≅12.5 min. The reaction was quenched with an equal volume of water and the products were extracted into ether. The extracts were combined, backwashed with saturated brine and reduced in volume under vacuum. The residue was loaded onto a 100 g alumina column packed in ether. Fractions of 50 ml were collected and the desired material was in fraction numbers 3–6. The appropriate fractions were combined and the oxalate salt precipitated. The solids were recrystallized from 2-propanol/methanol resulting in 2.3 g of 1′-[4,4-bis(4-fluorophenyl)-3-butenyl]-7-chloro-2-methylspiro[2H-1,4-benzodioxepin-3(5H)4′-piperidine]oxalate (3.8 mmole, 23.2%), which appeared pure by TLC on silica gel in chloroform:methanol (9:1), $R_f$=0.6 and in dichloromethane:2-propanol, (1:1), $R_f$=0.5. MS (MH+ =510), NMR-TFA and IR-KBr are consistent with the structure, m.p.=212°–214° C.

ANALYSIS: Calculated for C$_{32}$H$_{34}$Cl$_2$NO$_6$: 64.04%C, 5.39%H, 2.33%N. Found: 64.00%C, 5.45%H, 2.32%N.

EXAMPLE 20

7-Chloro-2-methyl-1′-(3,3-diphenylpropyl)spiro[2H-1,4-benzodioxepin-3(5H)4′-piperidine]hydrochloride The compound 7-chloro-2-methylspiro[2H-1,4-benzodioxepin-3(5H)4′-piperidine]hydrochloride (7.4 g, 24.3 mmole) was dissolved in 200 ml of DMF and stirred with 7.5 g of milled, anhydrous potassium carbonate, 3,3-Diphenylpropyl chloride (6.2 g, 26.7 mmole) and 25 g of potassium iodide were added to the mixture, which was heated at 90° C. under nitrogen overnight. The reaction which was determined to be complete by TLC, was cooled and quenched with an equal volume of water. The products which were extracted into ether, were backwashed with saturated brine. The ether was removed under vacuum and the residue loaded onto a 200 g alumina column packed in ether. Fractions of 75 ml were collected and the desired material was found in numbers 4–7. These fractions were combined and the hydrochloride salt was precipitated. The material was recrystallized from toluene-ethyl-acetate resulting in 2 g of 7-chloro-2-methyl-1′-(3,3-diphenylpropyl)spiro[2H-1,4-benzodiozepin-3(5H)4′-piperidine]hydrochloride (4.0 mmole, 16.5%) which appeared pure by TLC on silica gel in chloroform:methanol (9:1), $R_f$=0.6 and in dichloromethane:2-propanol (1:1), $R_f$=0.5. A second crop (2.7 g, 5.2 mmole, 22.3%) was obtained having equal purity. MS (MH+ =261), NMR-CDCl$_3$ and IR-CHCl$_3$ are consistent with the structure, m.p.=224°–225° C.

ANALYSIS: Calculated for C$_{29}$H$_{33}$Cl$_2$NO$_2$: 69.86%C, 6.69%H, 2.81%H. Found: 69.98%C, 6.60%H, 2.72%N.

EXAMPLE 21

7-Bromo-1′-[4,4-bis(4-fluorophenyl)butyl]-2-methylspiro[2H-1,4-benzodioxepin-3(5H)4′-piperidine]oxalate The compound 7-bromo-2-methylspiro[2H-1,4-benzodioxepin-3(5H)4′-piperidine]hydrochloride (7.0 g, 20.1 mmole) was dissolved in 150 ml of DMF. The solution was stirred with 7.0 g of potassium carbonate (milled, anhydrous), 15 mg of potassium iodide and 6.2 g of 4,4-bis(4-fluorophenyl)butyl chloride (22.1 mmole) at 80° C. under nitrogen overnight. The reaction, which was determined to be complete by TLC, was cooled to ambient temperature, quenched with an equal volume of water, and extracted with ether. The ether extracts were combined and backwashed with saturated brine. The ether was removed under vacuum and the oily residue loaded onto a 140 g alumina column packed in ether. Fractions of 50 ml were collected and the desired material was found in numbers 2–4. These fractions were combined and the oxalate salt precipitated. The solids, which were recrystallized from ethyl acetate/methanol, appeared to be pure 7-bromo-1′-[4,4-bis(4-fluorophenyl)butyl]-2-methylspiro[2H-1,4-benzodioxepin-3(5H)4′-piperidine]-oxalate (4.30 g, 6.7 mmole, 33.1%) by TLC on silica gel in chloroform:methanol (9:1), $R_f$=0.5, and in dichloromethane:2-propanol (1:1), $R_f$=0.4, MS (MH+ =556/558), NMR-DMSO-d$_6$ and IR-KBr are consistent with the structure, m.p.=183°–186° C.

ANALYSIS: Calculated for $C_{32}H_{34}BrF_2NO_6$: 59.44%C, 5.31%H, 2.17%N. Found: 59.25%C, 5.26%H, 2.19%N.

EXAMPLE 22

1'-[4-(4-Fluorophenyl)-4-oxobutyl]-2-methylspiro[2H-1,4-benzodioxepin-3(5H)4'-piperidine]oxalate The compound 2-methylspiro[2H-1,4-benzodioxepin-3(5H)4'-piperidine]hydrochloride (50 g, 185.5 mmole) was dissolved in 1.5 l of DMF and stirred under nitrogen with 50 g of milled, anhydrous potassium carbonate for 4 hr. To this mixture was added 50.3 g of y-chloro-p-fluorobutyrophenone dimethyl ketal (204.1 mmole) and 0.15 g of potassium iodide. The resultant mixture was heated to 90° C. and allowed to react overnight, after which time the reaction was determined to be complete by TLC. The mixture was poured into water and the product extracted into ether. The ether extracts were combined, backwashed with saturated brine and reduced in volume under vacuum. The residue was dissolved in 800 ml of methanol and 300 ml of 3N hydrochloric acid. The mixture was heated to reflux under nitrogen and stirred for 2 hr. The solution was cooled and reduced in volume under vacuum. The residue was suspended in saturated aqueous sodium carbonate and extracted into ether. The extracts were combined, backwashed with saturated brine and dried over anhydrous potassium carbonate. The ether was removed under vacuum from the extract and the residue loaded onto a 1000 g alumina column packed in ether. Fractions of 500 ml of ether were collected and the desired product was found in numbers 2-4, which were combined. The oxalate salt was precipitated and recrystallized from 2-propanol, resulting in 28.6 g of 1'-[4-(4-fluorophenyl)-4-oxobutyl]-2-methylspiro[2H-1,4-benzodioxepin-3(5H)4'-piperidine]oxalate (58.7 mmole, 31.6%) which appeared pure by TLC on silica gel in chloroform:methanol (9:1), $R_f=0.5$ and dichloromethane:2-propanol (1:1), $R_f=0.4$, m.p.=134°-137° C. MS (MH+ =488), NMR-DMSO-d$_6$ and IR-KBr are consistent with the structure.

ANALYSIS: Calculated for $C_{26}H_{30}FNO_7$: 64.05% C, 6.21%H, 2.87%N. Found: 63.72%C, 6.15%H, 2.90%N.

EXAMPLE 23

1'-[4-Hydroxy-4-(4-fluorophenyl)butyl]-2-methyl-spiro[2H-1,4-benzodioxepin-3(5H)4'-piperidine]

The compound 1'-[4-(4-fluorophenyl)-4-oxobutyl]-2-methylspiro[2H-1,4-benzodioxepin-3(5H)4'-piperidine]oxalate (15 g, 30.8 mmole) was converted to its free base and dried. The residue was dissolved in 50 ml of ethanol and stirred with 0.8 g of sodium borohydride (pellets) under a nitrogen atmosphere, over the weekend, at ambient temperature. The mixture was stirred with 40 ml of 3N HCl which resulted in the formation of solids. The solids were insoluble in water and could be recrystallized from ethyl acetate (8.7 g, 20.0 mmole, 65.0%). Upon treatment with saturated sodium carbonate solution and chloroform, all solids were dissolved. After drying the organic phase, and the removal of the solvent, there remained a crystalline solid which could be recrystallized from chloroform/hexane. The material was identified as 1'-[4-hydroxy-4-(4-fluorophenyl)butyl]-2-methylspiro[2H-1,4-benzodioxepin-3(5H)4'-piperidine]. The compound appeared pure by TLC on silica gel in chloroform:methanol (9:1), $R_f=0.5$, and in dichloromethane:2-propanol, (1:1), $R_f=0.4$. MS (MH+ =400), NMR-CDCl$_3$ and IR-CHCl$_3$ are consistent with the structure, m.p.=143°-146° C.

ANALYSIS: Calculated for $C_{24}H_{30}FNO_3$: 72.14%C, 7.58%H, 3.50%N. Found: 72.00%C, 4.49%H, 3.38%N.

EXAMPLE 24

1'-[4-(4-Fluorophenoxy)-4-(4-fluorophenyl)butyl]-2-methylspiro[2H-1,4-benzodioxepin-3(5H)4'-piperidine]oxalate Sodium hydride (0.96 g of a 50% mineral oil suspension, 0.02 mole) was hexane washed, suspended in 80 ml of DMSO and heated to 60°-70° C. until evolution of hydrogen ceased. The mixture was cooled to 5° C. and to it was added a solution of 6.8 g of 1'-[4-hydroxy-4-(4-fluorophenyl)butyl]-2-methyl-spiro[2H-1,4-benzodioxepin-3(5H)4'-piperidine] dissolved in 225 ml of DMSO. The mixture was stirred at ambient temperature for 15 min. after which 8.0 g of 1,4-difluorobenzene (0.07 mole) was added. The mixture was heated to 70° C. and maintained at that temperature overnight. TLC indicated 50-60% completion of reaction which was not improved by heating at 80° C. The mixture was cooled to ambient temperature and quenched with an equal volume of water. The products were extracted into ether and backwashed with saturated brine. The ether was removed under vacuum and the residue purified by preparative HPLC using two silica gel columns (2×500 cc), eluting with hexane:ether:methanol (10:10:1). The desired material was detected by refractive index and ultraviolet absorption. The fractions which contained the product were combined and the solvent removed under vacuum. The oil residue was dissolved in ether and the oxalate salt precipitated. The solids were recrystallized from ethylacetate:methanol. The resultant 1'-[4-(4-fluorophenoxy)-4-(4-fluorophenyl)butyl]-2-methylspiro[2H-1,4-benzodioxepin-3(5H)4'-piperidine]oxalate (3.9 g, 7.9 mmole 39.5%) appeared pure by TLC on silica gel in chloroform: methanol (9:1), $R_f=0.5$ and in hexane:ether:methanol (10:10:1), $R_f=0.3$. MS (MH+ =494), NMR-DMSO-d$_6$, CMR-DMSO-d$_6$ and IR-KBr are consistent with the structure, m.p.=180°-182° C.

ANALYSIS: Calculated for $C_{32}H_{35}F_2NO_3$: 65.85%C, 6.06%H, 2.40%N. Found: 66.05%C, 6.07%H, 2.27%N.

EXAMPLE 25

1-Acetyl-4-ethynyl-4-(2,5-difluorophenylmethoxy)-piperidine

A solution of 7.0 g of potassium t-butoxide (62.5 mmole) in 20 ml of dry DMF was added dropwise to a chilled solution of 10 g of 1-acetyl-4-ethynyl-4-hydroxypiperidine (59.9 mmole) in 75 ml of dry DMF, at such a rate as to maintain the temperature at 10° C. The mixture was allowed to equilibrate at 10° C. for 15 min. after which time it was cooled to −20° C. After complete addition the reaction mixture was warmed to 0° C. and allowed to react for 1 hr. The reaction appeared to be complete by GLC and was quenched with ice and water. The products were extracted into ether and dried over K$_2$CO$_3$. After filtration the solvent was removed under vacuum. The crystalline product was recrystallized from cyclohexane and dried, affording 10.5 g of 1-acetyl-4-ethynyl-4-(2,5-difluorophenylmethoxy)piperidine (35.8 mmole, 59.83%). This material appeared pure by GLC (99% on OV225, temperature program: 200° C. (2 min.), rate=25° C./min., 250° C. (15 min.), flow=30 ml/min. $t_R$=4.00 min.) and by TLC on silica gel in hexane:ethylacetate (1:1), $R_f$ 0.2. Mass Spec (ci MH+=294), NMR-CDCl$_3$ and IR-CHCl$_3$ are consistent with the structure, m.p.=90°-93° C.

ANALYSIS: Calculated for $C_{16}H_{17}F_2NO_2$: 65.51%C, 5.85%H, 4.77%N. Found: 65.72%C, 5.87%H, 4.68%N.

EXAMPLE 26

4-(1-Oxoethyl)-4-(2,5-difluorophenylmethoxy)piperidine hydrochloride

The compound 1-acetyl-4-ethynyl-4-(2,5-difluorophenylmethoxy)piperidine (5g, 17.1 mmole) was suspended in 50 ml of 15% sulfuric acid. The mixture was heated at reflux under nitrogen for 1 hr. after which complete dissolution occurred. Mercuric sulfate (0.25 g, freshly opened) was added to the cooled solution. The mixture was heated at 65° C. overnight. The reaction was determined to be 98% complete by GLC. The mixture was basified with saturated aqueous sodium carbonate and extracted with chloroform. The organic extracts were combined, dried over $K_2CO_3$ and filtered through celite. The filtrate was reduced in volume under vacuum and the residue dissolved in ether. The hydrochloride salt was precipitated and recrystallized from ethylacetate/ethanol, yielding, in two crops, 3.2 g of 4-(1-oxoethyl)-4-(2,5-difluorophenylmethoxy)piperidine hydrochloride (10.48 mmole, 61.4%) which appeared pure by GLC (OV225, temperature program 200° C. (2 min.), rate=25°/min., 250° C. (15 min.), flow=30 ml/min., $t_R$=1.59) and by TLC on silica gel in 2-propanol:ammonium hydroxide (8:2), $R_f$=0.8, MS (ci MH+=270), NMR-DMSO-d$_6$ and IR-KBR are consistent with the structure, m.p.=197°-201° C.

ANALYSIS: Calculated for $C_{14}H_{18}ClF_2NO_2$: 54.99%C, 5.95%H, 4.58%N. Found: 55.03%, 5.88%H, 4.70%N.

EXAMPLE 27

4-(1-Hydroxyethyl)-4-(2,5-difluorophenylmethoxy)-piperidine

The compound 4-(1-oxoethyl)-4-(2,5-difluorophenylmethoxy)piperidine hydrochloride (5 g, 16.4 mmole) was dissolved in 50 ml of water. The pH was adjusted to 8.5 using 50% sodium hydroxide. Sodium borohydride (0.2 g, 4.5 mmole) was added to the solution and the mixture was allowed to react for ½ hr. The reaction was determined to be complete by GLC. The reaction mixture was saturated with potassium carbonate and extracted with ether. The ether extracts were combined, dried, and filtered. The solvent was removed under vacuum resulting in 4 g of solid white material. This solid was recrystallized from cyclohexane resulting in 3.5 g of 4-(1-hydroxyethyl)-4-(2,5-difluorophenylmethoxy)piperidine (12.9 mmole, 78.7%) which appeared pure by GLC (OV 225, temperature program: 200° C. (2 min.), rate=25°/min., 250° C. (15 min.), flow=30 ml/min., $t_R$=2.31) and by TLC on silica gel in 2-propanol:ammonium hydroxide (8:2), $R_f$=0.5. MS (ci MH+=272). NMR-CDCl$_3$ and IR-CHCl$_3$ are consistent with the structure. m.p.=94°-96° C.

ANALYSIS: Calculated for $C_{14}H_{19}F_2NO_2$: 61.97%C, 7.07%H, 5.16%N. Found: 61.92%C, 7.26%H, 5.00%N.

EXAMPLE 28

7-Fluoro-2-methyl spiro[2H-1,4-benzodioxepin-3(5H)4'-piperidine]hydrochloride

The compound 4-(1-hydroxyethyl)-4-(2,5-difluorophenylmethoxy)piperidine (84.4 g, 311.0 mmole) was dissolved in 510 ml of dry THF and stirred with 36.6 g of potassium tert-butoxide (326.0 mmole). The mixture was heated at reflux under nitrogen for 8 hrs, after which a 10% excess of potassium tert-butoxide was added. The mixture was treated 6 hrs, after which the reaction was determined to be complete by GLC. The mixture was cooled and quenched with saturated aqueous sodium carbonate. The product was extracted into ether and dried over potassium carbonate. The dried ether extracts were filtered and the hydrochloride salt was precipitated. The solids were filtered, dried (85.0 g, 287.0 mmole, 92.9%), and recrystallized from ethylacetate/ethanol. The resultant crystals were filtered and vacuum dried at 60° C. resulting in 62.6 g of 7-fluoro-2-methylspiro[2H-1,4-benzodioxepin-3(5H)4'-piperidine]hydrochloride (218.0 mmole, 70.01%). The material appeared pure by GLC (OV225, flow=30 ml/min., temperature program: 200° C. (2 min.), rate=25° C./min., silica gel in 2-propanol:ammoniumhydride (8:2), $R_f$=0.5. MS (ci MH+=251), NMR-DMSO-d$_6$ and IR-KBr are consistent with the structure, m.p.=273-277°Cd.

ANALYSIS: Calculated for $C_{14}H_{19}ClFNO_2$: 58.43%C, 6.67%H, 4.86%N. Found: 58.30%C, 6.54%H, 4.80%N.

EXAMPLE 29

1'-(4,4-Diphenylbutyl)-7-fluoro-2-methyl spiro-[2H-1,4-benzodioxepin-3(5H)4'-piperidine]hyrochloride 7-Fluoro-2-methyl spiro[2H-1,4-benzodioxepin-3(5H)4'-piperidine]hydrochloride (5 g 17.4 mmole) was dissolved in 100 ml of DMF and stirred with 5 g of milled, anhydrous potassium carbonate, 15 mg of potassium iodide and 4.7 g of 4,4-diphenylbutylchloride (19.1 mmole) at 65° C. under nitrogen overnight. The reaction which was determined to be complete by TLC was cooled, quenched with an equal volume of water and extracted with ether. The ether extracts were combined and backwashed with saturated sodium chloride. The solvent was removed under vacuum. The oily residue was loaded onto a 100 g alumina column packed with ether. Fractions of 50 ml were collected and the desired material was found in numbers 2-3. These fractions were combined and the solvent was removed under vacuum. The residual oil was dissolved in anhydrous ether and the hydrochloride salt precipitated. Recrystallization from toluene/ethyl acetate/ethanol afforded 3.0 g (6.1 mmole, 34.8%) of 1'-(4,4-diphenylbutyl)-7-fluoro-2-methyl spiro[2H-1,4-benzodioxepin-3(5H)4'-piperidine]hydrochloride which appeared pure by TLC on silica gel in dichloromethane:methanol (9:1), $R_f$=0.6 and in dichloromethane:2-propanol (1:1), $R_f$=0.5. MS (ci MH+=460). NMR-DMSO-d$_6$ and IR-KBr are consistent with the structure. m.p.=215°-218° C.

ANALYSIS: Calculated for $C_{30}H_{35}ClFNO_2$: 72.63%C, 7.13%H, 2.82%N. Found: 72.73%C, 6.74%H, 2.56%N.

EXAMPLE 30

1'-[4,4-Bis-(4-fluorophenyl)butyl]-7-fluoro-2-methyl-spiro[2H-1,4-benzodioxepin-3(5H)4'-piperidine]hydrochloride 7-Fluoro-2-methylspiro[2H-1,4-benzodioxepin-3(5H)4'-piperidine]hydrochloride (5.0 g, 17.4 mmole) was dissolved in 100 ml of DMF and stirred with 5 g of milled, anhydrous potassium carbonate, 15 mg potassium iodide and 5.4 g of 4,4-bis(4-fluorophenyl)butylchloride (19.1 mmole) at 65° C. under nitrogen overnight. The reaction which was determined to be complete by TLC, was cooled, quenched with an equal volume of water and extracted with ether. The ether extracts were combined and back-washed with saturated brine. The solvent was removed under vacuum. The oily residue was loaded onto a 100 g alumina column packed in ether. Fractions of 50 ml were collected and the desired product was found in numbers 2–4. These fractions were combined and the solvent was removed under vacuum. The residual oil was dissolved in anhydrous ether and the hydrochloride salt precipitated. Recrystallization from toluene ethyl acetate/ethanol afforded 5.9 g (7.3 mmole, 42.2%) of 1'-[4,4-bis(4-fluorophenyl)butyl]-7-fluoro-2-methylspiro[2H-1,4-benzodioxepin-3(5H)4'-piperidine]hydrochloride which appeared pure by TLC on silica gel in dichloromethane:methanol (9:1), $R_f=0.6$ and in dichloromethane:2-propanol (1:1), $R_f=0.5$. MS (ci MH+ =496), NMR-DMSO-d$_6$ and IR-KBr are consistent with the structure, m.p.=162°–165° C.

ANALYSIS: Calculated for $C_{30}H_{33}ClF_3NO_2$: 67.72%C, 6.26%H, 2.63%N. Found: 67.35%C, 5.95%H, 2.56%N.

In Examples 31 to 36, an alternate method for preparing the compound of formula (7) in FIG. 1 is described. The 1-methyl-4-ethynyl-4-hydroxypiperidine employed as starting material in Example 31 can be prepared by the method disclosed in N. Barbulescu, C. Bornaz and C. Greff, Rev. Chim. (Bucharest) 20 (6): 373–374 (1969).

EXAMPLE 31

1-Methyl-4-ethynyl-4-(2-fluorophenylmethoxy)piperidine oxalate

To a stirred suspension of 7.8 g of NaH (163.0 mmole), 50% in oil; washed three times with hexane) in 80 ml dry DMF was added dropwise a solution of 20 g (144.0 mmole) of 1-methyl-4-ethynyl-4-hydroxy piperidine in 120 ml of DMF. The solution was allowed to cool to room temperature and, subsequently, 20 ml (169.0 mmole) of 2-fluorobenzyl chloride was added dropwise. The mixture was allowed to stir overnight, poured slowly into water, extracted twice with ether, washed with saturated sodium chloride, dried over potassium carbonate, filtered and the solvent evaporated, yielding 1-methyl-4-ethynyl-4-(2-fluorophenylmethoxy)piperidine oxalate (35.2 g 104.0 mmole, 72.0%).

ANALYSIS: Calculated for $C_{15}H_{18}FNO.C_2H_2O_4$: 60.70%C, 6.01%H, 4.16%N. Found: 60.42%C, 5.97%H, 4.08%N.

EXAMPLE 32

4-(1-Oxoethyl)-4-(2-fluorophenylmethoxy)-1-methylpiperidine oxalate

To a suspension of 1-methyl-4-(2-fluorophenylmethoxy)piperidine (liberated from 30.6 g, 90.7 mmole, of the oxalate, and 165 ml of water was added a solution of 22 ml of conc. sulfuric acid in 53 ml of water. To the solution was added 4.0 g (13.4 mmole) of mercuric sulfate. The mixture was heated at reflux for 1.5 hr. under nitrogen and allowed to cool to room temperature. The mixture was poured into cold saturated sodium carbonate, extracted twice with ether and washed with saturated sodium chloride. The ether solution was dried over anhydrous potassium carbonate, filtered and the solvent evaporated to provide an oil. The oxalate salt was precipitated, and recrystallization from methanol/ethanol provided 21.1 g (59.4%) of 4-(1-oxoethyl)-4-(2-fluorophenylmethoxy)-1-methylpiperidine oxalate. The material appeared pure by TLC on silica gel in methanol:methylene chloride (9:1), $R_f=0.4$ and on alumina in ether, $R_f=0.3$. IR (Nujol), NMR-DMSO-d$_6$ and MS (ci MH+ =266) are consistent with the structure, m.p.=180°–181° C.

ANALYSIS: Calculated for $C_{15}H_{20}FNO_2.C_2H_2O_4$: 57.45%C, 6.24%H, 3.94%N. Found: 57.25%C, 6.26%H, 3.82%N.

EXAMPLE 33

4-(1-Hydroxyethyl)-4-(2-fluorophenylmethoxy)-1-methylpiperidine oxalate

Sodium borohydride (533 g, 1.4 mole) was dissolved in 4500 ml methanol. To the resulting solution was added, with stirring, a solution of 4-(1-oxoethyl)-4-(2-fluorophenylmethoxy)-1-methylpiperidine (151 g, 0.6 mole) in 500 ml methanol. The reaction was allowed to proceed at 0° C. for 1.5 hrs. The reaction mixture was made basic with 3 l. of saturated aqueous Na$_2$CO$_3$ causing a precipitate to form. To the mixture was added 2 l. diethyl ether. The resulting solution was worked up with cold water and diethyl ether and the diethyl ether extracts were combined. The oxalate salt was precipitated and recrystallized from 2-propanol. After recrystallization, filtration and drying in vacuo at 45° C., 32 g of 4-(1-hydroxyethyl)-4-(2-fluorophenylmethoxy)-1-methylpiperidine oxalate were obtained. MS (ci MH+ =268), NMR-DMSOd$_6$ and IR-KBr were consistent with the structure, m.p.=104°–106° C.

ANALYSIS: Calculated for $C_{14}H_{24}NO_6F$: 57.12%C, 6.78%H, 3.92%N. Found: 56.65%C, 6.72%H, 3.77%N.

EXAMPLE 34

1',2-dimethylspiro[2H-1,4-benzodioxepin-3(5H)4'-piperidine]oxalate

The free base of 4-(1-hydroxyethyl)-4-(2-fluorophenylmethoxy)-1-methylpiperidine was generated from its oxalate with saturated sodium bicarbonate and extracted into chloroform. This was dried over anhydrous sodium sulfate, taken to dryness, weighed (30.3 g, 115.0 mmole) and dissolved in 300 ml of dry dimethylformamide. This solution was added dropwise and under nitrogen to a stirred suspension of hexane washed sodium hydride (6.5 g 50% mineral oil suspension, 136.0 mmole). The mixture was heated to 130° C. and stirred for 0.5 hr. The reaction was quenched, when conversion was greater than 90% by GLC (3% ASI column, flow=42 ml/min, 200° C.), by adding ice and water. The products were isolated by ether extraction. The extracts were dried over anhydrous potassium carbonate, filtered and the oxalate salt precipitated. Recrystallization was carried out in methanol resulting in 11.1 g of 1',2-dimethylspiro[2H-1,4-benzodioxepin-3(5H)4'-piperidine]oxalate. The material appeared pure by thin layer chromatography on silica gel in chloroform:methanol (1:1), $R_f$=0.25 and on alumina in chloroform:methanol (95:5), $R_f$=0.90. MS (ci MH+ =248), IR-KBr and NMR-DMSO-$d_6$ are consistent with the structure. m.p.=162°-165° C.

ANALYSIS: Calculated for $C_{15}H_{21}N_1O_2.C_2H_2O_4$: 60.53%C, 6.82%H, 4.15%N. Found: 60.26%C, 6.85%H, 4.10%N.

EXAMPLE 35

1'-(Phenoxycarbonyl)-2-methylspiro[2H-1,4-benzodioxepin-3(5H)4'-piperidine]

The compound 1',2-dimethylspiro[2H-1,4-benzodioxepin-3(5H)4'-piperidine] (194.4 g, 787.0 mmole) was dissolved with stirring under a nitrogen blanket in 2 l, of dichloromethane. Anhydrous $K_2CO_3$ (131 g) was added to the resulting solution. Phenoxycarbonyl chloride (147.1 g, 930.0 mmole) was then added with stirring. The resulting mixture was allowed to react overnight at ambient temperature. After successive acidic and alkaline washes, the mixture was dried over $MgSO_4$, filtered and taken to dryness. A 10 g sample of the product was loaded onto a column of silica gel (100 g) packed in chloroform, and thirteen 75 ml fractions were recovered. Mass spectra showed the compound to be in fractions 5-11. These fractions were combined and taken to dryness. The oily residue was crystallized from hexane-cyclohexane resulting in 1.55 g of 1'-phenoxycarbonyl-2-methylspiro[2H-1,4-benzodioxepin-3(5H)4'-piperidine] which appeared pure by TLC in chloroform:methanol (95:5), $R_f$=0,4, MS (ci MH+ =354), NMR-CDCl$_3$ and IR-CHCl$_3$ are consistent with the structure, m.p.=85°-89° C.

ANALYSIS: Calculated for $C_{21}H_{23}NO_4$: 71.36%C, 6.57%H, 3.96%N. Found: 71.31%C, 6.60%H, 3.96%N.

EXAMPLE 36

2-Methylspiro[2H-1,4-benzodioxepin-3(5H)4'-piperidine]oxalate

1'-Phenoxycarbonyl-2-methylspiro[2H-1,4-benzodioxepin-3-(5H)4'-piperidine] (44.0 g, 130.0 mmole) was dissolved in 230 ml methanol, to which was added 128.2 ml of 15% aqueous sodium hydroxide. With stirring under nitrogen, the mixture was heated to 60° C. and maintained at that temperature for 18 hrs. The mixture was cooled to room temperature and extracted with chloroform. The chloroform extracts were combined and dried over anhydrous potassium carbonate, filtered and taken to dryness. The residue was dissolved in ethanol:ether (1:1) and the oxalate salt precipitated (11.9 g, 0.037 mole, 28.31%). A 5 g sample was recrystallized from ethanol yielding 2.5 g of material which appeared pure by thin layer chromatography on silica gel in chloroform:methanol (1:1), $R_f$=0.1 and ethanol:ammonium hydroxide (7:3), $R_f$=0.85. MS (ci MH+ =234), IR-KBr and NMR-DMSO-$d_6$ were all consistent with the structure, m.p.=216°-218° C.

ANALYSIS: Calculated for $C_{15}H_{21}N_1O_2.C_2H_2O_4$: 60.53%C, 6.82%H, 4.15%N. Found: 60.26%C, 6.84%H, 4.10%N.

EXAMPLE 37

1-Acetal-4-ethynyl-4-(2,5-difluorophenylmethoxy)piperidine

A solution of 7.04 g of potassium t-butoxide (62.9 mmole) in 20 ml of dry DMF was added dropwise to a chilled solution of 10 g of 1-acetyl-4-ethynyl-4-hydroxypiperidine (59.9 mmole) in 75 ml of dry DMF, at such a rate as to maintain the temperature at 10° C. The mixture was allowed to equilibrate at 10° C. for 15 min. after which time it was cooled to −20° C. To this solution was added 9.73 g of 2,5-difluorobenzylchloride (59.9 mmole) at such a rate as to maintain the temperature around −20° C. After complete addition, the reaction mixture was warmed to 0° C. and allowed to react for 1 hr. The reaction appeared to be complete by GLC and was quenched with ice and water. The products were extracted into ether and dried over $K_2CO_3$. After filtration, the solvent was removed under vacuum. The crystalline product was recrystallized from cyclohexane and dried, affording 10.5 g of 1-acetyl-4-ethynyl-4-(2,5-difluorophenylmethoxy)piperidine (35.8 mmole, 59.83%). This material appeared pure by GLC (99% on OV225, temperature program: 200° C. (2 min), rate=25° C./min, 250° C. (15 min), flow=30 ml/min $t_R$=4.00 min) and ty TLC on silica gel in hexane:ethylacetate (1:1), $R_f$=0.2. MS (ci MH+ =294). NMR-CDCl$_3$ and IR-CHCl$_3$ were consistent with the structure; m.p.=90°-93° C.

ANALYSIS: Calculated for $C_{16}H_{17}F_2NO_2$: 65.51%C, 5.85%H, 4.77%N. Found: 65.72%C, 5.87%H, 4.68%N.

EXAMPLE 38

4-(1-Oxoethyl)-4-(2,5-difluorophenylmethoxy)piperidine hydrochloride

The compound 1-acetyl-4-ethynyl-4-(2,5-difluorophenylmethoxy)piperidine (5 g, 17.06 mmole) was suspended in 50 ml of 15% sulfuric acid. The mixture was heated at reflux under nitrogen for 1 hr, after which complete dissolution occurred. Mercuric sulfate (0.25 g, freshly opened) was added to the cooled solution. The mixture was heated at 65° C. overnight. The reaction was determined to be 98% complete by GLC. The mixture was basified with saturated aqueous sodium carbonate and extracted with chloroform. The organic extracts were combined, dried over $K_2CO_3$ and filtered through celite. The filtrate was reduced in volume under vacuum and the residue dissolved in ether. The hydrochloride salt was precipitated and recrystallized from ethylacetate/ethanol, yielding, in two crops, 3.2 g of 4-(1-oxoethyl)-4-(2,5-difluorophenylmethoxy)piperidine hydrochloride (10.48 mmole, 61.4%), which appeared pure by GLC (OV225, temperature program 200° C. (2 min), rate=25°/min, 250° C. (15 min), flow=30 ml/min, $t_R$=1.59) and by TLC on silica gel in 2-propanol:ammonium hydroxide (8:2), $R_f$=0.8. MS (ci MH+ =270), NMR-DMSO-$d_6$ and IR-KBr were consistent with the structure; m.p.=197°-201° C.

ANALYSIS: Calculated for $C_{14}H_{18}ClF_2NO_2$: 54.99%C, 5.95%H, 4.58%N. Found: 55.03%C, 5.88%H, 4.70%N.

EXAMPLE 39

4-(1-Hydroxyethyl)-4-(2,5-difluorophenylmethoxy)-piperidine

The compound 4-(1-oxoethyl)-4-(2,5-difluorophenylmethoxy)piperidine hydrochloride (5 g, 16.4 mmole) was dissolved in 50 ml of water. The pH was adjusted to 8.5 using 50% sodium hydroxide. Sodium borohydride (0.2 g, 4.5 mmole) was added to the solution and the mixture was allowed to react for ½ hour. The reaction was determined to be complete by GLC. The reaction mixture was saturated with potassium carbonate and extracted with ether. The ether extracts were combined, dried and filtered. The solvent was removed under vacuum resulting in 4 g of solid white material. This solid was recrystallized from cyclohexane resulting in 3.5 g of 4-(1-hydroxyethyl)-4-(2,5-difluorophenylmethoxy)piperidine (12.9 mmole, 78.7%), which appeared pure by GLC (OV225, temperature program: 200° C. (2 min) rate=25°/min 250° C. (15 min) flow=30 ml/min $t_R$=2.31) and by TLC on silica gel in 2-propanol:ammonium hydroxide (8:2) $R_f$=0.5. MS (ci $MH^+$=272). NMR-CDCl$_3$ and IR-CHCl$_3$ were consistent with the structure; m.p.=94°–96° C.

ANALYSIS: Calculated for C$_{14}$H$_{19}$F$_2$NO$_2$: 61.97%C, 7.07%H, 5.16%N. Found: 61.92%C, 7.26%H, 5.00%N.

EXAMPLE 40

7-Fluoro-2-methylspiro[2H-1,4-benzodioxepin-3(5H)4'-piperidine]hydrochloride The compound 4-(1-hydroxyethyl)-4-(2,5-difluorophenylmethoxy)piperidine (84.4 g, 0.311 mole) was dissolved in 510 ml of dry THF and stirred with 36.6 g of potassium tert-butoxide (0.326 mole). The mixture was heated at reflux under nitrogen for 8 hr after which a 10% excess of potassium tert-butoxide was added. The mixture was heated 6 hr after which the reaction was determined to be complete by GLC. The mixture was cooled and quenched with saturated aqueous sodium carbonate. The product was extracted into ether and dried over potassium carbonate. The dried ether extracts were filtered and the hydrochloride salt was precipitated. The solids were filtered, dried (83.0 g, 0.289 mole, 92.83%) and recrystallized from ethyl acetate/ethanol. The resultant crystals were filtered and vacuum dried at 60° C. resulting in 62.6 g of 7-fluoro-2-methylspiro[2H-1,4-benzodioxepin-3(5H)4'-piperidine]hydrochloride (0.218 mole 70.01%). This material appeared pure by GLC (OV225, flow=30 ml/min, temperature program: 200° C. (2 min), rate=25° C. (15 min), $t_R$=1.82) and TLC on silica gel in 2-propanol:ammonium hydroxide (8:2), $R_f$=0.5. MS (ci $MH^+$=251), NMR-DMSO-d$_6$, and IR-KBr were consistent with the structure; m.p.=273°–277° C.(d).

ANALYSIS: Calculated for C$_{14}$H$_{19}$ClFNO$_2$: 58.43%C, 6.67%H, 4.86%N. Found: 58.30%C, 6.54%H, 4.80%N.

EXAMPLE 41

1'-(4,4-Diphenylbutyl)-7-fluoro-2-methylspiro[2H-1,4-benzodioxepin-3(5H)4'-piperidine]hydrochloride The compound 7-fluoro-2-methylspiro[2H-1,4-benzodioxepin-3(5H)4'-piperidine]hydrochloride (5 g, 17.39 mmole) was dissolved in 100 ml of DMF and stirred with 5 g of milled, anhydrous potassium carbonate, 15 mg potassium iodide and 4.7 g of 4,4-diphenylbutylchloride (19.13 mmole) at 65° C. under nitrogen, overnight. The reaction, which was determined to be complete by TLC, was cooled, quenched with an equal volume of water and extracted with ether. The ether extracts were combined and backwashed with saturated sodium chloride. The solvent was removed under vacuum. The oily residue was loaded onto a 100 g alumina column packed in ether. Fractions of 50 ml were collected and the desired material was found in fraction numbers 2–3. These fractions were combined and the solvent was removed under vacuum. The residual oil was dissolved in anhydrous ether and the hydrochloride salt precipitated. Recrystallization from toluene/ethyl acetate/ethanol afforded 3.0 g (6.05 mmole, 34.79%) of 1'-(4,4-diphenylbutyl)-7-fluoro-2-methylspiro[2H-1,4-benzodioxepin-3(5H)4'-piperidine]hydrochloride, which appeared pure by TLC on silica gel in dichloromethane/methanol (9:1), $R_f$=0.6 and in dichloromethane/2-propanol (1:1), $R_f$=0.5. MS (ci $MH^+$=460), NMR-DMSO-d$_6$ and IR-KBr were consistent with the structure; m.p.=215°–218° C.

ANALYSIS: Calculated for C$_{30}$H$_{35}$ClFNO$_2$: 72.63%C, 7.13%H, 2.82%N. Found: 72.73%C, 6.74%H, 2.56%N.

EXAMPLE 42

1'-[4,4-Bis(4-fluorophenyl)butyl]-7-fluoro-2-methylspiro[2H-1,4-benzodioxepin-3(5H)4'-piperidine]hydrochloride The compound 7-fluoro-2-methylspiro[2H-1,4-benzodioxepin-3(5H)4'-piperidine]hydrochloride (5.0 g, 17.39 mmole) was dissolved in 100 ml of DMF and stirred with 5 g of milled, anhydrous potassium carbonate, 15 mg of potassium iodide and 5.36 g of 4,4-bis(4-fluorophenyl)butylchloride at 65° C. under nitrogen overnight. The reaction, which was determined to be complete by TLC, was cooled, quenched with an equal volume of water and extracted with ether. The ether extracts were combined and backwashed with saturated brine. The solvent was removed under vacuum. The oily residue was loaded onto a 100 g alumina column packed in ether. Fractions of 50 ml were collected and the desired product was found in fraction numbers 2–4. These fractions were combined and the solvent was removed under vacuum. The residual oil was dissolved in anhydrous ether and the hydrochloride salt precipitated. Recrystallization from toluene/ethyl acetate/ethanol afforded 3.9 g 0.34 mole, 42.21%) of 1'[4,4-bis(4-fluorophenyl)butyl]-7-fluoro-2-methylspiro[2H-1,4-benzodioxepin-3(5H)4'-piperidine]hydrochloride, which appeared pure by TLC on silica gel in dichloromethane:methanol (9:1), $R_f$=0.6 and in dichloromethane:2-propanol (1:1), $R_f$=0.5. MS (ci $MH^+$=496), NMR-DMSO-d$_6$ and IR-KBr were consistent with the structure; m.p.=162°–165° C.

ANALYSIS: Calculated for C$_{30}$H$_{33}$ClF$_3$NO$_2$: 67.72%C, 6.26%H, 2.63%N. Found: 67.35%C, 5.95%H, 2.56%N.

EXAMPLE 43

1'-[2-[Bis(4-fluorophenyl)methoxy]ethyl]-7-fluoro-2-methylspiro[2H-1,4-benzodioxepin-3(5H)4'-piperidine]-hydrochloride The compound 7-fluoro-2-methylspiro[2H-1,4-benzodioxepin-3(5H)4'-piperidine]hydrochloride (5 g, 17.4 mmole) was suspended in 100 ml of n-butylacetate along with 5 g of potassium carbonate (milled, anhydrous), 5.4 g of [2-[bis(4-fluorophenyl)methoxy]ethyl]-chloride (19.1 mmole) and 15 mg of potassium iodide. The mixture was stirred under nitrogen at reflux overnight. The reaction was determined to be complete by TLC. The mixture was filtered and the solvent was removed under vacuum. The residue was loaded onto a 100 g alumina column packed in ether. Fractions of 50 ml of ether were collected and the desired material was found in fraction numbers 3–6. These fractions were combined. The hydrochloride salt was precipitated and dried, resulting in 5.8 g of 1'-[2-[bis(4-fluorophenyl)methoxy]ethyl]-7-fluoro-2-methylspiro[2H-1,4-benzodioxepin-3(5H)4'-piperidine]hydrochloride (10.9 mmole, 62.64%). The material appeared pure by TLC on silica gel in dichloromethane:methanol (9:1), $R_f$=0.6 and in hexane:diethylamine (40:3), $R_f$=0.3. MS (ci MH+ =498), NMR-DMSO-$d_6$ and IR-CHCl$_3$ were consistent with the structure; m.p.=165°–168° C.

ANALYSIS: Calculated for $C_{29}H_{31}ClF_3NO_3$: 65.22%C, 5.86%H, 2.62%N. Found: 65.24%C, 5.81%H, 2.68%N.

EXAMPLE 44

1'-[2-[Bis(4-fluorophenyl)methoxy]ethyl]-2-methylspiro[2H-1,4-benzodioxepin-3(5H)4'-piperidine]hydrochloride The compound 2-methylspiro[2H-1,4-benzodioxepin.3(5H)4'-piperidine]hydrochloride (3.3 g, 12.2 mmole) was suspended in 100 ml of n-butylacetate along with 3 g of potassium carbonate (milled, anhydrous), 3.8 g of 2-[bis(4-fluorophenyl)methoxy]ethyl chloride (13.5 mmole) and 15 mg of potassium iodide. The mixture was stirred under nitrogen and heated at reflux overnight. The reaction was determined to be complete by TLC. The mixture was filtered and the solvent was removed under vacuum. The residue was loaded onto a 100 g alumina column packed in ether. Fractions of 50 ml of ether were collected and the desired material was found in fraction numbers 3–5. These fractions were combined. The hydrochloride salt was precipitated and was recrystallized from ethyl acetate:2-propanol, yielding 3.3 g of 1'-[2-[bis(4-fluorophenyl)methoxy]ethyl]-2-methylspiro[2H-1,4-benzodioxepin-3(5H)4'-piperidine]hydrochloride (6.4 mmole, 52.5%) in two crops. This material appeared pure by TLC on silica gel in dichloromethane:methanol (9:1) $R_f$=0.6 and in hexane:diethylamine (40:3) $R_f$=0.3. MS (ci MH+ =480), NMR-DMSO-$d_6$ and IR-KBr were consistent with the structure; m.p.=179°–181° C.

ANALYSIS: Calculated for $C_{29}H_{32}ClF_2NO_3$: 67.49%C, 6.26%H, 2.71%N. Found: 67.36%C, 6.23%H, 2.49%N.

EXAMPLE 45

1'-(Cyanomethyl)-2-methylspiro[2H-1,4-benzodioxepin-3(5H)-4'-piperidine]

The compound 2-methylspiro[2H-1,4-benzodioxepin-3(5H)4'-piperidine]oxalate (6 g; 18.5 mmole) was converted to its free base and dried over anhydrous potassium carbonate. After filtration and removal of solvent, the residue was dissolved in 5 ml chloroform. The solution of amine was stirred with 0.99 g anhydrous sodium carbonate and 1.4 g chloroacetonitrile (1.2 ml; 18.5 mmole) dissolved in 25 ml toluene. With stirring under nitrogen, the mixture was heated at 85° C. overnight. TLC of an aliquot of the reaction mixture indicated an incomplete conversion. A 10% excess of chloroacetonitrile was introduced along with 20 ml dimethyl formamide. The mixture was allowed to react at 35° C. for 30 min. The reaction was quenched with saturated aqueous sodium carbonate and the base was extracted with ether. The product was chromatographed on a 500 g alumina column packed in ether. Fractions of 75 ml were collected, and those containing product (11–16) were combined and taken to dryness. The solid residue (3 g; 11 mmole; 59.62%) was crystallized from cyclohexane. Yield: 2 g (74 mmole; 40.00%). Thin layer chromatography on silica gel in chloroform:methanol (9:1) $R_f$=0.9 and in hexane:ether:methanol. (70:30:1) $R_f$=0.09 indicated that this compound was pure. Mass spec. (ci MH+ =273), IR-CHCl$_3$ and NMR-CDCl$_3$ are consistent with the structure, m.p.=118°–119° C.

ANALYSIS: Calculated for $C_{16}H_{20}N_2O_2$: 70.55%C, 7.42%H, 10.28%N. Found: 70.84%C, 7.32%H, 10.21%N.

EXAMPLE 46

2-Methyl-1'-(2-phenylethyl)-spiro[2H-1,4-benzodioxepin-3(5H)4'-piperidine]hydrochloride The free base of 2-methylspiro[2H-1,4-benzodiozepin-3(5H)4'-piperidine] was liberated from 7.00 g (21.67 mmoles) of its oxalate, extracted into chloroform, dried over anhydrous potassium carbonate, filtered and taken to dryness. The residue was dissolved in 50 ml dry dimethylformamide and combined, under nitrogen, with 6.02 g 2-phenylethyl bromide (32.51 mmole, 4.44 ml) and 5.00 g sodium bicarbonate (6.00 mmole). The mixture was stirred overnight at ambient temperature, and was quenched with water and saturated sodium carbonate. This mixture was extracted with ether and the combined organic extracts were taken to dryness. This residue was loaded onto a 500 g alumina column packed in ether. While eluting with ether, 75 ml fractions were collected and those containing the purified material (7–11) were combined. The hydrochloride salt was precipitated, filtered and recrystallized from 2-propanol/methanol. Crop 1 afforded 2.1 g (5.62 mmole) material which appeared pure in the following thin layer chromatography systems: chloroform:methanol (9:1) on silica gel, $R_f$=0.65 and ether on alumina $R_f$=0.56. Mass Spec. (ci MH+ =338), IR-KBr and NMR-DMSO-$d_6$ are consistent with the structure. M.p.=264°–270° C.

ANALYSIS: Calculated for $C_{22}H_{27}NO_2HCl$: 70.66%C, 7.56%H, 3.74%N. Found: 70.69%C, 7.51%H, 3.38%N.

EXAMPLE 47

2-Methylspiro[2H-1,4-benzodioxepin-3(5H)4'-piperidine]-1'-acetic acid ethyl ester The compound 2-methylspiro[2H-1,4-benzodiozepin-3(5H)4'-piperidine]oxalate (8.8 g, 30.0 mmole) was converted to its free base with sodium carbonate and extracted into chloroform. The organic layer was dried over anhydrous potassium carbonate, filtered and taken to dryness. The residue was dissolved in 55 ml of anhydrous dimethylformamide. Ethyl bromoacetate (5.00 g, 3.1 ml) and potassium carbonate (8.3 g) were added to the resulting solution and allowed to react at room temperature overnight with stirring under nitrogen. The reaction mixture was quenched with water. The product was extracted with ether and dried over anhydrous potassium carbonate. The hydrochloride was precipitated and recrystallized from 2-propanol yielding 2.2 g (6 mmole, 20%) of 2-methylspiro[2H-1,4-benzodioxepin-3(5H)4'-piperidine]-1'-acetic acid ethyl ester hydrochloride which appeared pure by TLC on silica gel in chloroform:methanol (95:5) $R_f=0.5$ and in dichloromethane:methanol (1:1) $R_f=0.9$ MS (MH+ =320), NMR (DMSO-d$_6$) and IR (KBr) are consistent with structure, mp=200°–203° C.

ANALYSIS: Calculated for $C_{18}H_{26}ClNO_4$: 60.74%C, 7.38%H, 3.93%N. Found: 59.72%C, 7.35%H, 3.75%N.

EXAMPLE 48

1'-(2-Hydroxyethyl)-2-methylspiro[2H-1,4-benzodioxepin-3(5H)4'-piperidine]

The compound 2-methylspiro[2H-1,4-benzodioxepin-3(5H)4'-piperidine]-1'-acetic acid ethyl ester maleate (7.16 g, 16.44 mmole) was converted to its free base with sodium carbonate and extracted into chloroform. The organic layer was dried over anhydrous potassium carbonate, filtered and taken to dryness. The residue was dissolved in 160 ml anhydrous ether. Lithium aluminum hydride (0.39 g of a 50% mineral oil dispersion, 10.27 mmole) was suspended in 160 ml anhydrous ether and the temperature was raised to reflux. The ester solution was added at a dropwise rate to the refluxing LAH and after 15 min. at reflux, the reaction was determined to be complete by TLC. The mixture was cooled to ambient temperature and quenched with ethyl acetate. 20 ml 10% HCl was added and stirred for 10 min. The aqueous layer was brought to pH 8 with 15% sodium hydroxide. The aqueous phase was extracted with chloroform. All organic layers were combined and dried over anhydrous magnesium sulfate. This was filtered and the solvent was removed under vacuum resulting in an oily residue. The oil was loaded onto a 130 g alumina column packed in ether. Elution with ether in 20 ml fractions resulted in pure compound (fractions 7–15). The solvent was removed azeotropically with cyclohexane. The product crystallized resulting in 1.7 g (6.13 mmole, 37.29%) 1'-(2-hydroxyethyl)-2-methylspiro[2H-1,4-benzodioxepin-3(5H)4'-piperidine]. The product appeared pure by TLC on silica gel in chloroform:methanol (1:1), $R_f=0.4$ and in hexane:THF (1:1), $R_f=0.2$, Mass Spec. (ci MH+ =278), IR-CHCl$_3$ and NMR-CDCl$_3$ are consistent with the structure. m.p.=98°–101° C.

ANALYSIS: Calculated for $C_{16}H_{23}NO_3$: 69.27%C, 8.37%H, 5.05%N. Found: 69.23%C, 8.37%H, 4.75%N.

EXAMPLE 49

1'-(2-Aminoethyl)-2-methylspiro[2H-1,4-benzodioxepin-3(5H)4'-piperidine]dioxalate The compound 1'-cyanomethyl-2-methylspiro[2H-1,4-benzodioxepin-3(5H)4'-piperidine] (7.00 g, 25.74 mmole) dissolved in 100 ml THF was added dropwise, under nitrogen, to a stirred solution of borane in THF (65 ml, 65 mmole) at 0° C. After complete addition, the mixture was allowed to warm to ambient temperature and react overnight. The mixture was quenched with 33 ml 3N HCl and heated at reflux for 1 hour. After cooling to ambient temperature, this solution was brought to dryness in vacuo. The residue was suspended in 1% HCl and extracted with ether. The aqueous layer was made basic (pH~9) with 15% NaOH and was extracted with chloroform. After drying over anhydrous potassium carbonate and filtration, the dioxalate was precipitated. This material was recrystallized from boiling methanol/water. Crop 1 yielded 6.7 g (14.69 mmole, 57.07% yield) material. The material appeared pure by TLC on silica gel in chloroform:methanol (1:1) $R_f=0.1$ and in 2-propanol:ammonium hydroxide (7:3) $R_f=0.8$, Mass Spec. (CI MH+ =277), $^{13}$C-NMR-DMSO-d$_6$, NMR-DMSO-d$_6$, and IR-KBr are consistent with the structure; mp=195°–197° C.

ANALYSIS: Calculated for $C_{16}H_{24}N_2O_2.2C_2H_2O_4$: 52.62%C, 6.20%H, 6.13%N. Found: 52.24%C, 6.09%H, 5.98%N.

EXAMPLE 50

[2-(2-Methylspiro[2H-1,4-benzodioxepin-3(5H)4'-piperidin]-1'-yl)ethyl]-guanidine hemisulfate hemihydrate The compound 1'-(2-aminoethyl)-2-methylspiro[2H-1,4-benzodioxepin-3(5H)4'-piperidine]dioxalate (0.5 g; 1.1 mmole) was converted to its free base, extracted into chloroform and the solvent removed in vacuo. The residue was dissolved in 1.1 ml ethanol and diluted with 4.4 ml water. S-methyl-pseudothiourea (0.153 g; 0.55 mmole) was added and the mixture was heated at reflux under N$_2$ overnight. The reaction mixture was cooled to room temperature and diluted with 5 ml ethanol and 5 ml ether and refrigerated. The resultant crystals were filtered and vacuum dried at 50° C. yielding 266.3 mg product (0.71 mmole; 64.55%). The material appeared pure by TLC on alumina in 2-propanol:ammonium hydroxide (7:3), $R_f=0.7$ and in ethanol:ammonium hydroxide (29:1), $R_f=0.15$. Mass Spec. (ci MH+ =319), NMR (DMSO-d$_6$) and IR (KBr) are consistent with the structure; mp=218°–220° C.

ANALYSIS: Calculated for $C_{34}H_{56}N_8O_9S$: 54.38%C, 7.26%H, 14.29%N. Found: 54.04%C, 7.24%H, 14.60%N.

EXAMPLE 51

1'-Cyclopropylmethyl-2-methylspiro[2H-1,4-benzodioxepin-3(5H)4'-piperidine]oxalate The compound 2-methylspiro[2H-1,4-benzodioxepin-3(5H)4'-piperidine]oxalate (4.0 g, 17.2 mmole) was converted to its free base, extracted into chloroform and dried over anhydrous potassium carbonate. The solvent was removed in vacuo and the oily residue was dissolved in 35 ml DMF. To this mixture was added 4.4 g sodium bicarbonate, 4.4 g potassium iodide and 1.9 g α-chloromethylcyclopropane (20.6 mmole, 1.9 ml). The reactants were stirred under nitrogen at 45° C. overnight. The reaction was determined to be complete by TLC. The mixture was quenched with an equal volume of water and extracted with ether. The ether extracts were combined and the solvent removed in vacuo. The oily residue was loaded onto a 200 g alumina column packed in ether. Fractions of 50 ml each were collected, eluting with ether. Those fractions (5–7) containing the desired compound were combined and the oxalate was precipitated. The product was vacuum dried at 40° C. overnight affording 1.6 g solid (4.2 mmole, 25.7% yield) which appeared pure by TLC. Chromatography was done on silica gel in chloroform:methanol (9:1), $R_f=0.4$ and in hexane:ether:methanol (70:30:1), $R_f=0.1$. Mass Spec (ci MH+ =288), NMR-DMSO-d$_6$ and IR-KBr are consistent with the structure; mp=161°–164° C.

ANALYSIS: Calculated for $C_{20}H_{27}NO_6$: 63.63%C, 7.22%H, 3.71%N. Found: 63.48%C, 7.14%H, 3.47%N.

EXAMPLE 52

1'-[3-(6-Fluoro-1,2-benzisoxazol-3-yl)propyl]-2-methylspiro[2H-1,4-benzodioxepin-3(5H)4'-piperidine]maleate The compound 2-methylspiro[2H-1,4-benzodioxepin-3(5H)4'-piperidine]oxalate (3.9 g, 12.2 mmole) was converted to its free base, dried and dissolved in 25 ml DMF. Anhydrous potassium carbonate (2.5 g milled) was added to the mixture along with potassium iodide (15 mg) and 2.6 g (12.2 mmole) 3-(3-chloropropyl)-6-fluoro-1,2-benzisoxazole. The mixture was heated for 2 hrs at 70° C. under nitrogen with stirring. TLC indicated that the reaction was complete. The mixture was cooled to room temperature, diluted with an equal volume of water and extracted with ether. The ether extracts were combined and the volume reduced in vacuo. The residue was loaded onto an alumina column (200 g) packed in ether and eluted with ether in 20 ml fractions. The desired material was contained in fractions 6–14, which were combined. The maleate was precipitated and dried, yielding 2.5 g (4.6 mmole, 37.7%) solid. This material appeared pure by TLC on silica gel in chloroform:methanol (9:1), $R_f=0.45$ and in ether:ethanol (2:1), $R_f=0.30$. m.p. 170°–174° C. MS (ci $MH^+=411$), NMR-DMSO-$d_6$ and IR-KBr are consistent with the structure.

ANALYSIS: Calculated for $C_{28}H_{31}FN_2O_7$: 63.86%C, 5.95%H, 5.32%N. Found: 63.93%C, 5.99%H, 5.27%N.

EXAMPLE 53

2-Methyl-1'-[3-(2-methylindol-3-yl)propyl]spiro[2H-1,4-benzodioxepin-3(5H)4'-piperidine]fumarate The compound 2-methylspiro[2H-1,4-benzodioxepin-3(5H)4'-piperidine]oxalate (3.9 g, 12.2 mmole) was converted to its free base and was extracted into chloroform. The combined extracts were dried over magnesium sulfate and were filtered. The filtrate was reduced in volume in vacuo. The residue was dissolved in 25 ml DMF and was stirred with 4.3 g 3-(2-methylindol-3-yl)propyl benzenesulfonate (13.4 mmole). To the resultant mixture was added 2.5 g milled anhydrous potassium carbonate. The mixture was allowed to react at ambient temperature under nitrogen overnight. The reaction was determined complete by TLC and was quenched with 150 ml water. The mixture was extracted with ether. The ether extracts were combined and washed with saturated brine. The etherial layer was reduced in volume in vacuo and was loaded onto a 150 g alumina column packed in ether. Fractions of 50 ml were eluted and the desired product was in fraction numbers 3–6. These fractions were combined and the fumarate salt precipitated to provide 2-methyl-1'-[3-(2-methylindol-3-yl)propyl]spiro[2H-1,4-benzodioxepin-3(5H)4'-piperidine]fumarate (2 g, 3.84 mmole, 31.49% yield). The material appeared pure by TLC on silica gel in chloroform:methanol (9:1) $R_f=0.3$ and in dichloromethane:2-propanol (9:1) $R_f=0.1$. The MS (ci $MH^+=405$), NMR-CDCl$_3$ and IR-CHCl$_3$ are consistent with the structure, m.p. 110°–120° C.

ANALYSIS: Calculated for $C_{23}H_{25}N_2O_6$: 69.20%C, 6.98%H, 5.38%N. Found: 69.21%C, 7.03%H, 5.42%N.

EXAMPLE 54

2-Methyl-1'-pentylspiro[2H-1,4-benzodioxepin-3(5H)4'-piperidine]oxalate

The compound 2-methylspiro[2H-1,4-benzodioxepin-3(5H)4'-piperidine]oxalate (4.0 g, 12.4 mmole) was converted to its free base and was dried. The solvent was removed in vacuo and the residue was dissolved in DMF. Pentylbromide (2.1 g, 13.6 mmole), 2.5 g K$_2$CO$_3$ (milled, anhydrous) and 16 mg KI were added to the DMF solution. This mixture was stirred under nitrogen at ambient temperature overnight. The mixture was quenched with water and was extracted with ether. The solvent was removed in vacuo. The residue was loaded onto a 100 g alumina column packed in ether. The compound was eluted with ether in 50 ml fractions. The desired product was found in fractions 3–6. The oxalate salt was precipitated from the combined fractions. The solids were filtered and vacuum dried. The product (3.2 g, 8.14 mmole, 65.65%) appeared pure by TLC on silica gel in chloroform methanol (9:1) $R_f=0.35$ and in dichloromethane:2-propanol (1:1) $R_f=0.31$. MS (ci $MH^+=304$), NMR-DMSO-$d_6$ and IR(KBr) are consistent with the structure, m.p.=167°–170° C.

ANALYSIS: Calculated for $C_{21}H_{31}NO_6$: 64.09%C, 7.69%H, 3.56%N. Found: 64.12%C, 7.95%H, 3.51%N.

EXAMPLE 55

2-Methyl-1'-(3-aminopropyl)spiro[2H-1,4-benzodioxepin-3(5H)4'-piperidine]dioxalate The compound 1'-(2-cyanoethyl)-2-methylspiro[2H-1,4-benzodioxepin-3(5H)4'-piperidine]hydrochloride (4 g, 2.4 mmole) was converted to its free base and dried. After removal of solvent in vacuo, the residue was dissolved in 80 ml of a mixture of 50% THF in ether. This was added dropwise to 3.76 g of lithium aluminum hydride in 40 ml refluxing ether. The mixture was maintained at reflux overnight. The reaction mixture was cooled and quenched with 25 ml ethyl acetate. Subsequently, the resulting complex was broken by treating with 25 ml 10% HCl. Non-basic by-products were extracted into ether. The aqueous layer was basified with saturated sodium bicarbonate. The products were extracted into chloroform and were dried over potassium carbonate. The chloroform was removed in vacuo and the products were dissolved in ether. The dioxolate was precipitated and was recrystallized from 2-propanol/methanol. The crystallization afforded 2 g 2-methyl-1'-(3-aminopropyl)spiro[2H-1,4-benzodioxepin-3(5H)4'-piperidine]dioxalate (4.25 mmole; 24.27%) which appeared pure by TLC on silica gel in chloroform:methanol (1:1) $R_f=0.1$ and ethanol:ammonium hydroxide (7:3) $R_f=0.63$. MS ($MH^+=383$), NMR-DMSO-$d_6$ and IR-KBr are consistent with the structure.

M.p.=180°–183° C.

ANALYSIS: Calculated for $C_{21}H_{30}N_2O_{10}$: 53.60%C, 6.44%H, 5.95%N. Found: 53.75%C, 6.44%H, 5.83%N.

EXAMPLE 56

1'-[2-(4-Nitrophenyl)ethyl]2-methylspiro[2H-1,4-benzodioxepin-3(5H)4'piperidine]oxalate The compound 2-methylspiro[2H-1,4-benzodioxepin-3(5H)4'-piperidine]oxalate (10 g, 30.96 mmole) was converted to its free base and was dried. The residue was dissolved in 100 ml DMF and was stirred with 8 g 4-nitrophenylethyl bromide (34.80 mmole), 10 g $K_2CO_3$ (anhydrous, milled) and 20 mg KI. The mixture was allowed to react overnight at ambient temperature under a nitrogen atmosphere. By morning TLC showed that the reaction was complete. The mixture was quenched with water and the products were extracted into ether. The ether extracts were combined and washed with saturated brine. The ether was removed in vacuo and the solid residue was loaded onto an alumina column (200 g) packed in ether. Fractions of 100 ml were collected and the desired material was contained in fractions 3–10. These solutions were combined and the oxalate salt precipitated. The solid was recrystallized from ethanol-methanol resulting in 8.9 g 1'-[2-(4-nitrophenyl)ethyl]-2-methylspiro[2H-1,4-benzodioxepin-3(5H)4'-piperidine]oxalate (18.84 mmole, 60.85%). This material appeared pure by TLC on silica gel in chloroform:methanol (9:1), $R_f=0.6$ and in dichloromethane:2-propanol (1:1) $R_f=0.7$. MS (ci $MH^+=383$), NMR-DMSO-$d_6$ and IR-KBr are consistent with the structure, m.p 165°–171° C.(d).

ANALYSIS: Calculated for $C_{24}H_{28}N_2O_8$: 61.00%C, 5.98%H, 5.93%N. Found: 60.91%C, 5.88%H, 6.08%N.

EXAMPLE 57

1'-[2-(4-Aminophenyl)ethyl]-2-methylspiro[2H-1,4-benzodioxepin-3(5H)4'-piperidine]maleate hydrate The compound 1'-[2-(4-nitrophenyl)ethyl]-2-methylspiro[2H-1,4-benzodioxepin-3(5H)4'-piperidine]oxalate (6.7 g, 14.2 mmole) was converted to its free base and dried. The residue was dissolved in 60 ml ethanol and was mixed with 15 ml water, 0.4 ml concentrated HCl and 8.8 g electrolytically reduced iron powder. The reaction temperature was raised to reflux and was maintained there overnight. The reaction was determined complete by TLC. The mixture was filtered through celite and the filtrate was reduced in volume in vacuo. The residue was suspended in saturated aqueous sodium bicarbonate and was extracted with dichloromethane. The organic extracts were combined and reduced in volume in vacuo. The residue was passed through an alumina column (120 g) packed in ether. Fractions of 50 ml collected. Those fractions (2–8) containing the desired product were combined and the maleate salt was precipitated. The precipitate was recrystallized from ethanol resulting in pure product (2.8 g, 5.75 mmole, 40.49%). Purity was determined by TLC on silica gel in chloroform:methanol (9:1), $R_f=0.2$ and in dichloromethane:2-propanol (1:1), $R_f=0.2$, mp=120°–128° C.(d). MS (ci $MH^+=353$), NMR-DMSO-$d_6$, IR-KBr were consistent with the structure.

ANALYSIS: Calculated for $C_{26}H_{34}N_2O_7$: 64.17%C, 7.06%H, 5.75%N. Found: 64.31%C, 6.62%H, 5.46%N.

EXAMPLE 58

1'-[2-(N,N-dimethylamino)ethyl]-2-methylspiro[2H-1,4-benzodioxepin-3(5H)4'-piperidine]dihydrochloride The compound 2-methylspiro[2H-1,4-benzodioxepin-3(5H)4'-piperidine]oxalate (10 g, 30.96 mmole) was converted to its free base and dried. The residue was dissolved in 100 ml DMF and was combined with 4.9 g 2-(N,N-dimethylamino)ethylchloride hydrochloride (34.0 mmole), 10 g $K_2CO_3$ and 20 mg KI. The mixture was stirred at ambient temperature under nitrogen for 3 days. The reaction was quenched with water and was extracted with ether. The ether extracts were combined and back-extracted with saturated brine. The solvent was removed in vacuo and the residue was loaded onto a 200 g alumina column packed in ether. Elution was carried out using ether while 10 ml fractions were collected. The desired product was in fractions 3–5. These were combined and the hydrochloride salt precipitated. The crystals were filtered and vacuum dried affording 2.0 g 1'-[2-N,N-dimethylamino)ethyl]-2-methylspiro[2H-1,4-benzodioxepin-3(5H)4'-piperidine]dihydrochloride (5.31 mmole, 17.15%). This material appeared pure by TLC on silica gel in chloroform:methanol (1:1) $R_f=0.1$ and in ethanol:ammonium hydroxide (7:3), $R_f=0.6$. MS (ci $MH^+=305$). NMR-DMSO-$d_6$ and IR-KBr are consistent with the structure, m.p.=265°–270° C.(d).

ANALYSIS: Calculated for $C_{18}H_{30}Cl_2N_2O_2$: 57.28%C, 8.03%H, 7.42%N. Found: 57.58%C, 7.92%H, 7.29%N.

EXAMPLE 59

1'-[2-(1-Morpholino)ethyl]-2-methylspiro[2H-1,4-benzodioxepin-3(5H)4'-piperidine]dihydrochloride The compound 2-methylspiro[2H-1,4-benzodioxepin-3(5H)4'-piperidine]oxalate (1 g, 3.1 mmole) was converted to its free base and dried. The resultant oil was dissolved in 10 ml DMF and stirred overnight under nitrogen with 1 g $K_2CO_3$ (milled, anhydrous), 5 mg KI and 0.64 g 1-(2-chloroethyl)morpholine hydrochloride (3.4 mmole). The reaction was quenched with water and the products were extracted into ether. The organic phase was washed with saturated brine and the solvent was removed in vacuo. The oily residue was loaded onto a 15 g alumina column packed in ether. Collection of 5 ml fractions resulted in the isolation of the desired product in fraction numbers 2–4. These fractions were combined and the dihydrochloride salt was precipitated. After washing with ether and vacuum drying 870 mg 1'-[2-(1-morpholino)ethyl]-2-methylspiro[2H-1,4-benzodioxepin-3(5H)4'-piperidine]dihydrochloride (2.07 mmole, 66.77%) was isolated. This material appeared pure by TLC on silica gel in chloroform:methanol (9:1) $R_f=0.2$ and in 2-propanol:ammonia (9:1), $R_f=0.7$. MS ($MH^+=347$), NMR-TFA and IR-KBr are consistent with the structure, m.p.=265°–270° C.(d).

ANALYSIS: Calculated for $C_{20}H_{32}Cl_2N_2O_3$: 57.26%C, 7.70%H, 6.67%N. Found: 57.11%C, 7.49%H, 6.59%N.

EXAMPLE 60

2-Methyl-1'-[3-(1,3-dihydro-2-oxo-2H-benzimidazol-1-yl)propyl]spiro[2H-1,4-benzodioxepin-3(5H)4'-piperidine]

The compound 2-methylspiro[2H-1,4-benzodioxepin-3(5H)4'-piperidine]hydrochloride (5 g, 18.5 mmole) was converted to its free base and dried. The resultant oil was dissolved in 50 ml DMF and stirred under nigrogen with 5 g potassium carbonate (milled, anhydrous), 15 mg potassium iodide and 4.3 g 3-(1,3-dihydro-2-oxo-2H-benzimidazol-1-yl)propylchloride (20.4 mmole) at ambient temperature, overnight. The reaction was determined to be complete by TLC. The mixture was quenched with an equal volume of water, after which a solid precipitate formed. This mixture was filtered and the solids were recrystallized from methanol:water, affording 3.0 g 2-methyl-1'-[3-(1,3-dihydro-2-oxo-2H-benzimidazol-1-yl)propyl]spiro[2H-1,4-benzodioxepin-3(5H)4'-piperidine] (7.4 mmole, 39.7%). This product appeared pure by TLC on silica gel in chloroform:methanol (9:1), R$_f$=0.4 and in dichloromethane:ethanol (9:1), R$_f$=0.3. Mass Spec. (MH+ =408), NMR-CDCl$_3$ and IR-CHCl$_3$ are consistent with the structure, m.p.=129°-130° C.

ANALYSIS: Calculated for C$_{24}$H$_{29}$N$_3$O$_3$: 70.73%C, 7.19%H, 10.31%N. Found: 70.68%C, 7.55%H, 10.29%N.

EXAMPLE 61

2-Methyl-1'-[3-cyano-3,3-diphenylpropyl]spiro[2H-1,4-benzodioxepin-3(5H)4'-piperidine]hydrochloride The compound 2-methylspiro[2H-1,4-benzodioxepin-3(5H)4'-piperidine]hydrochloride (5 g, 18.55 mmole) was dissolved in 100 ml of DMF and stirred under nitrogen at 90° C. with 5 g of potassium carbonate (milled, anhydrous), 15 mg of potassium iodide, and 6.12 g of 4-bromo-2,2-diphenyl butyronitrile (20.4 mmole), overnight. The reaction was determined to be complete by TLC. The mixture was cooled to ambient temperature, quenched with water and extracted into ether. The ether extracts were washed with saturated brine and the solvent was removed under vacuum. The residue was loaded onto a 100 g alumina column packed in ether and 50 ml fractions were eluted. The desired material was found in fractions 2-5, which were subsequently combined. The hydrochloride was precipitated and recrystallized from 2-propanol resulting in 3.7 g 2-methyl-1'-[3-cyano-3,3-diphenylpropyl]spiro[2H-1,4-benzodioxepin-3(5H)4'-piperidine]hydrochloride (7.57 mmole, 40.78%), which appeared pure by TLC on silica gel in chloroform:methanol (9:1), R$_f$=0.7 and in dichloromethane:2-propanol (1:1), R$_f$=0.9. MS (MH+ =453), NMR-DMSO-d$_6$/TFA and IR-KBr are consistent with the structure, m.p.=254°-259° C.

ANALYSIS: Calculated for C$_{30}$H$_{33}$ClN$_2$O$_2$: 73.67%C, 6.81%H, 5.73%N. Found: 73.46%C, 6.57%H, 5.61%N.

EXAMPLE 62

1-Acetyl-4-(4-chloro-2-fluorobenzyloxy)-4-ethynylpiperidine

Sodium hydride (50% mineral oil dispersion, 10.7 g, 223 mmole) was suspended in 100 ml DMF. A solution of 1-acetyl-4-ethynyl-4-hydroxypiperidine (37.4 g, 0.223 mole) in 125 ml DMF was added to the sodium hydride suspension at 20° C. After the complete evolution of hydrogen gas, the solution was cooled to 5° C. and a mixture of 50 g 4-chloro-2-fluorobenzylbromide in 50 ml DMF was added dropwise. The temperature was not allowed to exceed 10° C. during the addition. The mixture was allowed to equilibrate to ambient temperature and after 2 hrs. the reaction was determined to be complete. The mixture was quenched with ice water and extracted with ether. The ether extracts were combined and dried over anhydrous magnesium sulfate. This was filtered and the solvent removed in vacuo. The oily residue was purified by preparative HPLC, eluting with hexane:ethylacetate (1:1). The material was contained in fractions 8-12. When combined and the solvent removed, these fractions afforded 52.6 g 1-acetyl-4-(4-chloro-2-fluorobenzyloxy)-4-ethynylpiperidine (170 mmole, 76.23%). This material appeared pure by TLC on silica gel in chloroform:methanol (9:1), R$_f$=0.6 and in hexane:ethylacetate (1:1) R$_f$=0.2, MS(MH+ =310), NMR-CDCl$_3$ and IR-CHCl$_3$ are consistent with the structure; mp=70°-74° C.

ANALYSIS: Calculated for C$_{16}$H$_{17}$ClFNO$_2$: 62.03%C, 5.54%H, 4.52%N. Found: 62.25%C, 5.42%H, 4.48%N.

EXAMPLE 63

4-(4-Chloro-2-fluorobenzyloxy)-4-(1-oxoethyl)-piperidine maleate

The compound 1-acetyl-4-(4-chloro-2-fluorobenzyloxy)-4-ethynylpiperidine (40.2 g, 130 mmole) was suspended in 400 ml of 10% H$_2$SO$_4$. The mixture was heated to reflux until complete dissolution was observed (indicating complete hydrolysis of the acetamide). The mixture was cooled and 5 g mercuric sulfate was added. The hydrolysis of the acetylene was followed by IR spectroscopy. When complete, the mixture was cooled and quenched by pouring into a mixture of ice, water and sodium bicarbonate. The basic mixture was extracted with chloroform. The organic extracts were combined, dried over anhydrous magnesium sulfate and filtered. The solvent was removed from the filtrate and the residue dissolved in a chloroform:ether mixture. The maleate was precipitated and recrystallized from ethanol. Yield: 27 g (70 mmole, 53.8%). The material appeared pure by TLC on silica gel in chloroform:methanol (9:1) R$_f$=0.10 and in ethanol:ammonium hydroxide (27:3) R$_f$=0.75. Mass Spec (ci MH+ =286), NMR-DMSO-d$_6$ and IR-KBr are consistent with the structure; mp=139°-142° C.

ANALYSIS: Calculated for C$_{18}$H$_{21}$ClFNO$_6$: 53.80%C, 5.28%H, 3.48%N. Found: 53.39%C, 5.23%H, 3.45%N.

EXAMPLE 64

4-(4-Chloro-2-fluorobenzyloxy)-4-(1-hydroxyethyl)-piperidine oxalate

The compound 4-(4-chloro-2-fluorobenzyloxy)-4-(1-oxoethyl)piperidine (20.6 g, 72 mmole) in 50 ml methanol was added dropwise to a solution of sodium borohydride (6.8 g, 180 mmole) in 50 ml methanol at 5° C. The mixture was allowed to slowly reach ambient temperature while stirring under nitrogen overnight. Subsequently, the mixture was stirred for ½ hr with 5 ml 10% HCl. The solvent was removed in vacuo. The residue was suspended in water, made basic with saturated aqueous sodium bicarbonate. This mixture was extracted with chloroform. The organic extracts were combined, dried over magnesium sulfate and filtered. The solution was diluted with an equal volume of anhydrous ether and the oxalate salt precipitated. The solid was recrystallized from ethanol/methanol, yielding a crop of crystals (8.0 g, 0.02 mole, 29.2%) of 4-(4-chloro-2-fluorobenzyloxy)-4-(1-hydroxyethyl)piperidine oxalate. A second crop was obtained yielding 2.3 g more (6 mmole, 8.3%). The overall yield was 37.5% of material that appeared pure by TLC on silica gel in chloroform:methanol (1:1) R$_f$=0.1 and in ethanol:ammonium (7:3) R$_f$=0.6. Mass Spec (ci MH+ =288), NMR-DMSO-d$_6$ and IR-KBr are consistent with the structure; mp=172°-174° C.

ANALYSIS: Calculated for C$_{16}$H$_{21}$ClFNO$_6$: 50.86%C, 5.61%H, 3.71%N. Found: 50.72%C, 5.57%H, 3.59%N.

EXAMPLE 65

8-Chloro-2-methylspiro[2H-1,4-benzodioxepin-3(5H)4′-piperidine]oxalate

The compound 4-(4-chloro-2-fluorobenzyloxy)-4-(1-hydroxyethyl)piperidine (3.6 g, 12.5 mmole) in 15 ml DMSO was added dropwise to a solution of dimsyl sodium (12.5 mmole) in 15 ml DMSO at 10° C. The extent of conversion to produce was monitored by GLC (3% ASI; 230° C.; 45 ml/min). After stirring overnight at ambient temperature, the product ratio had not changed from the previous 60% conversion. An additional 12.5 mmole aliquot of dimsyl sodium in 5 ml DMSO was added, and within 40 min. the conversion to product was 98% complete. The reaction mixture was quenched with iced water and 10 ml 10% HCl. The mixture was extracted with ether. The aqueous layer was made basic (pH≃8) with 10% NaOH. The mixture was extracted with ether and the organic extracts of the basic mixture combined, dried over $K_2CO_3$ and filtered. The oxalate was precipitated (4 g, 11.2 mmole, 89.6%). The product was recrystallized from methanol/water and appeared pure by TLC on silica gel in chloroform:methanol (1:1), $R_f=0.2$ and in ethanol:ammonium hydroxide (7:3), $R_f=0.8$, and was >98% pure by GLC (conditions previously stated), m.p.=220°-222° C. MS (ci MH+ =268), NMR-DMSO-$d_6$ and IR-KBr are consistent with the structure.

ANALYSIS: Calculated for $C_{16}H_{20}ClNO_6$: 53.70%C, 5.65%H, 3.91%N. Found: 54.04%C, 5.73%H, 3.93%N.

EXAMPLE 66

8-Chloro-1′-cyanomethyl-2-methylspiro[2H-1,4-benzodioxepin-3(5H)4′-piperidine]

The compound 8-chloro-2-methylspiro[2H-1,4-benzodioxepin-3(5H)4′-piperidine]oxalate (5 g, 14.00 mmole) was converted to its free base, extracted into chloroform, dried over anhydrous potassium carbonate and filtered. The solvent was removed in vacuo and the oily residue dissolved in 50 ml DMF. To this solution was added 5 g $Na_2CO_3$ (milled, anhydrous), 0.05 KI and 2.11 g chloroacetonitrile (27.9 mmole). The mixture was allowed to react overnight at ambient temperature under nitrogen. The reaction was determined complete by TLC. The mixture was quenched with an equal volume of water and extracted with ether. The organic extracts were combined, dried over $K_2CO_3$ (anhydrous) and filtered. The solvent was removed in vacuo, resulting in crystalline product (2.5 g, 8,17 mmole, 58.36%). The product recrystallized from cyclohexane-toluene resulted in material that appeared pure by TLC on $SiO_2$ in chloroform:methanol (9:1) $R_f=0.73$ and hexane/ethylacetate (1:1) $R_f=0.18$. Mass Spec (ci MH+ =307), NMR-CDCl$_3$, and IR-CHCl$_3$ are consistent with the structure. m.p.=165°-166° C.

ANALYSIS: Calculated for $C_{16}H_{19}ClN_2O_2$: 62.63%C, 6.25%H, 9.13%N. Found: 62.45%C, 6.22%H, 8.92%N.

EXAMPLE 67

1′-(2-Cyanoethyl)-2-methylspiro[2H-1,4-benzodioxepin-3(5H)4′-piperidine]oxalate

The compound 2-methylspiro[2H-1,4-benzodioxepin-3(5H)4′-piperidine]oxalate (4 g, 12.4 mmole) was converted to its free base and dried. The oily residue was stirred with acrylonitrile (0.73 g, 13.6 mmole, 0.9 ml) in the dark overnight. The reaction mixture was diluted with anhydrous ether, after which a precipitate formed. The solids were filtered off and the oxalate precipitated. The material was crystallized from ethanol-methanol yielding two crops, each weighing 2 g (4 g, 10.64 mmole, 85.81%). The material appeared pure by TLC on silica gel in chloroform:methanol (9:1) $R_f=0.65$ and in ether:ethanol (2:1), $R_f=0.55$. Mass Spec (ci MH+ =287), NMR-DMSO-$d_6$ and IR-KBr are consistent with the structure, m.p.=154°-158° C.

ANALYSIS: Calculated for $C_{19}H_{24}N_2O_6$: 60.62%C, 6.44%H, 7.44%N. Found: 60.74%C, 6.31%H, 7.37%N.

EXAMPLE 68

1′-Cyano-2-methylspiro[2H-1,4-benzodioxepin-3(5H)4′-piperidine]

The compound 2-methylspiro[2H-1,4-benzodioxepin-3(5H)4′-piperidine]hydrochloride (5 g, 18.6 mmole) was suspended in 100 ml of chloroform along with 2.0 g of cyanogen bromide (18.8 mmole) and 5.0 g of milled, anhydrous potassium carbonate. The mixture was stirred under nitrogen at reflux for 48 hr. The resultant mixture was cooled to room temperature, filtered, and taken to dryness on a rotary evaporator. Solids were dissolved in hexane:ethyl acetate (1:1) and run through a 50 g silica gel column packed in the same solvent system. Fractions of 30 ml were collected and the desired material was found in numbers 5-7. These were combined and taken to dryness. The crystalline material was recrystallized from hexane-ethyl acetate resulting in 2.7 g of 1′-cyano-2-methylspiro[2H-1,4-benzodioxepin-3(5H)4′-piperidine] (10.5 mmole, 56.5%) which appeared pure by TLC on silica gel in hexane:ethyl acetate (1:1), $R_f=0.7$ and by GLC (OV-17, 250° C., 30 ml/min $t_R=2.92$), MS (M+ =259-internal CI), NMR (DMSO-$d_6$) and IR (CHCl$_3$) are consistent with the structure, mp=127°-130° C.

ANALYSIS: Calculated for $C_{15}H_{18}N_2O_2$: 69.74%C, 7.04%H, 10.84%N. Found: 67.70%C, 7.08%H, 10.85%N.

EXAMPLE 69

2-Methylspiro[2H-1,4-benzodioxepin-3(5H)4′-piperidine]-1′-carboximidic acid, methyl ester hydrochloride The compound 1′-cyano-2-methylspiro[2H-1,4-benzodioxepin-3(5H)4′-piperidine] (5 g, 19.4 mmole) was dissolved in 20 ml of methanol and was stirred at ambient temperature under nitrogen with 0.48 ml of a 25% sodium methoxide solution in methanol (2.1 mmole). After heating at reflux for 2 hr. the reaction was determined to be complete by TLC. The mixture was cooled, quenched with water and extracted into ethyl acetate. The organic phase was dried over $K_2CO_3$, filtered and taken to dryness under vacuum. The oily residue was dissolved in anhydrous ether from which the hydrochloride salt was precipitated. The solids were filtered and recrystallized from ethyl acetate-methanol resulting in 2.0 g of 2-methylspiro[2H-1,4-benzodioxepin-3(5H)4′-piperidine]-1′-carboximidic acid, methyl ester hydrochloride (6.13 mmole, 31.6%) which appeared pure by TLC on silica gel in butanol:acetic acid:water (4:1:1), $R_f=0.4$ and in ethanol:ammonium hydroxide (7:3) $R_f=0.7$. MS (M+ =291 (internal CI)), NMR (CDCl$_3$) and IR (KBr) are consistent with the structure, mp=152°-157° C.(d).

ANALYSIS: Calculated for $C_{16}H_{23}ClN_2O_3$: 58.79%C, 7.11%H, 8.57%N. Found: 59.04%C, 7.04%H, 8.53%N.

EXAMPLE 70

N,2-Dimethylspiro[2H-1,4-benzodioxepin-3(5H)4'-piperidine]-1'-carboxamide

The compound 2-methylspiro[2H-1,4-benzodioxepin-3(5H)4'-piperidine]hydrochloride (6.0 g, 22.3 mmole) was converted to its free base, dried and dissolved in 50 ml of benzene. Methylisocyanate (1.3 g, 23.4 mmole) was added in 10 ml of benzene to the above solution. Since a slight exotherm was observed, the mixture was cooled in a 5° C. water bath. The reaction mixture was stirred at ambient temperature overnight under nitrogen. TLC indicated complete reaction. The product, which crystallized from the mixture, was filtered and recrystallized from benzene. The resultant 2.4 g of N,2-dimethylspiro[2H-1,4-benzodioxepin-3-(5H)4'-piperidine]-1'-carboxamide (8.3 mmole, 37.1%) appeared pure by TLC on silica gel in dichloromethane:methanol (9:1), $R_f=0.5$ and in hexane:ethyl acetate:methanol (10:10:1), $R_f=0.3$. MS (MH+ =291), NMR (DMSO-d$_6$) and IR (KBr) are consistent with the structure, mp=150°–153° C.

ANALYSIS: Calculated for $C_{16}H_{22}N_2O_3$: 66.18%C, 7.65%H, 9.64%N. Found: 66.39%C, 7.50%H, 9.65%N.

EXAMPLE 71

N-Ethyl-2-methylspiro[2H-1,4-benzodioxepin-3(5H)4'-piperidine]-1'-carboxamide

The compound 2-methylspiro[2H-1,4-benzodioxepin-3(5H)4'-piperidine]hydrochloride (6.0 g, 22.3 mmole) was converted to its free base, dried and dissolved in 50 ml of benzene. To this solution was added 1.7 g of ethyl isocyanate (23.4 mmole). The mixture was allowed to react at ambient temperature under nitrogen overnight. TLC indicated that the reaction was complete. The product, which precipitated out of benzene, was filtered and recrystallized from benzene. The first crop was 2.0 g, 6.6 mmole, 29.6%. The benzene solutions were combined and taken to dryness under vacuum. The resultant solids were recrystallized from cyclohexane:ethyl acetate:ethanol yielding 3.0 g of N-ethyl-2-methylspiro[2H-1,4-benzodioxepin-3(5H)4'-piperidine]-1'-carboxamide (9.9 mmole, 44.4%) which appeared pure by TLC on silica gel in dichloromethane:methanol (9:1), $R_f=0.6$ and in hexane:ethyl acetate:methanol (10:10:1), $R_f=0.4$. MS (MH+ =305), NMR(CDCl$_3$) and IR (CHCl$_3$) are consistent with the structure, mp=160°–164° C.

ANALYSIS: Calculated for $C_{17}H_{24}N_2O_3$: 67.07%C, 7.96%H, 9.20%N. Found: 67.19%C, 7.96%H, 9.09%N.

EXAMPLE 72

2-Methylspiro[2H-1,4-benzodioxepin-3(5H)4'-piperidine]-1'-carboximidic acid, ethyl ester hydrochloride The compound 1'-cyano-2-methylspiro[2H-1,4-benzodioxepin-3(5H)4'-piperidine] (5.0 g, 19.4 mmole) was dissolved in a sodium ethoxide solution which was prepared by reacting 0.05 g of sodium metal (3.1 mmole) in 20 ml of ethanol. The mixture was heated at reflux temperature for 1 hr. at which time TLC indicated that the reaction was complete. The mixture was cooled to room temperature, and quenched with saturated aqueous $K_2CO_3$ and extracted with ethyl acetate. The organic extracts were dried over $K_2CO_3$, filtered, and taken to dryness under vacuum. The oily residue was dissolved in ether from which the hydrochloride was precipitated. Recrystallization from ethyl acetate-ethanol resulted in 2.0 g of 2-methylspiro[2H-1,4-benzodioxepin-3(5H)4'-piperidine]-1'-carboximidic acid, ethyl ester hydrochloride (5.9 mmole, 30.3%) which appeared pure by TLC on silica gel in butanol:acetic acid:water (4:1:1), $R_f=0.3$ and in ethanol:ammonium hydroxide (7:3), $R_f=0.6$. MS(MH+ =305), NMR (CDCl$_3$) and IR (CHCl$_3$) are consistent with the structure, mp=148°–151° C.(d).

ANALYSIS: Calculated for $C_{17}H_{25}ClN_2O_3$: 59.90%C, 7.41%H, 8.21%N. Found: 59.29%C, 7.20%H, 8.16%N.

EXAMPLE 73

1'-Acetyl-2-methylspiro[2H-1,4-benzodioxepin-3(5H)4'-piperidine]

The compound 2-methylspiro[2H-1,4-benzodioxepin-3(5H)4'-piperidine]hydrochloride (10.0 g, 37.1 mmole) was dissolved in 200 ml of acetic anhydride and stirred with 2.0 g of sodium acetate. The mixture was heated at 110° C. for 1 hr. GLC indicated quantitative conversion to product. The mixture was cooled and quenched with ice and saturated aqueous sodium carbonate. The product was extracted into dichloromethane, dried over potassium carbonate and filtered. The dichloromethane was removed under vacuum. The solid residue was recrystallized from cyclohexane/ethyl acetate resulting in 6.6 g of 1'-acetyl-2-methylspiro[2H-1,4-benzodioxepin-3(5H)4'-piperidine] (24.0 mmole, 64.7%) which appeared pure by TLC on silica gel in dichloromethane:methanol (9:1), $R_f=0.7$, and by GLC (OV-225 T=250° C., flow=30 ml/min, $t_R=2.49$ min). MS (CiMH+ =276), NMR-DMSOd$_6$ and IR-CHCl$_3$ are consistent with the structure, mp=135°–139° C.

ANALYSIS: Calculated for $C_{16}H_{21}NO_3$: 69.78%C, 7.70%H, 5.08%N. Found: 70.03%C, 7.72%H, 4.73%N.

EXAMPLE 74

1'-(4,4-Diphenylbutyl)-9-chloro-2-methylspiro[2H-1,4-benzodioxepin-3(5H)4'-piperidine]hydrochloride The compound 2-methylspiro[2H-1,4-benzodioxepin-3(5H)4'-piperidine]hydrochloride (31.2 g, 115.8 mmole) was dissolved in 1100 ml of methanol and heated at reflux temperature along with 17.0 g of N-chlorosuccinimide (127.4 mmole) for 1.0 hr. The mixture was cooled to ambient temperature and the solvent was removed under vacuum. The residue was suspended in saturated aqueous sodium bicarbonate and extracted with ether. The ether extracts were combined, dried over $K_2CO_3$ and filtered, from which the hydrochloride salts were precipitated. The salts were filtered, washed with ether and vacuum dried, resulting in 28.2 g (94.7 mmole, 81.8%) of the mixture of the two chloro isomers.

An aliquot of 18 g of the above mixture was dissolved in 300 ml of DMF and stirred under nitrogen with 20 g of milled anhydrous potassium carbonate, 15.9 g of 4,4-diphenylbutyl chloride (65.1 mmole) and 40 mg potassium iodide. The temperature was maintained at 80° C. overnight. The reaction mixture was cooled, quenched with an equal volume of water and extracted with ether. The ether extracts were combined, taken to dryness and loaded onto a 500 g alumina column packed in ether. Fractions of 200 ml were collected and the desired material was found in numbers 2–7, which were subsequently combined. The solvent was removed and the residue dissolved in ether. The hydrochloride salts were precipitated and recrystallized from toluene:ethyl acetate:ethanol resulting in 12.5 g (24.4 mmole, 41.1%) of a mixture of isomers: 80% of 1′-(4,4-diphenylbutyl)-7-chloro-2-methylspiro[2H-1,4-benzodioxepin-3(5H)4′-piperidine]hydrochloride and 20% of 1′-(4,4-diphenylbutyl)-9-chloro-2-methylspiro[2H-1,4-benzodioxepin-3(5H)4′-piperidine]hydrochloride as determined by HPLC (Waters-$C_{18}$ µ-Bondapak, 65% acetonitrile/35% 0.05M ammonium citrate, flow=3.0 ml/min, $t_R$=3.3 min. (9-Cl), 3.5 min. (7-Cl), uv detection λ=265 nm).

A sample of 8.52 grams of a mixture of 1-(4,4-diphenylbutyl)-9-chloro-2-methylspiro[2H-1,4-benzodioxepin-3(5H)4′-piperidine]hydrochloride and 1-(4,4-diphenylbutyl)-7-chloro-2-methylspiro[2H-1,4-benzodioxepin-3(5H)4′-piperidine]hydrochloride was converted to a mixture of the free bases (dichloromethane/saturated sodium carbonate). The mixture was isolated by chromatography using a Waters Prep 500 HPLC (eluents: 187/13/10/2, hexane/ethyl acetate/methanol/ammonium hydroxide→180/20/10/2→160/40/10/2. Fractions 49, 50 and 51 were combined. Evaporation of solvent provided an oil, the hydrochloride of which was analytically pure 1′-(4,4-diphenylbutyl)-9-chloro-2-methylspiro[2H-1,4-benzodioxepin-3(5H)4′-piperidine]hydrochloride, mp 194°–196°. The material appeared pure by TLC on silica gel: (150/50/10/2, hexane/ethyl acetate/methanol/ammonium hydroxide) (10% methanol/dichloromethane), $R_f$=0.5; and on analytical HPLC using a Waters µ Bondapak $C_{18}$ column, mobile phase: 65/35 acetonitrile/0.05M ammonium citrate, flow 1.5 ml/min., detector:UV at 265 nm. IR (KBr), NMR (DMSO-$d_6$), CMR (DMSO-$d_6$) and mass spectra (M+ =476) are consistent with the assigned structure.

ANALYSIS: Calculated for $C_{30}H_{34}ClNO_2 \cdot HCl$: 70.30%C, 6.90%H, 2.73%N. Found: 70.72%C, 6.85%H, 2.72%N.

EXAMPLE 75

1′-[4,4-Bis(3-fluorophenyl)butyl]-2-methylspiro[2H-1,4-benzodioxepin-3(5H)4′-piperidine]hydrochloride The compound 2-methylspiro[2H-1,4-benzodioxepin-3(5H)4′-piperidine]hydrochloride (5.0 g, 18.6 mmole) was suspended in 100 ml of n-butylacetate along with 5.0 g of potassium carbonate (milled, anhydrous), 15 mg of potassium iodide and 5.2 g of 4,4-bis(3-fluorophenyl)butyl chloride (18.6 mmole). The mixture was heated at reflux for 48 hr. under nitrogen. The reaction mixture was cooled to ambient temperature, filtered and the solvent removed under vacuum. The residual oil was loaded onto a 100 g alumina column packed in ether. Fractions of 50 ml were collected and the desired product was found in numbers 2–4. These were combined and dried under vacuum. The oily residue was dissolved in anhydrous ether and the hydrochloride salt precipitated The solids were recrystallized from ethyl acetate/ethanol yielding 4.1 g of 1′-[4,4-bis(3-fluorophenyl)butyl]-2-methylspiro[2H-1,4-benzodioxepin-3(5H)4′-piperidine]hydrochloride (8.0 mmole, 43.0%) which appeared pure by TLC on silica gel in hexane:ethyl acetate:methanol:ammonium hydroxide (10:10:1:0.1), $R_f$=0.7 and by HPLC (Waters-$C_{18}$ µ-Bondapak, 65% acetonitrile:35% 0.05M ammonium citrate, flow=2.0 ml/min, $t_R$=3.9 min, UV detection λ=265 nm.). MS (ciMH+ =478), NMR-DMSO-$d_6$ and IR-KBr are consistent with the structure, mp=207°–209° C.

ANALYSIS: Calculated for $C_{30}H_{34}ClF_2NO_2$: 70.10%C, 6.67%H, 2.72%N. Found: 70.02%C, 6.69%H, 2.67%N.

EXAMPLE 76

1′-[4,4-Bis(3-fluorophenyl)butyl]-7-fluoro-2-methylspiro[2H-1,4-benzodioxepin-3(5H)4′-piperidine]hydrochloride The compound 7-fluoro-2-methylspiro[2H-1,4-benzodioxepin-3(5H)4′-piperidine]hydrochloride (5.0 g, 17.4 mmole) was suspended in 100 ml of n-butylacetate along with 5.0 g of milled, anhydrous potassium carbonate, 15 mg of potassium iodide and 4.9 g of 4,4-bis(3-fluorophenyl)butylchloride (17.4 mmole). The mixture was heated at reflux for 48 hr. under nitrogen. The reaction mixture was cooled to ambient temperature, filtered and taken to dryness under vacuum. The oily residue was loaded onto a 100 g alumina column packed in ether. Fractions of 50 ml were collected and the desired material was found in numbers 2–4. These were combined and reduced in volume under vacuum. The residual oil was dissolved in anhydrous ether and the hydrochloride salt precipitated. The solids were recrystallized from ethyl acetate/ethanol yielding 5.7 g of 1′-[4,4-bis(3-fluorophenyl)butyl]-7-fluoro-2-methylspiro[2H-1,4-benzodioxepin-3(5H)4′-piperidine]hydrochloride (10.7 mmole, 61.5%) which appeared pure by TLC on silica gel in hexane:ethyl acetate:methanol:ammonium-hydroxide (10:10:1:0.1) $R_f$=0.7 and by HPLC (Waters-$C_{18}$ µ-Bondapak, 65% acetonitrile:35% 0.05M ammonium citrate, flow=2.0 ml/min, $t_R$=4.1 min, UV detection λ=265 nm). MS (ci MH+ =496), NMR-DMSO-$d_6$ and IR-KBr are consistent with the structure, mp=184°–187° C.

ANALYSIS: Calculated for $C_{30}H_{33}ClF_3NO_2$: 67.73%C, 6.25%H, 2.63%N. Found: 67.53%C, 6.29%H, 2.55%N.

EXAMPLE 77

1′-[4-(4-Fluorophenyl)butyl]-7-fluoro-2-methylspiro[2H-1,4-benzodioxepin-3(5H)4′-piperidine]hydrochloride The compound 7-fluoro-2-methylspiro[2H-1,4-benzodioxepin-3(5H)4′-piperidine]hydrochloride (5.0 g, 17.4 mmole) was suspended in 100 ml of n-butylacetate, along with 5.0 g of milled, anhydrous potassium carbonate, 15 mg of potassium iodide and 3.3 g of 4-(4-fluorophenyl)butyl chloride (17.4 mmole). The mixture was heated at reflux with stirring for 48 hr. under nitrogen. The reaction mixture was cooled, filtered and taken to dryness under vacuum. The residual oil was loaded onto a 100 g alumina column packed in ether. Fractions of 50 ml were collected and the desired product was found in numbers 2–4. These were combined and taken to dryness under vacuum. The oily residue was dissolved in anhydrous ether and the hydrochloride precipitated. The solids were recrystallized from ethyl acetate/ethanol yielding 4.0 g of 1′-[4-(4-fluorophenyl)butyl]-7-fluoro-2-methylspiro[2H-1,4-benzodioxepin-3(5H)4′-piperidine]hydrochloride (9.2 mmole, 52.6%) which appeared pure by TLC on silica gel in hexane:ethyl acetate:methanol:ammonium hydroxide (10:10:1:0.1), $R_f$=0.5 and by HPLC (Water's-$C_{18}$ µ-Bondapak, 65%, acetonitrile/35% 0.05M ammonium citrate, flow=2.0 ml/min, $t_R$=3.1 min, UV detection λ=265 nm). MS (ci MH+ =402), NMR-DMSOd6 and IR-CHCl3 are consistent with the structure, mp=201°-205° C.

ANALYSIS: Calculated for $C_{24}H_3ClF_2NO_2$: 65.82%C, 6.90%H, 3.20%N. Found: 65.83%C, 7.04%H, 3.30%N.

EXAMPLE 78

1'-[4-(4-Fluorophenyl)butyl]-7-chloro-2-methylspiro[2H-1,4-benzodioxepin-3(5H)4'-piperidine]hydrochloride The compound 7-chloro-2-methylspiro[2H-1,4-benzodioxepin-3(5H)4'-piperidine]hydrochloride (5.0 g, 16.4 mmole) was suspended in 100 ml of n-butylacetate along with 5.0 g of milled anhydrous potassium carbonate, 15 mg of potassium iodide and 3.2 g of 4-(4-fluorophenyl)butylchloride (17.2 mmole). The mixture was stirred at reflux for 48 hr. under nitrogen. The reaction mixture was cooled to ambient temperature, filtered and the solvent removed under vacuum. The oily residue was loaded onto a 100 g alumina column packed in ether. Fractions of 50 ml were collected and the desired product was found in numbers 2–4. These were combined and taken to dryness under vacuum. The residual oil was dissolved in anhydrous ether and the hydrochloride salt precipitated. The solids were recrystallized from ethyl acetate/ethanol yielding 5.3 g of 1'-[4-(4-fluorophenyl)butyl]-7-chloro-2-methylspiro[2H-1,4-benzodioxepin-3(5H)4'-piperidine]hydrochloride (11.7 mmole, 71.3%) which appeared pure by TLC on silica gel in hexane:ethyl acetate:methanol:ammonium hydroxide (10:10:1:0.1) $R_f$=0.5 and by HPLC (Water's-$C_{18}$ μ-Bondapak, 65% acetonitrile/35% 0.05M ammonium citrate, flow=2.0 ml/min, $t_R$=3.6 min, UV detection λ=265 nm). MS (ci MH+ =418), NMR-DMSO-$d_6$ and IR-CHCl3 are consistent with the structure, mp=213°-216° C.

ANALYSIS: Calculated for $C_{24}H_{30}Cl_2FNO_2$: 63.44%C, 6.65%H, 3.08%N. Found: 63.14%C, 6.71%H, 3.16%N.

EXAMPLE 79

1'-[4,4-Bis(3-fluorophenyl)butyl]-7-chloro-2-methylspiro[2H-1,4-benzodioxepin-3(5H)4'-piperidine]hydrochloride The compound 7-chloro-2-methylspiro[2H-1,4-benzodioxepin-3-(5H)4'-piperidine]hydrochloride (5.0 g, 16.4 mmole) was suspended in 100 ml of n-butylacetate and stirred along with 5.0 g of potassium carbonate (milled, anhydrous), 15 mg of potassium iodide and 4.6 g of 4,4-bis(3-fluorophenyl)butylchloride (16.4 mmole) under nitrogen. The mixture was heated at reflux for 48 hr. After cooling to ambient temperature, the mixture was filtered and taken to dryness under vacuum. The oily residue was loaded onto a 100 g alumina column packed in ether. Fractions of 50 ml were collected and desired material was found in numbers 2–4. These were combined and taken to dryness under vacuum. The residual oil was dissolved in anhydrous ether and the hydrochloride salt precipitated. The solids were recrystallized from ethyl acetate/ethanol resulting in 4.6 g of 1'-[4,4-bis(3-fluorophenyl)butyl]-7-chloro-2-methylspiro[2H-1,4-benzodioxepin-3(5H)4'-piperidine]hydrochloride (8.4 mmole, 49.0%). This material appeared pure by TLC on silica gel in hexane:ethyl acetate: methanol:ammonium hydroxide (10:10:1:0.1), $R_f$=0.7 and by HPLC (Water's-$C_{18}$ μ-Bondapak 65% acetonitrile 35% 0.05M ammonium citrate, flow=2.0 ml/min, $t_R$=5.0 min, UV detection λ=265 nm). MS (ci MH+ =512), NMR-DMSOd6 and IR-KBr are consistent with the structure, mp=186°-188° C.

ANALYSIS: Calculated for $C_{30}H_{33}Cl_2F_2NO_2$: 65.68%C, 6.08%H, 2.55%N. Found: 65.63%C, 6.10%H, 2.44%N.

EXAMPLE 80

1'-Acetyl-2-methyl-7-nitrospiro[2H-1,4-benzodioxepin-3(5H)4'-piperidine]

Sodium nitrite (0.4 g) was dissolved in 100 ml of nitric acid (70%) which had been cooled to −10° C. under nitrogen in a 500 ml round bottom flask. 1'-Acetyl-2-methylspiro[2H-1,4-benzodioxepin-3(5H)4'-piperidine] (20 g, 72.7 mmole) was added as a solid as to keep the reaction temperature below −5° C. After a reaction time of 1.5 hr. and slowly warming to a final temperature of +10° C. the reaction was determined complete by TLC. The mixture was poured into 1000 ml of iced water and extracted several times with ether (total volume=2.5 liters). The yellow colored organic phase was dried over potassium carbonate, filtered and taken to dryness. The oily residue was purified by flash chromatography on silica gel in hexane:ethyl acetate:methanol (10:15:0.5). Fractions of 100 ml were collected with the desired compound isolated in numbers 10–22. These were combined and taken to dryness. The solid residue was recrystallized from methanol yielding 4.4 g of 1'-acetyl-2-methyl-7-nitrospiro[2H-1,4-benzodioxepin-3(5H)4'-piperidine] (13.8 mmole, 19.0%) which appeared pure by TLC on silica gel in hexane:ethyl acetate:methanol (10:15:0.1), $R_f$=0.3 and by HPLC (Water's-$C_{18}$ μ-Bondapak, 35% acetonitrile:water, flow=2.5 ml/min, $t_R$=8.6 min, UV detection λ=265 nm). MS (ci MH+ =321), NMR-DMSOd6 and IR-KBr are consistent with the structure, mp=190°-193° C.

ANALYSIS: Calculated for $C_{16}H_{20}N_2O_5$: 59.98%C, 6.31%H, 8,74%N. Found: 59.17%C, 6.30%H, 8.63%N.

EXAMPLE 81

2-Methyl-7-nitrospiro[2H-1,4-benzodioxepin-3(5H)4'-piperidine]hydrochloride

The compound 1'-acetyl-2-methyl-7-nitrospiro[2H-1,4-benzodioxepin-3(5H)4'-piperidine] (2.2 g, 6.9 mmole) was suspended in 28 ml of 6N hydrochloric acid under nitrogen. The mixture was stirred and heated at reflux overnight. The resultant solution was cooled to 5° C. upon which colorless crystals formed. The product was filtered and washed with cold methanol. The crystals which were dried at 100° C. weighed 2.0 g (6.4 g mmole, 92.8%) and appeared pure by HPLC (Water's-$C_{18}$ μ-Bondapak, 35% acetonitrile/0.05M ammonium citrate, flow=1.5 ml/min, $t_R$=3.4 min, UV detection λ=265 nm) and by TLC on silica gel in ethanol:ammonium hydroxide (7:3), $R_f$=0.7. MS (ci MH+ =279), NMR-DMSOd6 and IR-KBr are consistent with the structure, mp=296°-301° C. (d).

ANALYSIS: Calculated for $C_{14}H_{19}ClN_2O_4$: 53.42%C, 6.10%H, 8.90%N. Found: 53.17%C, 6.08%H, 9.05%N.

EXAMPLE 82

7-Chloro-2-methyl-1'-bis(4-fluorophenyl)methylspiro[2H-1,4-benzodioxepin-3(5H)4'-piperidine]hydrochloride The compound 7-chloro-2-methylspiro[2H-1,4-benzodioxepin-3(5H)4'-piperidine]hydrochloride (4.3 g, 14.1 mmole) was dissolved in 100 ml of n-butylacetate and stirred under nitrogen at reflux with 4.5 g of potassium carbonate (milled, anhydrous), 15 mg of potassium iodide and 3.7 g of bis(4-fluorophenyl)methyl chloride (15.6 mmole). After being allowed to react for 48 hr. the reaction was determined to be complete by TLC. The mixture was cooled to ambient temperature, filtered, and taken to dryness on the rotary evaporator. The oily residue was loaded onto a 100 g alumina column packed in ether. Fractions of 50 ml were collected and the desired material was found in numbers 2–4. These were combined, taken to dryness and dissolved in anhydrous ether. The hydrochloride salt was precipitated and recrystallized from toluene:ethyl acetate:ethanol yielding 2.0 g (4.0 mmole, 27.8%) of 7-chloro-2-methyl-1'-bis(4-fluorophenyl)methylspiro[2H-1,4-benzodioxepin-3(5H)4'-piperidine]hydrochloride which appeared pure by TLC on silica gel in hexane:ethyl acetate:methanol:ammonium hydroxide (10:10:1:0.1), $R_f=0.4$ and by HPLC (Water's $C_{18}$ $\mu$-Bondapak, 65% acetonitrile/35% 0.05M ammonium citrate, flow=2.0 ml/min $t_R=11.6$ min, UV detection $\lambda=265$ nm). MS (MH+ =470) NMR-DMSOd$_6$ and IR-KBr are consistent with the structure, mp=251°–255° C.

ANALYSIS: Calculated for $C_{27}H_{27}Cl_2F_2NO_2$: 64.03%C, 5.38%H, 2.76%N. Found: 63.92%C, 5.42%H, 2.65%N.

EXAMPLE 83

1'-[4,4-Bis(4-fluorophenyl)butyl]-2-methyl-7-nitrospiro[2H-1,4-benzodioxepin-3(5H)4'-piperidine]hydrochloride The compound 2-methyl-7-nitrospiro[2H-1,4-benzodioxepin-3(5H)4'-piperidine]hydrochloride (5 g, 15.9 mmole) was dissolved in 100 ml of n-butylacetate and stirred under nitrogen at reflux with 5 g of milled anhydrous potassium carbonate, 15 mg of potassium iodide, and 4.7 g of 4,4-bis(4-fluorophenyl)butyl chloride (16.7 mmole). After being allowed to react for 48 hr. the reaction was determined to be complete by TLC. The mixture was cooled to ambient temperature, filtered and reduced in volume on a rotary evaporator. The oily residue was loaded onto a 150 g alumina column packed in ether. Fractions of 50 ml were collected and the desired material was found in numbers 3–5. These were combined and taken to dryness under vacuum. The residue was dissolved in anhydrous ether and the hydrochloride was precipitated. Recrystallization from ethyl acetate/ethanol afforded 5.1 g of 1'-[4,4-bis(4-fluorophenyl)butyl]-2-methyl-7-nitrospiro[2H-1,4-benzodioxepin-3(5H)4'-piperidine]hydrochloride. The material appeared pure by TLC on silica gel in hexane:ethyl acetate:methanol:ammonium hydroxide (10:10:1:0.1) $R_f=0.4$ and by HPLC (Water's-$C_{18}$ $\mu$-Bondapak, 65% acetonitrile: 35% 0.05M ammonium citrate, flow=3.0 ml/min, $t_R=2.3$ min., UV detection $\lambda=265$ nm). MS (MH+ =523) NMR-DMSOd$_6$ and IR-KBr are consistent with the structure, mp=247°–251° C.

ANALYSIS: Calculated for $C_{30}H_{33}ClF_2N_2O_4$: 64.45%C, 5.96%H, 5.01%N. Found: 64.40%C, 6.18%H, 4.89%N.

EXAMPLE 84

2-Methyl-1'-[5,5-bis(4-fluorophenyl)pentyl]spiro[2H-1,4-benzodioxepin-3(5H)4'-piperidine]hydrochloride The compound 2-methylspiro[2H-1,4-benzodioxepin-3(5H)4'-piperidine]hydrochloride (6 g, 22.3 mmole) was dissolved in 100 ml of n-butylacetate and stirred under nitrogen at reflux with 6 g of milled anhydrous potassium carbonate, 15 mg of potassium iodide and 6.9 g of 5,5-bis(4-fluorophenyl)pentyl chloride (23.4 mmole). After being allowed to react for 48 hr. the reaction was determined to be complete by TLC. The mixture was cooled to ambient temperature, filtered and taken to dryness on a rotary evaorator. The oily residue was loaded onto a 150 g alumina column packed in ether. Fractions of 50 ml were collected and the desired material was found in numbers 3–5. These were combined and taken to dryness under vacuum. The residue was dissolved in anhydrous ether and the hydrochloride precipitated. Recrystallization from toluene:ethyl acetate afforded 6.2 g of 2-methyl-1'-[5,5-bis(4-fluorophenyl)pentyl]-spiro[2H-1,4-benzodioxepin-3(5H)4'-piperidine]hydrochloride. The product appeared to be pure by TLC on silica gel in hexane:ethyl acetate:methanol:ammonium hydroxide (10:10:1:0.1), $R_f=0.6$ and by HPLC (Water's-$C_{18}$ $\mu$-Bondapak, 65% acetonitrile/35% 0.05M ammonium citrate, flow=3.0 ml/min, $t_R=2.13$ min, UV detection $\lambda=265$ nm). MS (MH+ =492), NMR-DMSOd$_6$ and IR-KBr are consistent with the structure, mp=176°–179° C.

ANALYSIS: Calculated for $C_{31}H_{36}Cl_2F_2NO_2$: 70.50%C, 6.88%H, 2.65%N. Found: 70.35%C, 7.15%H, 2.58%N.

EXAMPLE 85

7-Chloro-1'-[2-(bis(4-fluorophenyl)methoxy)ethyl]-2-methylspiro[2H-1,4-benzodioxepin-3(5H)4'-piperidine]hydrochloride The compound 7-chloro-2-methylspiro[2H-1,4-benzodioxepin-3(5H)4'-piperidine]hydrochloride (5 g, 16.5 mmole) was suspended in 100 ml of n-butylacetate along with 5 g of potassium carbonate (milled, anhydrous), 15 mg of potassium iodide and 4.9 g of 2-[bis(4-fluorophenyl)methoxyethyl]chloride (17.3 mmole). The mixture was heated at reflux for 48 hr. after which TLC indicated complete conversion to product. The mixture was filtered and taken to dryness on a rotary evaporator. The residual oil was loaded onto a 100 g alumina column packed in ether. Fractions of 50 ml were collected and the desired material was found in numbers 3–5. These were combined and concentrated under vacuum. The oily residue was dissolved in anhydrous ether from which the hydrochloride was precipitated. The solids were recrystallized from ethyl acetate resulting in 5.2 g of 7-chloro-1'-[2-(bis(4-fluorophenyl)methoxy)ethyl]-2-methylspiro[2H-1,4-benzodioxepin-3(5H)4'-piperidine]hydrochloride (9.4 mmole, 57.6%) which appeared pure by TLC on silica gel in hexane:ethyl acetate:methanol:ammonium hydroxide (10:10:1:0.1), $R_f=0.6$ and by HPLC (Water's-$C_{18}$ $\mu$-Bondapak 65% acetonitrile:35% 0.05M ammonium citrate, flow=3.0 ml/min, $t_R=2.4$ min, UV detection $\lambda=265$ mn). MS (MH+ =514), NMR (DMSOd$_6$) and IR (KBr) are consistent with the structure, mp=178°–180° C.

ANALYSIS: Calculated for $C_{29}H_{31}Cl_2F_2NO_3$: 63.27%C, 5.69%H, 2.54%N. Found: 63.28%C, 5.68%H, 2.37%N.

EXAMPLE 86

7-Chloro-2-methyl-1'-[5,5-bis(4-fluorophenyl)pentyl]-spiro[2H-1,4-benzodioxepin-3(5H)4'-piperidine]hydrochloride The compound 7-chloro-2-methylspiro[2H-1,4-benzodioxepin-3(5H)4'-piperidine hydrochloride (6.0 g, 19.7 mmole) was suspended in 100 ml of n-butylacetate along with 6.0 g of milled, anhydrous potassium carbonate, 15 mg of KI and 6.1 g of 5,5-bis(4-fluorophenyl)-pentylchloride (20.7 mmole). The mixture was stirred at reflux temperature under nitrogen for 48 hr. The reaction was determined to be complete by HPLC. The mixture was cooled to ambient temperature, filtered and taken to dryness on a rotary evaporator. The residual oil was loaded onto a 150 g alumina column packed in ether and fractions of 50 ml were collected. The desired product was found in numbers 3–5. These were combined and taken to dryness under vacuum. The oily residue was dissolved in ether and the hydrochloride precipitated. The material was recrystallized from ethyl acetate until material with reproducible melting point was obtained. 7-Chloro-2-methyl-1'-[5,5-bis(4-fluorophenyl)pentyl]spiro[2H-1,4-benzodioxepin-3(5H)4'-piperidine]hydrochloride (2.0 g, 3.6 mmole, 18.1%) was isolated which appeared pure by TLC on silica gel in hexane:ethyl acetate:methanol:ammonium hydroxide (10:10:1:0.1), $R_f$=0.5 and by HPLC (Water's-$C_{18}$ μ-Bondapak, 65% acetonitrile:35% 0.05M ammonium citrate, flow=3.0 ml/min, $t_R$=2.7 min., UV detection λ=265 nm) MS (MH+ =526), NMR (DMSOd6) and IR (KBr) are consistent with the structure, mp=132°–137° C.

ANALYSIS: Calculated for $C_{31}H_{35}Cl_2F_2NO_2$: 66.18%C, 6.28%H, 2.49%N. Found: 65.43%C, 6.39%H, 2.38%N.

EXAMPLE 87

1'-(4,4-Dicyclohexylbutyl)-7-chloro-2-methylspiro[2H-1,4-benzodioxepin-3(5H)4'-piperidine]hydrochloride The compound 7-chloro-2-methylspiro[2H-1,4-benzodioxepin-3(5H)4'-piperidine]hydrochloride (5 g, 16.4 mmole) was suspended in 100 ml of n-butylacetate and stirred with 6 g of potassium carbonate, 15 mg of potassium iodide and 4.7 g of 4,4-dicyclohexylbutylchloride (16.4 mmole). The mixture was heated at reflux under nitrogen for 48 hr. The reaction was determined to be complete by TLC. After filtration the solvent was removed under vacuum. The oily residue was loaded onto a 100 g alumina column and eluted in 50 ml fractions. The material was found in numbers 3–5 which were combined and reduced in volume under vacuum. The residual oil was dissolved in anhydrous ether from which the hydrochloride salt was precipitated. The solids were filtered, washed with ether and vacuum dried. The reaction yielded 3.5 g of 1'-(4,4-dicyclohexylbutyl)-7-chloro-2-methylspiro[2H-1,4-benzodioxepin-3(5H)4'-piperidine]hydrochloride (6.7 mmole, 40.7% ) which appeared pure by TLC on silica gel in hexane:ethyl acetate:methanol:ammonium hydroxide (10:10:1:0.1), $R_f$=0.8 and in dichloromethane:methanol (9:1), $R_f$=0.6. MS (MH+ =489), NMR (CDCl3) and IR (CHCl3) are consistent with the structure, mp=246°–250° C.(d).

ANALYSIS: Calculated for $C_{30}H_{47}Cl_2NO_2.HCl$: 68.67%C, 9.05%H, 2.67%N. Found: 69.13%C, 8.87%H, 2.52%N.

EXAMPLE 88

2-Methyl-1'-(2-hydroxy-3-phenoxypropyl)spiro[2H-1,4-benzodioxepin-3(5H)4'-piperidine]hydrochloride The compound 2-methylspiro[2H-1,4-benzodioxepin-3(5H)4'-piperidine]hydrochloride (5.0 g, 18.6 mmole) was converted to its free base and dried. The oil was dissolved in 50 ml of toluene and stirred at reflux temperature with 2.9 g of 1,2-epoxy-3-phenoxypropane (19.5 mmole) for 7 hr. TLC indicated the reaction was complete. After cooling to ambient temperature the solvent was removed under vacuum. The residual oil was loaded onto a 100 g alumina column packed in ether. Fractions of 50 ml were collected and the desired material was found in numbers 3–9. These were combined and the hydrochloride salt was precipitated. Recrystallization from ethyl acetate-ethanol afforded 3.2 g of 2-methyl-1'-(2-hydroxy-3-phenoxypropyl)spiro[2H-1,4-benzodioxepin-3(5H)4'-piperidine]hydrochloride (7.6 mmole, 41.0%) which appeared pure by TLC on silica gel in hexane:ethyl acetate:methanol:ammonium hydroxide (10:10:1:0.1), $R_f$=0.5 and dichloromethane:methanol (9:1), $R_f$=0.4. MS (MH+ =384), NMR (CDCl3) and IR (CHCl3) are consistent with the structure, mp=242°–245° C.

ANALYSIS: Calculated for $C_{23}H_{30}ClNO_4$: 65.77%C, 7.21%H, 3.33%N. Found: 65.49%C, 7.26%H, 3.17%N.

EXAMPLE 89

2-Methyl-1'-[2-hydroxy-3-(4-methoxyphenoxy)propyl]-spiro[2H-1,4-benzodioxepin-3(5H)4'-piperidine]hydrochloride 2-Methylspiro[2H-1,4-benzodioxepin-3(5H)4'-piperidine]hydrochloride (6.0 g, 22.3 mmole) was converted to its free base and dried. The residual material was dissolved in 50 ml of toluene and stirred with 4.2 g of 1-(4-methoxyphenoxy)-2,3-epoxypropane (23.4 mmole) at reflux temperature overnight. TLC indicated complete reaction. The mixture was cooled and the solvent removed under vacuum. The oily residue was loaded onto a 100 g alumina column packed in dichloromethane. Fractions of 50 ml were collected and the desired material was found in numbers 2–8. These were combined and acidified with ethereal hydrogen chloride. The salt was precipitated from the mixture upon the addition of ether. The precipitate was filtered and recrystallized from ethyl acetate-ethanol yielding 4.0 g of 2-methyl-1'-[2-hydroxy-3-(4-methoxyphenoxy)-propyl]-spiro[2H-1,4-benzodioxepin-3(5H)4'-piperidine]hydrochloride (8.9 mmole, 39.9%) which appeared pure by TLC on silica gel in hexane:ethyl acetate:methanol:ammonium hydroxide (10:10:1:0.1), $R_f$=0.5 and in dichloromethane:methanol (9:1), $R_f$=0.4. MS (MH+ =414), NMR-DMSOd6 and IR-CHCl3 are consistent with the structure, mp=200°–205° C.

ANALYSIS: Calculated for $C_{24}H_{32}ClNO_5$: 64.05%C, 7.18%H, 3.11%N. Found: 63.87%C, 7.08%H, 3.06%N.

EXAMPLE 90

2-Methyl-1'-[2-hydroxy-3-(4-fluorophenoxy)propyl]-spiro[2H-1,4-benzodioxepin-3(5H)4'-piperidine]hydrochloride The compound 2-methylspiro[2H-1,4-benzodioxepin-3(5H)4'-piperidine]hydrochloride (6.0 g, 22.3 mmole) was converted to its free base and dried. The resultant oil was dissolved in 50 ml of toluene along with 4.1 g of 1,2-epoxy-3-(4-fluorophenoxy)propane (24.5 mmole). The mixture was heated at reflux for 18 hr, after which TLC indicated that the reaction was complete. The solvent was removed under vacuum and the oily residue was loaded onto a 100 g alumina column packed in ether. Fractions of 50 ml were collected. The desired product was found in numbers 3–6, which were then combined. The hydrochloride was precipitated and recrystallized from ethyl acetate-ethanol yielding 4.0 g of 2-methyl-1'-[2-hydroxy-3-(4-fluorophenoxy)propyl]-spiro[2H-1,4-benzodioxepin-3(5H)4'-piperidine]hydrochloride (9.1 mmole, 41.0%) which appeared pure by TLC on silica gel in hexane:ethyl acetate:methanol:ammonium hydroxide (10:10:1:0.1), $R_f=0.5$ and in dichloromethane:methanol (9:1), $R_f=0.4$. MS (MH$^+$=402), NMR (CDCl$_3$) and IR (CHCl$_3$) are consistent with the structure, mp=240°–245° C.(d).

ANALYSIS: Calculated for $C_{23}H_{28}FNO_4.HCl$: 63.07%C, 6.69%H, 3.20%N. Found: 62.83%C, 6.61%H, 3.13%N.

EXAMPLE 91

7-Chloro-2-methyl-1'-(2-hydroxy-3-phenoxypropyl)-spiro[2H-1,4-benzodioxepin-3(5H)4'-piperidine]hydrochloride The compound 7-chloro-2-methylspiro[2H-1,4-benzodioxepin-3(5H)4'-piperidine]hydrochloride (6.0 g, 19.7 mmole) was converted to its free base and dried. The oily residue was dissolved in 50 ml of toluene along with 3.0 g of 1,2-epoxy-3-phenoxypropane (19.7 mmole). The mixture was heated at reflux for 18 hr. after which TLC indicated complete reaction. The solvent was removed under vacuum. The residual oil was loaded onto a 150 g alumina column packed in ether. Fractions of 50 ml were collected and the desired material was found in numbers 4–9 which were then combined. The hydrochloride salt was precipitated and recrystallized from ethyl acetate-ethanol affording 3.2 g of 7-chloro-2-methyl-1'-(2-hydroxy-3-phenoxypropyl)-spiro[2H-1,4-benzodioxepin-3(5H)4'-piperidine]hydrochloride (7.0 mmole, 35.8%) which appeared to be pure by TLC on silica gel in hexane:ethyl acetate:methanol:ammonium hydroxide (10:10:1:0.1), $R_f=0.5$ and in dichloromethane:methanol (9:1), $R_f=0.4$. MS (MH$^+$=418) NMR (DMSOd$_6$) and IR (CHCl$_3$) are consistent with the structure, mp=260°–262° C.(d).

ANALYSIS: Calculated for $C_{23}H_{28}ClNO_4.HCl$: 60.79%C, 6.45%H, 3.08%N. Found: 60.78%C, 6.60%H, 3.04%N.

EXAMPLE 92

7-Chloro-2-methyl-1'-[2-hydroxy-3-(4-methoxyphenoxy)propyl]spiro[2H-1,4-benzodioxepin-3(5H)4'-piperidine]hydrochloride The compound 7-chloro-2-methylspiro[2H-1,4-benzodioxepin-3(5H)4'-piperidine]-hydrochloride (6.0 g, 19.7 mmole) was converted to its free base and dried. The residual material was dissolved in 50 ml of toluene along with 3.6 g of 1,2-epoxy-3-(4-methoxyphenoxy)propane (19.7 mmole). The mixture was heated at reflux temperature for 18 hr. after which TLC indicated complete reaction. The solvent was removed under vacuum. The residual oil was loaded onto a 150 g alumina column packed in dichloromethane. Fractions of 75 ml were collected. The desired material was found in numbers 2–9 which were then combined. The hydrochloride salt was precipitated and recrystallized from ethyl acetate-ethanol affording 3.5 g of 7-chloro-2-methyl-1'-[2-hydroxy-3-(4-methoxyphenoxy)propyl]spiro[2H-1,4-benzodioxepin-3(5H)4'-piperidine]hydrochloride (7.2 mmole, 36.5%) which appeared pure by TLC on silica gel in hexane:ethyl acetate:methanol:ammonium hydroxide (10:10:1:0.1), $R_f=0.5$ and in dichloromethane:methanol (9:1), $R_f=0.4$. MS (MH$^+$=448), NMR (DMSOd$_6$) and IR (CHCl$_3$) are consistent with the structure, mp=235°–240° C.(d).

ANALYSIS: Calculated for $C_{24}H_{30}ClNO_5.HCl$: 59.50%C, 6.46%H, 2.89%N. Found: 59.49%C, 6.52%H, 2.78%N.

EXAMPLE 93

7-Chloro-2-methyl-1'-[2-hydroxy-3-(4-fluorophenoxy)propyl]spiro[2H-1,4-benzodioxepin-3(5H)4'-piperidine]hydrochloride The compound 7-chloro-2-methylspiro[2H-1,4-benzodioxepin-3(5H)4'-piperidine]hydrochloride (6.0 g, 19.7 mmole) was converted to its free base and dried. The residual material was dissolved in 50 ml of toluene along with 3.7 g of 1,2-epoxy-3-(4-fluorophenoxy)propane (19.7 mmole). The mixture was heated at reflux temperature for 18 hr. after which TLC indicated complete reaction. The solvent was removed under vacuum. The residue was loaded onto a 150 g alumina column packed in dichloromethane. Fractions of 75 ml were collected. The desired product was found in numbers 2–8 which were then combined. The solvent was removed and the oily residue dissolved in ether. The hydrochloride salt was precipitated and recrystallized from ethyl acetate-ethanol affording 3.9 g of 7-chloro-2-methyl-1'-[2-hydroxy-3-(4-fluorophenoxy)propyl]-spiro[2H-1,4-benzodioxepin-3(5H)4'-piperidine]hydrochloride (8.3 mmole, 42.1%) which appeared pure by TLC on silica gel in hexane:ethyl acetate:methanol:ammonium hydroxide (10:10:1:0.1), $R_f=0.5$ and in dichloromethane:methanol (9:1), $R_f=0.4$. MS (MH$^+$=436), NMR (DMSOd$_6$) and IR (CHCl$_3$) are consistent with the structure, mp=245°–249° C.(d).

ANALYSIS: Calculated for $C_{23}H_{28}ClNO_4.HCl$: 58.47%C, 5.99%H, 2.96%N. Found: 58.58%C, 6.12%H, 2.88%N.

EXAMPLE 94

7-Chloro-1'-[2-(diphenylmethoxy)ethyl]-2-methylspiro-[2H-1,4-benzodioxepin-3(5H)4'-piperidine]hydrochloride hemihydrate The compound 7-chloro-2-methylspiro[2H-1,4-benzodioxepin-3(5H)4'-piperidine]hydrochloride (6.0 g, 19.7 mmole) was suspended in 100 ml of n-butylacetate along with 6 g of potassium carbonate (milled, anhydrous) and 4.9 g of 2-(diphenylmethoxy)ethyl chloride (20.0 mmole). The mixture was heated at reflux for 24 hr. The reaction was complete by TLC. The mixture was filtered and the solvent was evaporated under vacuum. The oily residue was loaded onto a 150 g alumina column packed in ether. Fractions of 75 ml were collected and the desired material was found in numbers 3-4. The fractions were combined and the solvent was removed under vacuum. The residue was dissolved in ether and treated with ethereal hydrogen chloride. The resultant oil crystallized when triturated with ethylacetate. Several crystallizations from ethyl acetate-ethanol afforded 2.0 g of 7-chloro-1'-[2-(diphenylmethoxy)ethyl]-2-methylspiro[2H-1,4-benzodioxepin-3(5H)4'-piperidine]hydrochloride hemihydrate (3.8 mmole, 19.4%), which appeared pure by TLC on silica gel in hexane:ethyl acetate:methanol:ammonium hydroxide (10:10:1:0.1), $R_f$=0.6 and by HPLC (Water's-$C_{18}$ μ-Bondapak, 65% acetonitrile 35% 0.05M ammonium citrate, flow=3.0 ml/min, $t_R$=2.4 min, UV detection λ=265 nm). MS (MH+ =478), NMR ($CDCl_3$) and IR ($CHCl_3$) are consistent with the structure, mp=109°-116° C.

ANALYSIS: Calculated for $C_{29}H_{33}Cl_2NO_{3.5}$: 66.53%C, 6.56%H, 2.67N. Found: 66.61%C, 6.49%H, 2.62N.

EXAMPLE 95

2-Methyl-1'-[2-hydroxy-3-(1-naphthoxy)propyl]-spiro[2H-1,4-benzodioxepin-3(5H)4'-piperidine]hydrochloride hemihydrate The compound 2-methylspiro[2H-1,4-benzodioxepin-3(5H)4'-piperidine]hydrochloride (6.0 g, 22.3 mmole) was converted to its free base and dried. The residue was dissolved in 50 ml of toluene along with 4.7 g of 1,2-epoxy-3-(1-naphthoxy)propane (22.3 mmole). The mixture was heated at reflux under nitrogen overnight. TLC indicated the reaction to be complete. The toluene was removed under vacuum and the residue dissolved in a minimum of dichloromethane. The mixture was loaded onto a 150 g alumina column packed in dichloromethane. Fractions of 75 ml were collected and the desired material was found in numbers 5-10. These were combined, taken to dryness and dissolved in ether. The hydrochloride salt was precipitated and recrystallized from ethyl acetate-ethanol yielding 2.0 g of 2-methyl-1'-[2-hydroxy-3-(1-naphthoxy)propyl]spiro[2H-1,4-benzodioxepin-3(5H)4'-piperidine]hydrochloride hemihydrate (4.3 mmole, 19.1%). The product appeared pure by TLC on silica gel in hexane:ethylacetate:methanol:ammonium hydroxide (10:10:1:0.1), $R_f$=0.5 and by HPLC (Water's-$C_{18}$ μ-Bondapak, 50% acetonitrile 50% 0.05M ammonium citrate, flow=3.0 ml/min, $t_R$=2.5 min. UV detection λ=265 nm). MS (MH+ =434), NMR ($DMSOd_6$) and IR (KBr) are consistent with the structure, mp=192°-197° C.

ANALYSIS: Calculated for $C_{27}H_{33}ClNO_{4.5}$: 67.69%C, 6.96%H, 2.92%N. Found: 67.75%C, 6.94%H, 2.83%N.

EXAMPLE 96

7-Chloro-2-methyl-1'-[2-hydroxy-3-(1-naphthoxy)-propyl]spiro[2H-1,4-benzodioxepin-3(5H)4'-piperidine]hydrochloride hemihydrate The compound 7-chloro-2-methylspiro[2H-1,4-benzodioxepin-3(5H)4'-piperidine]hydrochloride (6.0 g, 19.7 mmole) was converted to its free base and dried. The free base was dissolved in 50 ml of toluene along with 4.2 g of 1,2-epoxy-3-(1-naphthoxy)propane (19.7 mmole). The mixture was heated at reflux overnight under nitrogen. TLC indicated that the reaction was complete. The solvent was removed under vacuum. The residue was loaded onto a 150 g alumina column packed in dichloromethane. Fractions of 75 ml were collected and the desired material was found in numbers 5-12. These were combined and taken to dryness under vacuum. The residue was dissolved in ether and the hydrochloride salt precipitated. Recrystallization from ethyl acetate-ethanol afforded 1.2 g of 7-chloro-2-methyl-1'-[2-hydroxy-3-(1-naphthoxy)propyl]spiro[2H-1,4-benzodioxepin-3(5H)4'-piperidine]hydrochloride hemihydrate (2.4 mmole, 12.2%), which appeared pure by TLC in hexane:ethylacetate:methanol:ammonium hydroxide (10:10:1.0.1), $R_f$=0.5 and by HPLC (Water's-$C_{18}$ μ-Bondapak, 50% acetonitrile 50% 0.05M ammonium citrate, flow=3.0 ml/min, $t_R$=3.6 min, UV detection λ=265 nm). NMR ($DMSOd_6$) and IR ($CHCl_3$) are consistent with the structure, mp=190°-195° C.(d).

ANALYSIS: Calculated for $C_{27}H_{32}Cl_2NO_{4.5}$: 63.15%C, 6.29%H, 2.73%N. Found: 63.16%C, 6.31%H, 2.64%N.

EXAMPLE 97

4-Hydroxy-1-methyl-4-(1,3-dithian-2-yl)piperidine

The compound 1,3-dithiane (12.0 g, 0.1 mole, sublimed) was dissolved in 500 ml of dry THF and was cooled to −30° C. n-Butyl lithium (43.5 ml of a 2.3M solution in hexane, 0.1 mole) was added to the cooled solution at such a rate as to maintain the temperature below −20° C. Metallation was carried out at −20° C. for 3 hr. N-Methyl-4-piperidone (12.3 ml, 11.3 g, 0.1 mole) was added at −30° C. and maintained at −20° C. for 2 hr. The reaction flask was packed in dry ice (−60° C.) and was allowed to warm gradually to 20° C., overnight.

The mixture was quenched with 60 ml of saturated aqueous ammonium chloride. An aqueous phase separated out which was collected, diluted with saturated brine and extracted several times with chloroform. All organic phases were combined, dried over potassium carbonate, filtered and taken to dryness under vacuum. The residue was dissolved in ether from which white crystals precipitated. The solids were filtered, washed several times with ether and dried under vacuum at 50° C.

The reaction yielded 15.5 g of 4-hydroxy-1-methyl-4-(1,3-dithian-2-yl)piperidine (66.5 mmole, 66.5%) which appeared pure by TLC on silica gel in dichloromethane:methanol (9:1), $R_f$=0.3 and in hexane:ethyl acetate:methanol:ammonium hydroxide (10:10:1:0.1), $R_f$=0.3. MS (ci M+ =233), NMR ($CDCl_3$) and IR ($CHCl_3$) are consistent with the structure, mp=115°-120° C.

ANALYSIS: Calculated for $C_{10}H_{19}NOS_2$: 51.45%C, 8.22%H, 6.00%N. Found: 51.77%C, 8.13%H, 5.98%N.

EXAMPLE 98

4-(2-Fluorophenylmethoxy)-1-methyl-4-(1,3-dithian-2-yl)piperidine hydrochloride

The compound 4-hydroxy-1-methyl-4-(1,3-dithian-2-yl)piperidine (197.9 g, 0.85 mmole) was dissolved in 1600 ml of dry DMF and was cooled to 5° C. under nitrogen. Potassium t-butoxide (100 g, 0.89 mole) dissolved in 400 ml of dry DMF was added to the above solution at such a rate as to maintain the temperature below 10° C. During the course of the potassium alkoxide formation a precipitate formed. The mixture was cooled to −25° C. 2-Fluorobenzylchloride (101.0 ml, 122.8 g, 0.85 mole) was added dropwise maintaining the reaction temperature below −20° C. After complete addition of the benzylchloride the mixture was allowed to warm to 5° C. The mixture was allowed to react for 4 hr. after which it was determined to be complete by TLC. The reaction was quenched with an equal volume of ice/water and extracted with ether. The ether extracts were combined, dried over potassium carbonate and filtered. The solvent was removed under vacuum. The residue was dissolved in ethanol:ether (1:3). The hydrochloride was formed by passing hydrogen chloride through the mixture. The salt crystallized overnight yielding 75.4 g of product (199.7 mmole, 23.5%), mp=110°–115° C. A 5.0 g sample of this material gave, after recrystallization from ethyl acetate/ethanol, 2.3 g of a compound, mp=207°–211° C.(d). The solvent was removed from the mother liquors. The residue could be recrystallized from ethyl acetate:ethanol yielding in two crops 39.3 g of 4-(2-fluorophenylmethoxy)-1-methyl-4-(1,3-dithian-2-yl)piperidine hydrochloride (104.1 mmole, 12.3%) which appeared pure by TLC on silica gel in dichloromethane:methanol:ammonium hydroxide (10:10:2:0.1), $R_f$=0.4, mp=207°–211° C.(d). Both the high and low melting materials gave spectra [MS (MH+=342), NMR (DMSOd$_6$), IR (CHCl$_3$)] which are consistent with the structure.

ANALYSIS: Calculated for $C_{17}H_{25}FClNOS_2 \cdot HCl$: 54.01%C, 6.68%H, 3.70%N. Found: 53.98%C, 6.67%H, 3.58%N.

EXAMPLE 99

4-(2-Fluorophenylmethoxy)-1-methyl-4-oxomethyl piperidine

The compound 4-(2-fluorophenylmethoxy)-1-methyl-4-(1,3-dithian-2-yl)piperidine hydrochloride (5 g, 13.1 mmole) was suspended in tetrahydrofuran (50 ml), and water (5 ml) was added to completely dissolve the compound. Red mercuric oxide (8.6 g, 39.7 mmole) was added to the solution. After a complex was formed, BF$_3$ etherate (32.3 ml, 39.7 mmole) was added dropwise to the stirred suspension under nitrogen and reaction was taken to completion as indicated by TLC. The reaction mixture was diluted with an equal volume of ether and filtered. The filtrate was treated with saturated potassium carbonate to form a precipitate. The mixture was extracted with ethyl acetate, and the ethyl acetate extracts were washed with saturated brine. The washed extract was dried over anhydrous potassium carbonate, filtered and taken to dryness. The residue was dissolved in ether from which the hydrochloride was precipitated. The resulting material was recrystallized from ethyl acetate/ethanol. After filtration, washing with ethyl acetate and ether, the product was air-dried to yield 1.3 g (4.5 mmole, 36.9%) of 4-(2-fluorophenylmethoxy)-1-methyl-4-oxomethyl piperidine hydrochloride. MS (MH+=252), NMR (CDCl$_3$) and IR (CHCl$_3$) were consistent with the structure, mp=164°–167° C.

ANALYSIS: Calculated for $C_{14}H_{19}FClNO_2$: 58.43%C, 6.67%H, 4.86%N. Found: 57.64%C, 6.70%H, 4.73%N.

EXAMPLE 100

4-(2-Fluorophenylmethoxy)-4-hydroxymethyl-1-methylpiperidine

The compound 4-(2-fluorophenylmethoxy)-1-methyl-4-oxomethylpiperidine (37.7 g, 150 mmole) was suspended in 400 ml of water. Ethanol (210 ml) was added to dissolve the oil. The mixture was stirred under nitrogen with 5.7 g of sodium borohydride (0.15 mole), overnight. The residual sodium borohydride was decomposed with 25 ml of 10% hydrochloric acid. After stirring for 15 minutes the mixture was filtered, combined with saturated potassium carbonate and extracted with ether. The ether extracts were combined, dried over potassium carbonate and filtered. The volatiles were removed under vacuum. The residue was recrystallized from cyclohexane yielding 31.6 g of 4-(2-fluorophenylmethoxy)-4-hydroxymethyl-1-methylpiperidine (0.13 mole, 86.7%) which appeared pure by TLC on silica gel in dichloromethane:methanol (9:1), $R_f$=0.2 and in hexane:ethyl acetate:methanol:ammonium hydroxide (10:10:2:0.1), $R_f$=0.1 MS (MH+254), NMR (CDCl$_3$) and IR (CHCl$_3$) are consistent with the structure, mp=104°–108° C.

ANALYSIS: Calculated for $C_{14}H_{20}FNO_2$: 66.37%C, 7.97%H, 5.53%N. Found: 66.37%C, 7.88%H, 5.58%N.

EXAMPLE 101

1′-Methylspiro[2H-1,4-benzodioxepin-3(5H)4′-piperidine]hydrochloride

The compound 4-(2-fluorophenyl)methoxy-4-hydroxymethyl-1-methyl piperidine (30.8 g, 0.422 mole) was dissolved in 500 ml of anhydrous tetrahydrofuran under nitrogen. Potassium t-butoxide (15 g) was added to the stirred solution and heated at reflux until the reaction was substantially complete. The reaction mixture was cooled and quenched with saturated potassium carbonate (100 ml), and the aqueous layer was extracted with ether. The organic layer was dried over anhydrous potassium carbonate, filtered and solvent removed. The residue was dissolved in isopropanol/ether solution and the hydrochloride salt was precipitated. The solids were recrystallized from ethyl acetate/ethanol to yield 23.1 g (85.7 mmole, 70.3%) of 1′-methylspiro[2H-1,4-benzodioxepin-3(5H)4′-piperidine]hydrochloride, mp=238°–240° C. MS (MH+=234), NMR (CDCl$_3$) and IR (CHCl$_3$) are consistent with the structure.

ANALYSIS Calculated for: $C_{14}H_{20}ClNO_2$: 62.32%C, 7.49%H, 5.19%N. Found: 61.93%C, 7.43%H, 5.03%N.

EXAMPLE 102

7-Chloro-1′-[2-(2,6-dimethoxyphenoxy)ethyl]-2-methylspiro[2H-1,4-benzodioxepin-3(5H)4′-piperidine]-hydrochloride The compound 7-chloro-2-methylspiro[2H-1,4-benzodioxepin-3(5H)4′-piperidine]hydrochloride (6 g, 19.7 mmole) was suspended in 100 ml of n-butylacetate along with 6 g of potassium carbonate (milled, anhydrous) and 4.7 g of 2-(2,6-dimethoxyphenoxy)ethylchloride (21.7 mmole). The mixture was heated at reflux, under nitrogen, overnight. The reaction was determined to be complete by TLC. The mixture was cooled to room temperature, filtered and taken to dryness under vacuum. The oily residue was purified by flash chromatography on silica gel in hexane:ethylacetate:methanol:ammonium hydroxide (10:10:7.5:0.1). The fraction containing the desired product were combined and taken to dryness. The residue was dissolved in anhydrous ether from which the hydrochloride was precipitated. The salt was filtered and vacuum dried overnight. The material was recrystallized from ethylacetate:ethanol yielding 3.0 g of 7-chloro-1′-[2-(2,6-dimethoxyphenoxy)ethyl]-B 2-methylspiro[2H-1,4- benzodioxepin-3(5H)4'-piperidine]hydrochloride (6.2 mmole, 31.5%) which appeared pure by TLC on silica gel in hexane:ethylacetate:methanol:ammonium hydroxide (10:10:1:0.1), $R_f=0.5$ and dichloromethane:methanol (9:1), $R_f=0.4$. MS (Ci MH=448), NMR (CDCL$_3$) and IR (CHCl$_3$) are consistent with the structure, mp=184°-186° C.

ANALYSIS: Calculated for $C_{24}H_{31}Cl_2NO_5$: 59.50%C, 6.46%H, 2.89%N. Found: 59.48%C, 6.35%H, 2.75%N.

EXAMPLE 103

2-Methyl-1'-[2-hydroxy-3-[bis(4-fluorophenyl)methoxy]propyl]spiro[2H-1,4-benzodioxepin-3(5H)4'-piperidine]hydrochloride The compound 2-methylspiro[2H-1,4-benzodioxepin-3(5H)4'-piperidine]hydrochloride (5 g, 18.6 mmole) was converted to its free base and dried. The residue was dissolved in 60 ml of dry toluene along with 7.0 g of 3-[bis(4-fluorophenyl)methoxy]-1,2-epoxy propane (20.0 mmole, 80% pure), and heated at reflux temperature under nitrogen overnight. TLC indicated that the reaction was complete. The solvent was removed under vacuum. The residue was flash chromatographed on silica gel packed in hexane:ethylacetate:methanol:ammonium hydroxide (900:900:75:5). The fractions containing the purified material were combined and taken to dryness under vacuum. The residue was dissolved in ether from which the hydrochloride was precipitated. The material was recrystallized from ethylacetate:ethanol yielding 2.0 g of 2-methyl-1'-[2-hydroxy-3-[bis(4-fluorophenyl)methoxy]propyl]spiro[2H-1,4-benzodioxepin-3(5H)4'-piperidine]hydrochloride (3.7 mmole, 19.9%). The material appeared pure by TLC on silica gel in hexane:ethylacetate:methanol:ammonium hydroxide (10:10:1:0.1), $R_f=0.5$ and by HPLC (Waters-C$_{18}$ μBondapak, 60% acetonitrile/40% 0.05M ammonium citrate, flow=3.0 ml/min, $t_R$=2.3 min., UV detection ($\lambda$=265 nm), MS (MH+=510), NMR (CDCl$_3$) and IR (CHCl$_3$) are consistent with the structure, mp=206°-210° C.

ANALYSIS: Calculated for $C_{30}H_{34}ClF_2NO_4$: 65.98%C, 6.29%H, 2.56%N. Found: 65.89%C, 6.28%H, 2.47%N.

What is claimed is:
1. A compound of the formula

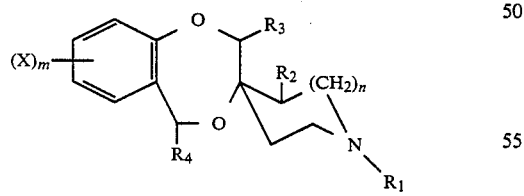

wherein
  m is zero, 1 or 2;
  n is zero or 1;
  (a) a C$_1$ to C$_5$ branched or straight chain alkyl group;
  (b) a terminally substituted C$_1$ to C$_5$ branched or straight chain alkyl group, or a terminally substituted C$_2$ to C$_5$ branched or straight chain alkenyl group, or a terminally substituted C$_4$ alkynyl group, wherein the terminal substituents are one or two substituents independently selected from the group consisting of

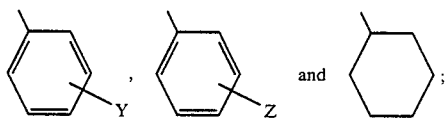

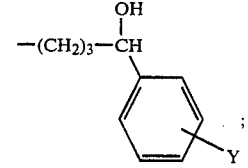   (c)

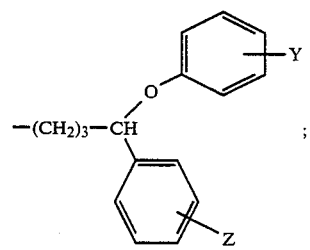   (d)

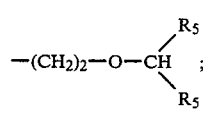   (e)

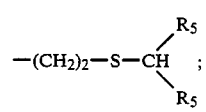   (f)

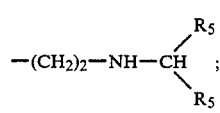   (g)

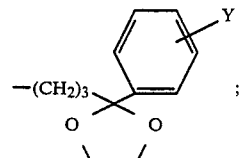   (h)

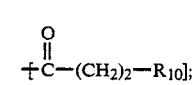   (i)

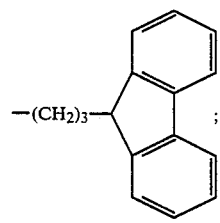   (j)

(k) —(CH₂)₃—[anthracenyl];

(l) a $C_1$ or $C_2$ alkylene group terminally substituted by

[phenyl-Y]

or $C_3$ to $C_5$ cycloalkyl;

(m) a $C_2$ to $C_3$ straight chain alkylene group terminally substituted by one substituent selected from the group consisting of

—OH, —CN, —NR₁₂R₁₃, $\underset{NH_2}{\underset{|}{C}}(=NH)-NH-$ , [benzisoxazole with R₇], [2-methylindole], —N(morpholino)O, —C(CN)(phenyl-Y)(phenyl-Z), —N(benzimidazolone)NH and —C(=O)—[phenyl-Y];

—CN; (n)

$-\overset{NH}{\underset{\|}{C}}-OR_8;$ (o)

$-\overset{O}{\underset{\|}{C}}NR_{12}R_{13};$ (p)

$-\overset{O}{\underset{\|}{C}}-R_8;$ (q)

(r) $-CH_2-\underset{OH}{\underset{|}{CH}}-CH_2-O-$[phenyl-Y];

(s) $-CH_2-\underset{OH}{\underset{|}{CH}}-CH_2-O-$[naphthyl];

(t) $-CH_2-\underset{OH}{\underset{|}{CH}}-CH_2-O-CH($[phenyl-Y])([phenyl-Z]); or (u) $-CH_2-CH_2-O-$[2,6-di-Y-phenyl];

$R_2$ is hydrogen when n=0 or $R_2$ is hydrogen or a $C_1$ to $C_3$ straight chain alkyl group when n=1;

$R_3$ is hydrogen or a $C_1$ to $C_3$ straight chain alkyl group, $R_4$ is hydrogen or a $C_1$ to $C_3$ straight chain alkyl group;

each $R_5$ substituent is independently selected from the group consisting of

[phenyl-Y] and [phenyl-Z];

X is Cl, F, Br, I, —NO₂, —CF₃, —NR₆R₇, $-\overset{O}{\underset{\|}{C}}-NR_6R_7,$ $C_1$ to $C_6$ branched or straight chain alkyl, —CN, —O—R₆, —SR₇, —SO₃R₇, $-\overset{O}{\underset{\|}{C}}-R_8,$ —NHCOR₈, —SO₂R₉ or —SOR₉ where $R_6$ is hydrogen or a $C_1$ to $C_6$ straight chain alkyl group;

$R_7$ is hydrogen or a $C_1$ to $C_6$ straight chain alkyl group;

$R_8$ is a $C_1$ to $C_6$ branched or straight chain alkyl group;

$R_9$ is a $C_1$ to $C_6$ straight chain alkyl group; provided that when m=2, the X-substituents can be the same only when X is selected from the group consisting of Cl, F, Br, I, $C_1$ to $C_6$ branched or straight chain alkyl or —O—$R_6$;

Y and Z are the same or different and are independently selected from the group consisting of H, Cl, F, Br, I, —$NO_2$, —$CF_3$, $C_1$ to $C_4$ straight chain alkyl, alkoxy containing $C_1$ to $C_4$ straight chain alkyl, acyl or —$NH_2$;

$R_{10}$ is

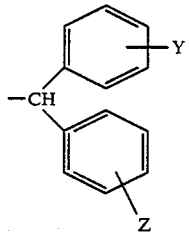

$R_{12}$ and $R_{13}$ are the same or different and are independently selected from the group consisting of hydrogen, methyl and ethyl; and the pharmaceutically acceptable salts and optical and geometric isomers thereof.

2. A compound according to claim 1 in which $R_2$, $R_3$ and $R_4$ are independently selected from hydrogen and a $C_1$ to $C_3$ straight chain alkyl group.

3. A compound according to claim 1 in which m=0.
4. A compound according to claim 1 in which m=1.
5. A compound according to claim 1 in which m=2.
6. A compound according to claim 4 in which X is Cl, F, Br or $NO_2$.
7. A compound according to claim 1 in which $R_2$ and $R_4$ are each hydrogen.
8. A compound according to claim 7 which is 1'-(4,4-diphenylbutyl)-9-chloro-2-methylspiro[2H-1,4-benzodioxepin-3(5H)4'-piperidine].
9. A compound according to claim 7 which is 1'-[4,4-bis(3-fluorophenyl)butyl]-2-methylspiro[2H-1,4-benzodioxepin-3(5H)4'-piperidine].
10. A compound according to claim 7 which is 1'-[4,4-bis(3-fluorophenyl)butyl]-7-fluoro-2-methylspiro[2H-1,4-benzodioxepin-3(5H)4'-piperidine].
11. A compound according to claim 7 which is 1'-[4-(4-fluorophenyl)butyl]-7-fluoro-2-methylspiro[2H-1,4-benzodioxepin-3(5H)4'-piperidine].
12. A compound according to claim 7 which is 1'-[4-(4-fluorophenyl)butyl]-7-chloro-2-methylspiro[2H-1,4-benzodioxepin-3(5H)4'-piperidine].
13. A compound according to claim 7 which is 2-methyl-1'-[3-[2-(4-fluorophenyl)-1,3-dioxolan-2-yl]propyl]spiro-2H-1,4-benzodioxepin-3(5H)4'-piperidine.
14. A compound according to claim 7 which is 2-methyl-1'-[3,3-diphenylpropyl]spiro[2H-1,4-dibenzodioxepin-3(5H)4'-piperidine].
15. A compound according to claim 7 which is 1'-[4,4-bis(4-fluorophenyl)butyl]-7-chloro-2-methylspiro[2H-1,4-benzodioxepin-3(5H)4'-piperidine].
16. A compound according to claim 7 which is 1'-[4,4-bis(4-fluorophenyl)-3-butenyl]-7-chloro-2-methylspiro[2H-1,4-benzodioxepin-3(5H)4'-piperidine].
17. A compound according to claim 7 which is 1'-[2-[bis(4-fluorophenyl)methoxy]ethyl]-2-methylspiro[2H-1,4-benzodioxepin-3(5H)4'-piperidine].
18. A compound according to claim 7 which is 1'-[2-[bis(4-fluorophenyl)methoxy]ethyl]-7-fluoro-2-methylspiro[2H-1,4-benzodiozepin-3(5H)4'-piperidine].

19. A compound according to claim 7 which is 1-[4,4-bis(3-fluorophenyl)butyl]-7-chloro-2-methylspiro[2H-1,4-benzodioxepin-3(5H)4'-piperidine].
20. A compound according to claim 7 which is 1'-[4,4-bis(4-fluorophenyl)butyl]-2-methyl-7-nitrospiro[2H-1,4-benzodioxepin-3(5H)4'-piperidine].
21. A compound according to claim 7 which is 7-chloro-1'-[2-(bis(4-fluorophenyl)methoxy)ethyl]-2-methylspiro[2H-1,4-benzodioxepin-3(5H)4'-piperidine].
22. A compound according to claim 7 which is 7-chloro-1'-[2-(diphenylmethoxy)ethyl]-2-methylspiro[2H-1,4-benzodioxepin-3(5H)4'-piperidine].
23. A compound of the formula

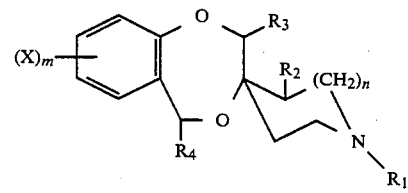

wherein
m is zero, 1 or 2;
n is zero or 1;
$R_1$ is (a) a $C_1$ to $C_5$ branched or straight chain alkyl group;

(b) a terminally substituted $C_1$, $C_2$ or $C_5$ branched or straight chain alkyl group or a terminally substituted $C_2$ or $C_5$ branched or straight chain alkenyl group, wherein the terminal substituents are one or two substituents independently selected from the group consisting of

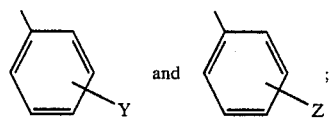

(c) a terminally substituted $C_1$ to $C_5$ branched or straight chain alkyl group, or a terminally substituted $C_2$ to $C_5$ branched or straight chain alkenyl group, or a terminally substituted $C_4$ alkynyl group, wherein the terminal substituents are one or two cyclohexyl groups;

(d) a $C_1$ or $C_2$ alkylene group terminally substituted by

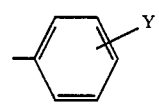

or $C_3$ to $C_5$ cycloalkyl;

(e) a $C_2$ to $C_3$ branched or straight chain alkylene group terminally substituted by one substituent selected from the group consisting of a

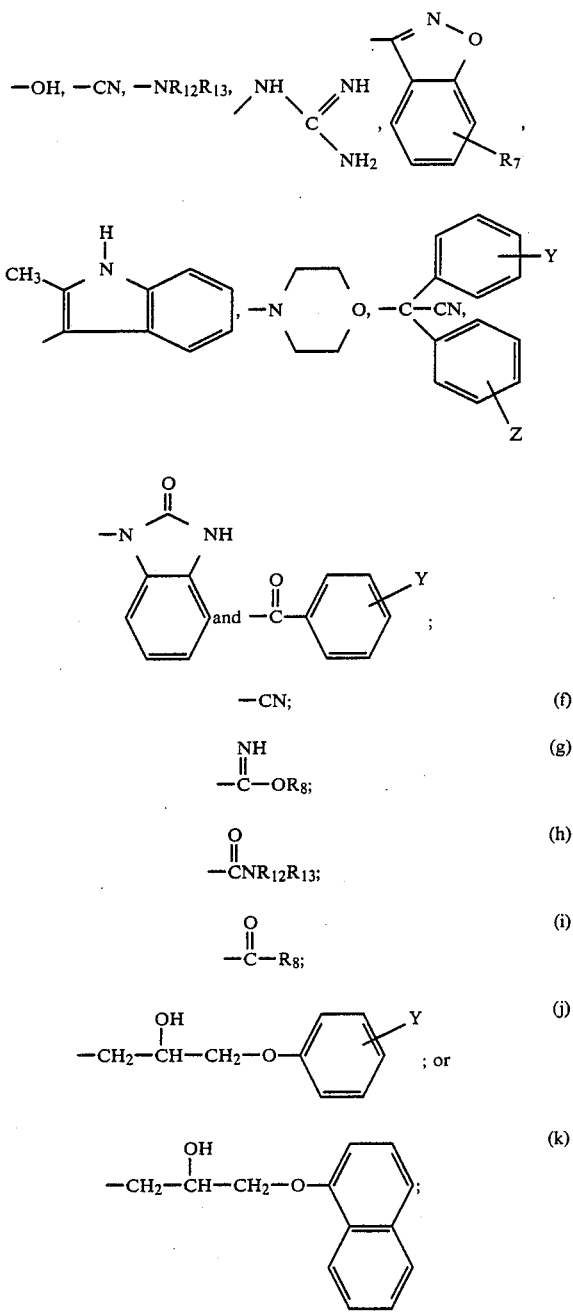

$R_2$ is hydrogen when n=0 or $R_2$ is hydrogen or a $C_1$ to $C_3$ straight chain alkyl group when n=1;

$R_3$ is hydrogen or a $C_1$ to $C_3$ straight chain alkyl group;

$R^4$ is hydrogen or a $C_1$ to $C_3$ straight chain alkyl group;

X is Cl, F, Br, I, $-NO_2$, $-CF_3$, $-NR_6R_7$,

$C_1$ to $C_6$ branched or straight chain alkyl, $-CN$, $-O-R_6$, $-SR_7$, $-SO_3R_7$,

$-NHCOR_8$, $-SO_2R_9$ or $-SOR_9$, where $R_6$ is hydrogen or a $C_1$ to $C_6$ straight chain alkyl group;

$R_7$ is hydrogen or a $C_1$ to $C_6$ straight chain alkyl group;

$R_8$ is a $C_1$ to $C_6$ branched or straight chain alkyl group;

$R_9$ is a $C_1$ to $C_6$ straight chain alkyl group; provided that when m=2, the X-substituents can be the same only when X is selected from the group consisting of Cl, F, Br, I, $C_1$ to $C_6$ branched or straight chain alkyl or $-O-R_6$;

Y and Z are the same or different and are independently selected from the group consisting of H, Cl, F, Br, I, $-NO_2$, $-CF_3$, $C_1$ to $C_4$ straight chain alkyl, alkoxy containing $C_1$ to $C_4$ straight chain alkyl, acyl or $-NH_2$;

$R_{10}$ is

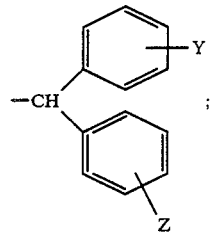

$R_{12}$ and $R_{13}$ are the same or different and are independently selected from the group consisting of hydrogen, methyl and ethyl; and the pharmaceutically acceptable salts and optical and geometric isomers thereof.

24. A compound according to claim 23 in which $R_2$, $R_3$ and $R_4$ are independently selected from hydrogen and a $C_1$ to $C_3$ straight chain alkyl group.

25. A compound according to claim 23 in which m=0.

26. A compound according to claim 23 in which m=1.

27. A compound according to claim 23 in which m=2.

28. A compound according to claim 26 in which X is Cl, F, Br or $NO_2$.

29. A compound of the formula

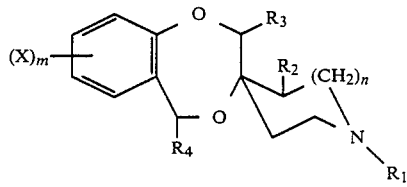

wherein
m is zero, 1 or 2;
n is zero or 1;
$R_1$ is
(a) a $C_1$, $C_2$ or $C_5$ branched or straight chain alkyl group, or a terminally substituted $C_2$ or $C_5$ branched or straight chain alkenyl group, wherein the terminal substituents are one or two substituents independently selected from the group consisting of

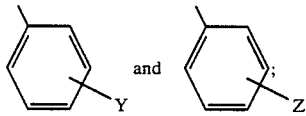

(b) a terminally substituted $C_1$ to $C_5$ branched or straight chain alkyl group, or a terminally substituted $C_2$ to $C_5$ branched or straight chain alkenyl group, or a terminally substituted $C_4$ alkynyl group, wherein the terminal substituents are one or two cyclohexyl groups;

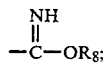 (c)

 (d)

 (e)

(f)

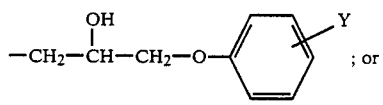 (g)

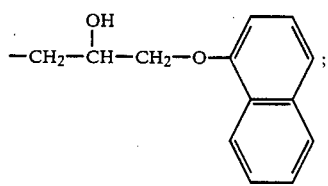 (h)

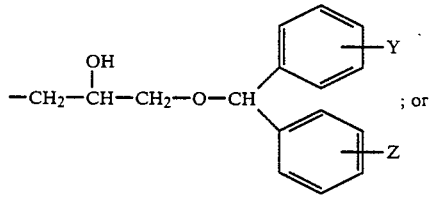 (i)

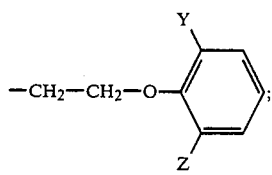 (j)

$R_2$ is hydrogen when $n=0$ or $R_2$ is hydrogen or a $C_1$ to $C_3$ straight chain alkyl group when $n=1$;
$R_3$ is hydrogen or a $C_1$ to $C_3$ straight chain alkyl group;
$R_4$ is hydrogen or a $C_1$ to $C_3$ straight chain alkyl group;
X is Cl, F, Br, I, —$NO_2$, —$CF_3$, —$NR_6R_7$,

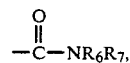

$C_1$ to $C_6$ branched or straight chain alkyl, —CN, —O—$R_6$, —$SR_7$, —$SO_3R_7$,

—$NHCOR_8$, —$SO_2R_9$ or —$SOR_9$, where
$R_6$ is hydrogen or a $C_1$ or $C_6$ straight chain alkyl group;
$R_7$ is hydrogen or a $C_1$ to $C_6$ straight chain alkyl group;
$R_8$ is a $C_1$ to $C_6$ branched or straight chain alkyl group;
$R_9$ is a $C_1$ to $C_6$ straight chain alkyl group; provided that when $m=2$, the X-substituents can be the same only when X is selected from the group consisting of Cl, F, Br, I, $C_1$ to $C_6$ branched or straight chain alkyl or —O—$R_6$;
Y and Z are the same or different and are independently selected from the group consisting of H, Cl, F, Br, I, —$NO_2$, —$CF_3$, $C_1$ to $C_4$ straight chain alkyl, alkoxy containing $C_1$ to $C_4$ straight chain alkyl, acyl or —$NH_2$;
$R_{12}$ and $R_{13}$ are the same or different and are independently selected from the group consisting of hydrogen, methyl and ethyl;
and the pharmaceutically acceptable salts and optical and geometric isomers thereof.

30. A compound according to claim 30 in which $n=1$.

31. A compound according to claim 30 in which $R_2$ and $R_4$ are each hydrogen.

32. A compound according to claim 31 in which X is Cl, F, Br or $NO_2$.

33. A compound according to claim 33 in which $R_3$ is —$CH_3$.

34. A compound according to claim 31 which is 1'-acetyl-2-methylspiro[2H-1,4-benzodioxepin-3(5H)4'-piperidine].

35. A compound according to claim 31 which is 1'-acetyl-2-methyl-7-nitrospiro[2H-1,4-benzodioxepin3(5H)4'-piperidine].

36. A compound according to claim 31 which is 7-chloro-2-methyl-1'-bis(4-fluorophenyl)methylspiro[2H-1,4-benzodioxepin-3(5H)4'-piperidine].

37. A compound according to claim 31 which is 2-methyl-1'-[5,5-bis(4-fluorophenyl)pentyl]spiro[2H-1,4-benzodioxepin-3(5H)4'-piperidine].

38. A compound according to claim 31 which is 7-chloro-2-methyl-1'-[5,5-bis(4-fluorophenyl)pentyl]-spiro[2H-1,4-benzodioxepin-3(5H)4'-piperidine].

39. A compound according to claim 31 which is 1'-(4,4-dicyclohexylbutyl)-7-chloro-2-methylspiro[2H-1,4-benzodioxepin-3(5H)4'-piperidine].

40. A compound according to claim 31 which is 2-methyl-1'-[2-hydroxy-3-phenoxypropyl]spiro[2H-1,4-benzodioxepin-3(5H)4'-piperidine].

41. A compound according to claim 31 which is 2-methyl-1'-[2-hydroxy-3-(4-methoxyphenoxy)propyl]-spiro[2H-1,4-benzodioxepin-3(5H)4'-piperidine].

42. A compound according to claim 31 which is 2-methyl-1'-[2-hydroxy-3-(4-fluorophenoxy)propyl]-spiro[2H-1,4-benzodioxepin-3(5H)4'-piperidine].

43. A compound according to claim 31 which is 7-chloro-2-methyl-1'-(2-hydroxy-3-phenoxypropyl)-spiro[2H-1,4-benzodioxepin-3(5H)4'-piperidine].

44. A compound according to claim 31 which is 7-chloro-2-methyl-1'-[2-hydroxy-3-(4-methoxyphenoxy)-propyl]spiro[2H-1,4-benzodioxepin-3(5H)4'-piperidine].

45. A compound according to claim 31 which is 7-chloro-2-methyl-1'-[2-hydroxy-3-(4-fluorophenoxy)-propyl]spiro[2H-1,4-benzodioxepin-3(5H)4'-piperidine].

46. A compound according to claim 31 which is 2-methyl-1'-[2-hydroxy-3-(1-naphthoxy)propyl]spiro[2H-1,4-benzodioxepin-3(5H)4'-piperidine].

47. A compound according to claim 31 which is 7-chloro-2-methyl-1'-[2-hydroxy-3-(1-naphthoxy)-propyl]spiro[2H-1,4-benzodioxepin-3(5H)4'-piperidine].

48. A compound according to claim 31 which is 2-methylspiro[2H-1,4-benzodioxepin-2(5H)4'-piperidine]-1'-carboximidic acid ethyl ester.

49. A compound according to claim 31 which is 7-chloro-1'-[2-(2,6-dimethoxyphenoxy)ethyl]-2-methyl-spiro[2H-1,4-benzodioxepin-3(5H)4'-piperidine].

50. A compound according to claim 31 which is 2-methyl-1'-[2-hydroxy-3[bis(4-fluorophenyl)methoxy]-propyl]spiro[2H-1,4-benzodioxepin-3(5H)4'-piperidine].

51. A compound of the formula

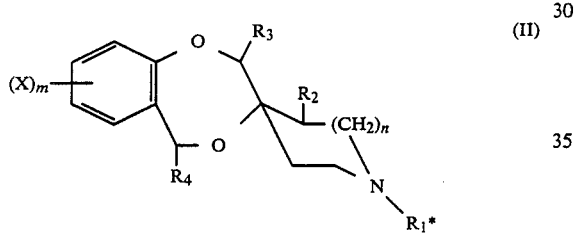

wherein $R_1^*$ is a $C_1$ to $C_5$ branched or straight chain alkyl group; a $C_1$ or $C_2$ alkylene group terminally substituted by

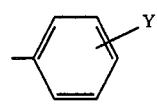

or $C_3$–$C_5$ cycloalkyl; a $C_2$ to $C_3$ straight chain alkylene group terminally substituted by one substituent selected from the group

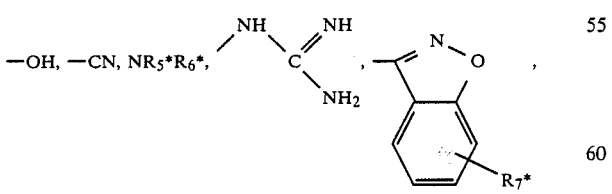

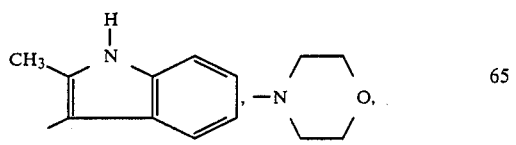

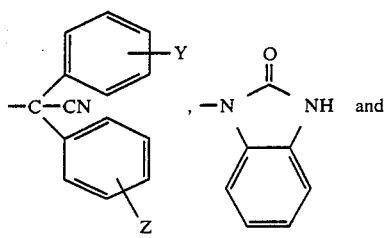

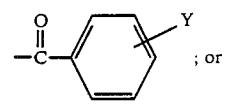

$R_1^*$ is —CN,

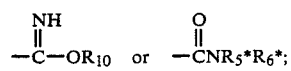

$R_5^*$ and $R_6^*$ are the same or different and are independently selected from the group consisting of hydrogen, methyl and ethyl;

$R_7^*$ is hydrogen, Cl, F, Br or I;

Y and Z are the same or different and are independently selected from the group consisting of H, Cl, F, Br, I, —NO$_2$, —CF$_3$, $C_1$ to $C_4$ straight chain alkyl, alkoxy containing $C_1$ to $C_4$ straight chain alkyl, acyl or —NH$_2$;

$R_2$ is hydrogen when n=0 or $R_2$ is hydrogen or a $C_1$ to $C_3$ straight chain alkyl group when n=1;

$R_3$ is hydrogen or a $C_1$ to $C_3$ straight chain alkyl group;

$R_4$ is hydrogen or a $C_1$ to $C_3$ straight chain alkyl group;

m is zero, 1 or 2;

X is Cl, F, Br, I, —NO$_2$, —CF$_3$, —NR$_6$R$_7$,

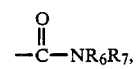

$C_1$ to $C_6$ branched or straight chain alkyl, —CN, —O—R$_6$, —SR$_7$, —SO$_3$R$_7$,

—NHCOR$_8$, —SO$_2$R$_9$ or —SOR$_9$ where $R_6$ is hydrogen or a $C_1$ to $C_6$ straight chain alkyl group, $R_7$ is hydrogen or a $C_1$ to $C_6$ straight chain alkyl group, $R_8$ is a $C_1$ to $C_6$ branched or straight chain alkyl group, $R_9$ is a $C_1$ to $C_6$ straight chain alkyl group; provided that when m=2, the X-substituents can be the same only when X is selected from the group consisting of Cl, F, Br, I, $C_1$ to $C_6$ branched or straight chain alkyl or —O—R$_6$;

n is zero or 1;

and the pharmaceutically acceptable salts and optical and geometric isomers thereof.

52. A compound according to claim 52 in which $R_1^*$ is a $C_1$ to $C_5$ straight chain alkyl group or a substituted $C_1$ to $C_3$ straight chain alkylene group.

53. A compound according to claim 53 in which $R_1^*$ is a pentyl, phenylethyl, cyanomethyl, cyanoethyl, hydroxyethyl, aminoethyl, aminopropyl, cyclopropylmethyl, p-nitrophenylethyl, p-aminophenylethyl, or 2-N,N-dimethylaminoethyl group, or an ethylene group terminally substituted by guanidino or

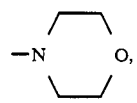

or a straight chain ethylene or propylene group terminally substituted by

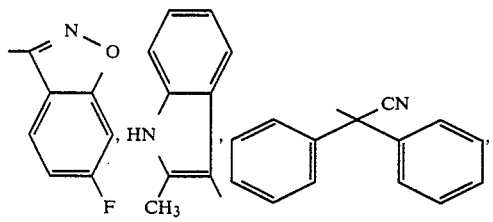

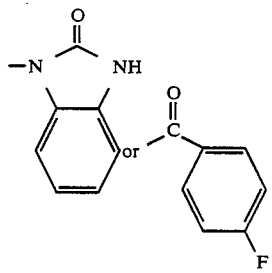

group.

54. A compound according to claim 52 in which $R_2$, $R_3$ and $R_4$ are independently selected from hydrogen and $C_1$ to $C_3$ straight chain alkyl groups.

55. A compound according to claim 51 in which m=0.

56. A compound according to claim 51 in which m=1.

57. A compound according to claim 52 in which X is Cl, F or Br.

58. A compound of the formula

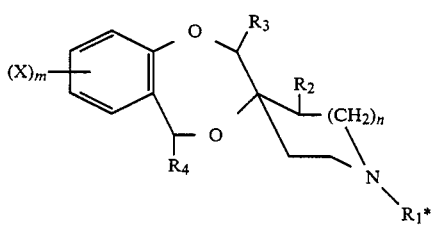

(II)

wherein $R_1^*$ is a $C_1$ to $C_5$ branched or straight chain alkyl group; a $C_2$ alkylene group terminally substituted by

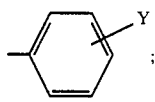

or a $C_2$ to $C_3$ branched or straight chain alkylene group terminally substituted by one substituent selected from the group consisting of a $C_3$ to $C_5$ cyclic alkyl group, —OH, —CN, $NR_5^*R_6^*$,

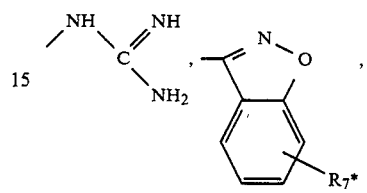

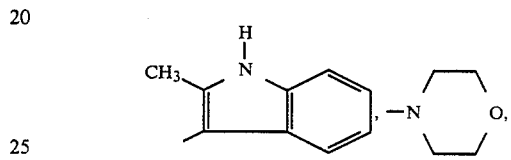

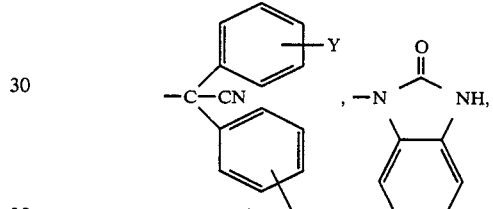

; or $R_1^*$ is —CN,

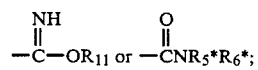

$R_5^*$ and $R_6^*$ are the same or different and are independently selected from the group consisting of hydrogen, methyl and ethyl;

$R_7^*$ is hydrogen, Cl, F, Br or I;

$R_{11}$ is a $C_1$ to $C_4$ straight chain alkyl group;

wherein

Y and Z are the same or different and are independently selected from the group consisting of H, Cl, F, Br, I, —NO$_2$, —CF$_3$, $C_1$ to $C_4$ straight chain alkyl, alkoxy containing $C_1$ to $C_4$ straight chain alkyl, acyl or —NH$_2$;

$R_2$, $R_3$ and $R_4$ are independently selected from hydrogen and methyl;

X is Cl, F, Br, I, —NO$_2$, —CH$_3$ or —OCH$_3$;

m is zero, 1 or 2;

n is zero or 1; provided that when m=2, the X-substituents can be the same only when X is selected from the group consisting of Cl, F, Br, I, —CH$_3$ and —OCH$_3$; and the pharmaceutically acceptable salts and optical and geometric isomers thereof.

59. A compound according to claim 58 in which n=1.

60. A compound according to claim 59 in which $R_2$ and $R_4$ are each hydrogen.

61. A compound according to claim 61, in which X is Cl, F or Br.

62. A compound according to claim 61 in which $R_3$ is —$CH_3$.

63. A compound according to claim 58 which is 1'-(cyanomethyl)-2-methylspiro[2H-1,4-benzodioxepin-3(5H)4'-piperidine].

64. A compound according to claim 58 which is 2-methyl-1'-(2-phenylethyl)spiro[2H-1,4-benzodioxepin-3(5H)4'-piperidine].

65. A compound according to claim 58 which is 1'-(2-hydroxyethyl)-2-methylspiro[2H-1,4-benzodioxepin-3(5H)4'-piperidine].

66. A compound according to claim 58 which is 1'-(2-aminoethyl)-2-methylspiro[2H-1,4-benzodioxepin-3(5H)4'-piperidine].

67. A compound according to claim 58 which is [2-(2-methylspiro[2H-1,4-benzodioxepin-3(5H)4'-piperidine]-1'-yl)ethyl]guanidine.

68. A compound according to claim 58 which is 1'-cyclopropyl-2-methylspiro[2H-1,4-benzodioxepin-3(5H)4'-piperidine].

69. A compound according to claim 58 which is 1'-[3-(6-fluoro-1,2-benzisoxazol-3-yl)propyl]-2-methyl-spiro[2H-1,4-benzodioxepin-3(5H)4'-piperidine].

70. A compound according to claim 58 which is 2-methyl-1'-[3-(2-methylindol-3-yl)propyl]spiro[2H-1,4-benzodioxepin-3(5H)4'-piperidine].

71. A compound according to claim 58 which is 2-methyl-1'-pentylspiro[2H-1,4-benxodioxepin-3(5H)4'-piperidine].

72. A compound according to claim 58 which is 2-methyl-1'-(3-aminopropyl)spiro[2H-1,4-benzodioxepin-3(5H)4'-piperidine].

73. A compound according to claim 58 which is 1'-[2-(4-nitrophenyl)ethyl]2-methylspiro[2H-1,4-benzodioxepin-3(5H)4'-piperidine].

74. A compound according to claim 58 which is 1'-[2-(4-aminophenyl)ethyl]-2-methylspiro[2H-1,4-benzodioxepin-3(5H)4'-piperidine].

75. A compound according to claim 58 which is 1'-(2-N,N-dimethylaminoethyl)-2-methylspiro[2H-1,4-benzodioxepin-3(5H)4'-piperidine].

76. A compound according to claim 58 which is 1'-[2-(1-morpholine)ethyl]-2-methylspiro[2H-1,4-benzodioxepin-3(5H)4'-piperidine].

77. A compound according to claim 58 which is 2-methyl-1'-[3-(1,3-dihydro-2-oxo-2H-benzimidazol-1-yl)-propyl]spiro[2H-1,4-benzodioxepin-3(5H)4'-piperidine].

78. A compound according to claim 58 which is 2-methyl-1'-[3-cyano-3,3-diphenylpropyl]spiro[2H-1,4-benzodioxepin-3(5H)4'-piperidine].

79. A compound according to claim 58 which is 8-chloro-2-methylspiro[2H-1,4-benzodioxepin-3(5H)4'-piperidine].

80. A compound according to claim 58 which is 8-chloro-1'-cyanomethyl-2-methylspiro[2H-1,4-benzodioxepin-3(5H)4'-piperidine].

81. A compound according to claim 58 which is 1'-(2-cyanoethyl)-2-methylspiro[2H-1,4-benzodioxepin-3(5H)4'-piperidine].

82. A compound according to claim 58 which is 1'-[4-(4-fluorophenyl)-4-oxobutyl]-2-methylspiro[2H-1,4-benzodioxepin-3(5H)4'-piperidine].

83. A composition for reducing hypertension comprising an effective amount of a compound of any one of claims 1 to 82 in admixture with a pharmaceutically acceptable carrier.

84. A composition for analgesia comprising an effective amount of a compound of any one of claims 51 to 82 in admixture with a pharmaceutically acceptable carrier.

85. A method for reducing hypertension in a mammal by administering to a mammal, in a amount sufficient to reduce blood pressure in the mammal, a compound as defined in claim 1.

86. A method for producing analgesia in a mammal by administering to a mammal, in an amount sufficient to alleviate pain in the mammal, a compound as defined in claim 1.

87. A compound according to claim 1 which is N,2-dimethylspiro[2H,1,4-benzodioxepin-3(5H)4'-piperidine]-1'-carboxamide.

88. A compound according to claim 1 which is N-ethyl-2'methylspiro[2H-1,4-benzodioxepin-3(5H)4'-piperidine]-1'-carboxamide.

89. A compound according to claim 1 which is 1'-methylspiro[2H-1,4-benzodioxepin-3(5H)4'-pipieridine]hydrochloride.

* * * * *